(12) United States Patent
Radaelli et al.

(10) Patent No.: US 10,407,361 B2
(45) Date of Patent: Sep. 10, 2019

(54) OXIDATIVE COUPLING OF METHANE FOR OLEFIN PRODUCTION

(71) Applicant: Siluria Technologies, Inc., San Francisco, CA (US)

(72) Inventors: Guido Radaelli, Pleasant Hill, CA (US); Suchia Duggal, San Rafael, CA (US); Joel Cizeron, Redwood City, CA (US); Wayne Schammel, Brisbane, CA (US); Franciscus J. A. Martens, Calgary (CA)

(73) Assignee: SILURIA TECHNOLOGIES, INC., San Francisco, CA (US)

( * ) Notice: Subject to any disclaimer, the term of this patent is extended or adjusted under 35 U.S.C. 154(b) by 0 days.

(21) Appl. No.: 15/912,104

(22) Filed: Mar. 5, 2018

(65) Prior Publication Data

US 2018/0327334 A1    Nov. 15, 2018

Related U.S. Application Data

(62) Division of application No. 15/487,181, filed on Apr. 13, 2017, now Pat. No. 9,944,573.
(Continued)

(51) Int. Cl.
*C07C 2/84* (2006.01)
*C07C 2/08* (2006.01)
(Continued)

(52) U.S. Cl.
CPC .................. *C07C 2/84* (2013.01); *C07C 2/08* (2013.01); *C07C 6/04* (2013.01); *C08F 10/02* (2013.01);
(Continued)

(58) Field of Classification Search
CPC .... C07C 2/84; C07C 2/08; C07C 6/04; C07C 11/04; C07C 9/06; C07C 11/08;
(Continued)

(56) References Cited

U.S. PATENT DOCUMENTS 2,324,172 A    7/1943  Parkhurst
2,486,980 A    11/1949 Robinson
(Continued)

FOREIGN PATENT DOCUMENTS

CA    2041874 A1    11/1992
CA    2765769 A1    1/2011
(Continued)

OTHER PUBLICATIONS

U.S. Appl. No. 62/050,729, filed Sep. 15, 2014.
(Continued)

*Primary Examiner* — William K Cheung
(74) *Attorney, Agent, or Firm* — Wilson Sonsini Goodrich & Rosati

(57) ABSTRACT

The present disclosure provides natural gas and petrochemical processing systems, including oxidative coupling of methane reactor systems that may integrate process inputs and outputs to cooperatively utilize different inputs and outputs in the production of higher hydrocarbons from natural gas and other hydrocarbon feedstocks. The present disclosure also provides apparatuses and methods for heat exchange, such as an apparatus that can perform boiling and steam super-heating in separate chambers in order to reach a target outlet temperature that is relatively constant as the apparatus becomes fouled. A system of the present disclosure may include an oxidative coupling of methane (OCM) subsystem that generates a product stream comprising compounds with two or more carbon atoms, and a dual com-
(Continued)

partment heat exchanger downstream of, and fluidically coupled to, the OCM subsystem.

20 Claims, 37 Drawing Sheets

Related U.S. Application Data

(60) Provisional application No. 62/417,102, filed on Nov. 3, 2016, provisional application No. 62/397,798, filed on Sep. 21, 2016, provisional application No. 62/379,675, filed on Aug. 25, 2016, provisional application No. 62/341,308, filed on May 25, 2016, provisional application No. 62/341,307, filed on May 25, 2016, provisional application No. 62/322,190, filed on Apr. 13, 2016.

(51) Int. Cl.
| | | |
|---|---|---|
| *C07C 6/04* | (2006.01) | |
| *F22B 1/16* | (2006.01) | |
| *F28F 9/22* | (2006.01) | |
| *F28F 9/26* | (2006.01) | |
| *F28F 19/00* | (2006.01) | |
| *F28D 7/16* | (2006.01) | |
| *C08F 10/02* | (2006.01) | |
| *C08F 10/06* | (2006.01) | |
| *F28D 7/10* | (2006.01) | |
| *F28D 21/00* | (2006.01) | |

(52) U.S. Cl.
CPC ............. *C08F 10/06* (2013.01); *F22B 1/16* (2013.01); *F28D 7/10* (2013.01); *F28D 7/16* (2013.01); *F28F 9/22* (2013.01); *F28F 9/26* (2013.01); *F28F 19/00* (2013.01); *F28D 2021/0022* (2013.01); *Y02P 20/52* (2015.11)

(58) Field of Classification Search
CPC ... C07C 11/06; F28D 7/16; F28D 7/10; F28D 2021/0022; F28F 19/00; F28F 9/26; F28F 9/22; C08F 10/02; C08F 10/06
USPC ........................................................ 526/75
See application file for complete search history.

(56) References Cited

U.S. PATENT DOCUMENTS

| | | |
|---|---|---|
| 2,577,701 A | 12/1951 | Deming et al. |
| 2,579,601 A | 12/1951 | Nelson et al. |
| 2,643,216 A * | 6/1953 | Findlay .................. C10G 9/30 159/44 |
| 2,673,221 A | 3/1954 | Schrader et al. |
| 2,880,592 A | 4/1959 | Davison et al. |
| 2,926,751 A | 3/1960 | Kohl et al. |
| 2,943,125 A | 6/1960 | Ziegler et al. |
| 3,094,569 A | 6/1963 | Thomas |
| 3,128,317 A | 4/1964 | Arkell et al. |
| 3,413,817 A | 12/1968 | Kniel |
| 3,459,678 A | 8/1969 | Hagemeyer, Jr. et al. |
| 3,584,071 A | 6/1971 | Mcnulty et al. |
| 3,596,473 A | 8/1971 | Streich |
| 3,660,519 A | 5/1972 | Takaaki et al. |
| 3,686,334 A | 8/1972 | Britton |
| 3,686,350 A | 8/1972 | Ono et al. |
| 3,702,886 A | 11/1972 | Argauer et al. |
| 3,751,878 A | 8/1973 | Collins |
| 3,862,257 A | 1/1975 | Buben et al. |
| 3,900,526 A | 8/1975 | Johnson et al. |
| 3,931,349 A | 1/1976 | Kuo |
| 4,012,452 A | 3/1977 | Frampton |
| 4,101,600 A | 7/1978 | Zhukov et al. |
| 4,107,224 A | 8/1978 | Dwyer |
| 4,126,645 A | 11/1978 | Collins |
| 4,132,745 A | 1/1979 | Amigues et al. |
| 4,140,504 A | 2/1979 | Campbell et al. |
| 4,314,090 A | 2/1982 | Shewbart et al. |
| 4,329,530 A | 5/1982 | Irvine et al. |
| 4,347,392 A | 8/1982 | Cosyns et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,481,305 A | 11/1984 | Jorn et al. |
| 4,489,215 A | 12/1984 | Withers |
| 4,554,395 A | 11/1985 | Jones et al. |
| 4,567,307 A | 1/1986 | Jones et al. |
| 4,629,718 A | 12/1986 | Jones et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,944 A | 4/1989 | Brazdil, Jr. et al. |
| 4,849,571 A | 7/1989 | Gaffney |
| 4,882,400 A | 11/1989 | Dumain et al. |
| 4,895,823 A | 1/1990 | Kolts et al. |
| 4,900,347 A | 2/1990 | McCue, Jr. et al. |
| 4,939,311 A | 7/1990 | Washecheck et al. |
| 4,939,312 A | 7/1990 | Baerns et al. |
| 4,950,311 A | 8/1990 | White, Jr. |
| 4,962,261 A | 10/1990 | Abrevaya et al. |
| 4,966,874 A | 10/1990 | Young et al. |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,041,405 A | 8/1991 | Lunsford et al. |
| 5,057,638 A | 10/1991 | Sweeney |
| 5,066,629 A | 11/1991 | Lukey et al. |
| 5,080,872 A | 1/1992 | Jezl et al. |
| 5,118,898 A | 6/1992 | Tyler et al. |
| 5,132,472 A | 7/1992 | Durante et al. |
| 5,137,862 A | 8/1992 | Mackrodt et al. |
| 5,179,056 A | 1/1993 | Bartley |
| 5,196,634 A | 3/1993 | Washecheck et al. |
| 5,198,596 A | 3/1993 | Kaminsky et al. |
| 5,240,474 A | 8/1993 | Auvil et al. |
| 5,254,781 A | 10/1993 | Calamur et al. |
| 5,263,998 A | 11/1993 | Mackrodt et al. |
| 5,288,935 A | 2/1994 | Alario et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,371,306 A | 12/1994 | Woo et al. |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,712,217 A | 1/1998 | Choudhary et al. |
| 5,714,657 A | 2/1998 | Devries |

(56) References Cited

U.S. PATENT DOCUMENTS

| | | |
|---|---|---|
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,866,737 A | 2/1999 | Hagemeyer et al. |
| 5,877,363 A | 3/1999 | Gildert et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Truebenbach et al. |
| 5,935,898 A | 8/1999 | Truebenbach et al. |
| 5,936,135 A | 8/1999 | Choudhary et al. |
| 5,959,170 A | 9/1999 | Withers, Jr. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,146,549 A | 11/2000 | Mackay et al. |
| 6,153,149 A | 11/2000 | Rabitz et al. |
| 6,221,986 B1 | 4/2001 | Commereuc et al. |
| 6,328,945 B1 | 12/2001 | Hufton et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,509,292 B1 | 1/2003 | Blankenship et al. |
| 6,518,476 B1 | 2/2003 | Culp et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,683,019 B2 | 1/2004 | Gartside et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,821,500 B2 | 11/2004 | Fincke et al. |
| 6,841,708 B1 | 1/2005 | Benje |
| 6,891,001 B2 | 5/2005 | Kuhlburger |
| 7,093,445 B2 | 8/2006 | Corr et al. |
| 7,157,612 B2 | 1/2007 | Ewert et al. |
| 7,176,342 B2 | 2/2007 | Bellussi et al. |
| 7,183,451 B2 | 2/2007 | Gattis et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |
| 7,795,490 B2 | 9/2010 | Iaccino et al. |
| 7,838,710 B2 | 11/2010 | Ryu |
| 7,868,216 B2 | 1/2011 | Chodorge et al. |
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 7,993,500 B2 | 8/2011 | Gilliam et al. |
| 8,071,836 B2 | 12/2011 | Butler |
| 8,080,215 B2 | 12/2011 | Taheri et al. |
| 8,129,305 B2 | 3/2012 | Bagherzadeh et al. |
| 8,137,444 B2 | 3/2012 | Farsad et al. |
| 8,153,851 B2 | 4/2012 | Gartside et al. |
| 8,163,070 B2 | 4/2012 | Hees et al. |
| 8,192,709 B2 | 6/2012 | Reyes et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,399,527 B1 | 3/2013 | Brown et al. |
| 8,399,726 B2 | 3/2013 | Chinta et al. |
| 8,435,920 B2 | 5/2013 | White et al. |
| 8,450,546 B2 | 5/2013 | Chinta et al. |
| 8,552,236 B2 | 10/2013 | Iaccino |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,759,598 B2 | 6/2014 | Hayashi et al. |
| 8,796,497 B2 | 8/2014 | Chinta et al. |
| 8,865,780 B2 | 10/2014 | Bogild |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 9,133,079 B2 | 9/2015 | Weinberger et al. |
| 9,321,702 B2 | 4/2016 | Nyce et al. |
| 9,334,204 B1 | 5/2016 | Radaelli et al. |
| 9,352,295 B2 | 5/2016 | Rafique et al. |
| 9,446,343 B2 | 9/2016 | Elliott et al. |
| 9,469,577 B2 | 10/2016 | Schammel et al. |
| 9,527,784 B2 | 12/2016 | Weinberger et al. |
| 9,556,086 B2 | 1/2017 | Schammel et al. |
| 9,567,269 B2 | 2/2017 | Radaelli et al. |
| 9,598,328 B2 | 3/2017 | Nyce et al. |
| 9,670,113 B2 | 6/2017 | Iyer et al. |
| 9,701,597 B2 | 7/2017 | Rafique et al. |
| 9,718,054 B2 | 8/2017 | Scher et al. |
| 9,751,079 B2 | 9/2017 | Freer et al. |
| 9,790,144 B2 | 10/2017 | Radaelli et al. |
| 9,944,573 B2 | 4/2018 | Radaelli et al. |
| 9,956,544 B2 | 5/2018 | Schammel et al. |
| 9,969,660 B2 | 5/2018 | Iyer et al. |
| 10,047,020 B2 | 8/2018 | Cizeron et al. |
| 2002/0007101 A1 | 1/2002 | Senetar et al. |
| 2002/0015670 A1 | 2/2002 | Shah et al. |
| 2002/0150522 A1 | 10/2002 | Heim et al. |
| 2002/0182735 A1 | 12/2002 | Kibby et al. |
| 2003/0033932 A1 | 2/2003 | Sirkar et al. |
| 2003/0072700 A1 | 4/2003 | Goebel et al. |
| 2003/0189202 A1 | 10/2003 | Li et al. |

(56) References Cited

U.S. PATENT DOCUMENTS

| | | |
|---|---|---|
| 2003/0233019 A1 | 12/2003 | Sherwood |
| 2004/0220053 A1 | 11/2004 | Bagherzadeh et al. |
| 2005/0065391 A1 | 3/2005 | Gattis et al. |
| 2005/0065392 A1 | 3/2005 | Peterson et al. |
| 2006/0018821 A1 | 1/2006 | Suzuki et al. |
| 2006/0155157 A1 | 7/2006 | Zarrinpashne et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2007/0135668 A1 | 6/2007 | Sumner |
| 2008/0121383 A1 | 5/2008 | Birk |
| 2008/0141713 A1 | 6/2008 | Verma |
| 2008/0154078 A1 | 6/2008 | Bozzano et al. |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2008/0300436 A1 | 12/2008 | Cheung et al. |
| 2009/0042998 A1 | 2/2009 | Hashimoto et al. |
| 2009/0043141 A1 | 2/2009 | Mazanec et al. |
| 2009/0087496 A1 | 4/2009 | Katusic et al. |
| 2009/0202427 A1 | 8/2009 | Katusic et al. |
| 2009/0209412 A1 | 8/2009 | Parent et al. |
| 2009/0216059 A1 | 8/2009 | Reyes et al. |
| 2009/0259076 A1 | 10/2009 | Simmons et al. |
| 2009/0267852 A1 | 10/2009 | Tahmisian, Jr. et al. |
| 2009/0277837 A1 | 11/2009 | Liu et al. |
| 2010/0000153 A1 | 1/2010 | Kurkjian et al. |
| 2010/0003179 A1 | 1/2010 | Katusic et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0222203 A1 | 9/2010 | Baba et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0036728 A1 | 2/2011 | Farsad |
| 2011/0049132 A1 | 3/2011 | Lee |
| 2011/0052466 A1 | 3/2011 | Liu |
| 2011/0124488 A1 | 5/2011 | Neltner et al. |
| 2011/0160508 A1 | 6/2011 | Ma et al. |
| 2011/0189559 A1 | 8/2011 | De Miranda et al. |
| 2011/0240926 A1 | 10/2011 | Schellen et al. |
| 2011/0257453 A1 | 10/2011 | Chinta et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2013/0023079 A1 | 1/2013 | Kang et al. |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0178680 A1 | 7/2013 | Ha et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0291720 A1 | 11/2013 | Blood et al. |
| 2014/0012053 A1 | 1/2014 | Iyer et al. |
| 2014/0018589 A1 | 1/2014 | Iyer et al. |
| 2014/0061540 A1 | 3/2014 | Long et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0065767 A1 | 3/2015 | Henao et al. |
| 2015/0152025 A1 | 6/2015 | Cizeron et al. |
| 2015/0210610 A1 | 7/2015 | Rafique et al. |
| 2015/0218786 A1 | 8/2015 | Cullen |
| 2015/0232395 A1 | 8/2015 | Nyce et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0368167 A1 | 12/2015 | Weinberger et al. |
| 2016/0074844 A1 | 3/2016 | Freer et al. |
| 2016/0089637 A1 | 3/2016 | Chang et al. |
| 2016/0272557 A1 | 9/2016 | Radaelli et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0275217 A1 | 9/2017 | Weinberger et al. |
| 2017/0283345 A1 | 10/2017 | Schammel et al. |
| 2017/0297975 A1 | 10/2017 | Radaelli et al. |

FOREIGN PATENT DOCUMENTS

| | | |
|---|---|---|
| CA | 2800142 C | 6/2018 |
| CN | 1403375 A | 3/2003 |
| CN | 101224432 A | 7/2008 |
| CN | 101387019 A | 3/2009 |
| CN | 102093157 A | 6/2011 |
| CN | 102125825 A | 7/2011 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |
| DE | 4338416 C1 | 4/1995 |
| DE | 102011080294 A1 | 2/2013 |
| EP | 0253522 A2 | 1/1988 |
| EP | 0303438 A2 | 2/1989 |
| EP | 0608447 A1 | 8/1994 |
| EP | 0634211 A1 | 1/1995 |
| EP | 0722822 A1 | 7/1996 |
| EP | 0761307 A1 | 3/1997 |
| EP | 0764467 A1 | 3/1997 |
| EP | 0716064 B1 | 7/1998 |
| EP | 1110930 A1 | 6/2001 |
| EP | 1632467 A1 | 3/2006 |
| EP | 1749807 A1 | 2/2007 |
| EP | 1749806 B1 | 10/2008 |
| EP | 3081292 A1 | 10/2016 |
| FR | 649429 A | 12/1928 |
| FR | 2600556 A1 | 12/1987 |
| GB | 733336 A | 7/1955 |
| GB | 2191212 A | 12/1987 |
| JP | 2005161225 A | 6/2005 |
| RU | 2412147 C2 | 2/2011 |
| RU | 2447048 C1 | 4/2012 |
| WO | WO-8607351 A1 | 12/1986 |
| WO | WO-2002004119 A1 | 1/2002 |
| WO | WO-2004033488 A2 | 4/2004 |
| WO | WO-2004056479 A1 | 7/2004 |
| WO | WO-2004103936 A1 | 12/2004 |
| WO | WO-2005067683 A2 | 7/2005 |
| WO | WO-2007130515 A2 | 11/2007 |
| WO | WO-2008005055 A2 | 1/2008 |
| WO | WO-2008014841 A1 | 2/2008 |

(56) References Cited

FOREIGN PATENT DOCUMENTS

| WO | WO-2008022147 A1 | 2/2008 |
|---|---|---|
| WO | WO-2008073143 A2 | 6/2008 |
| WO | WO-2009071463 A2 | 6/2009 |
| WO | WO-2009074203 A1 | 6/2009 |
| WO | WO-2009115805 A1 | 9/2009 |
| WO | WO-2010005453 A2 | 1/2010 |
| WO | WO-2011008464 A1 | 1/2011 |
| WO | WO-2011041184 A2 | 4/2011 |
| WO | WO-2011050359 A1 | 4/2011 |
| WO | WO-2010069488 A8 | 5/2011 |
| WO | WO-2011149996 A2 | 12/2011 |
| WO | WO-2012162526 A2 | 11/2012 |
| WO | WO-2013106771 A2 | 7/2013 |
| WO | WO-2013177433 A2 | 11/2013 |
| WO | WO-2013177461 A2 | 11/2013 |
| WO | WO-2014011646 A1 | 1/2014 |
| WO | WO-2014049445 A2 | 4/2014 |
| WO | WO-2014143880 A1 | 9/2014 |
| WO | WO-2015048295 A1 | 4/2015 |
| WO | WO-2015066693 A1 | 5/2015 |
| WO | WO-2015081122 A2 | 6/2015 |
| WO | WO-2015105911 A1 | 7/2015 |
| WO | WO-2015106023 A1 | 7/2015 |
| WO | WO-2015081122 A3 | 12/2015 |
| WO | WO-2016012371 A1 | 1/2016 |
| WO | WO-2016149507 A1 | 9/2016 |
| WO | WO-2016160563 A1 | 10/2016 |
| WO | WO-2017065947 A1 | 4/2017 |
| WO | WO-2017180910 A1 | 10/2017 |
| WO | WO-2018118105 A1 | 6/2018 |

OTHER PUBLICATIONS

U.S. Appl. No. 62/073,478, filed Oct. 31, 2014.
Iwamoto, M. One step formation of propene from ethene or ethanol through metathesis on nickel ion-loaded silica. Molecules. Sep. 13, 2011;16(9):7844-63.
Nijem, et al. Tuning the gate opening pressure of Metal-Organic Frameworks (MOFs) for the selective separation of hydrocarbons. J Am Chem Soc. Sep. 19, 2012;134(37):15201-4. Epub Sep. 10, 2012.
Pan, Sharp separation of C2/C3 hydrocarbon mixtures by zeolitic imidazolate framework-8 (ZIF-8) membranes synthesized in aqueous solutions. Chem Commun (Camb). Oct. 7, 2011;47(37):10275-7. doi: 10.1039/c1cc14051e. Epub Aug. 22, 2011.
Process Systems; "Steam Tables" Apr. 8, 2017—https://web.archive.org/web/20170408152403/https://valvesonline.com.au/references/steam-tables/.
Ahari, et al. Effects of operating parameters on oxidative coupling of methane over Na—W—Mn/SiO2 catalyst at elevated pressures. Journal of Natural Gas Chemistry. vol. 20, Issue 2, Mar. 2011, pp. 204-213.
PCT/US2018/041322 International Search Report and Written Opinion dated Sep. 24, 2018.
PCT/US2018/34184 International Search Report and Written Opinion dated Sep. 26, 2018.
U.S. Appl. No. 15/272,205 Office Action dated Sep. 25, 2018.
U.S. Appl. No. 15/354,886 Office Action dated Aug. 31, 2018.
U.S. Appl. No. 16/021,441 Office Action dated Aug. 28, 2018.
Co-pending U.S. Appl. No. 16/021,441, filed Jun. 28, 2018.
Co-pending U.S. Appl. No. 16/035,311, filed Jul. 13, 2018.
Co-pending U.S. Appl. No. 15/987,068, filed May 23, 2018.
Co-pending U.S. Appl. No. 16/030,298, filed Jul. 9, 2018.
Lunsford, et al. The oxidative coupling of methane on chlorinated Lithium-doped magnesium oxide. J. Chem. Soc., Chem. Commun., 1991, 1430-1432.
Bloch, et al. Hydrocarbon Separations in a Metal-Organic Framework with Open Iron(II) Coordination Sites, Science, 2012, 335:1606-1610.
Co-pending U.S. Appl. No. 15/888,777, filed Feb. 5, 2018.
Co-pending U.S. Appl. No. 15/950,461, filed Apr. 11, 2018.
Hosseinpour, Performance of CaX Zeolite for Separation of C2H6, C2H4, and CH4 by Adsorption Process; Capacity, Selectivity, and Dynamic Adsorption Measurements, Separation Science and Technology, 2011, 46:349-355.
Keller, Gas-Adsorption Processes: State of the Art, American Chemical Society, 1983, pp. 145-169.
Rousseau, Handbook of Separation Process Technology, 1987, p. 682.
U.S. Appl. No. 13/936,870 Notice of Allowance dated Mar. 21, 2018.
U.S. Appl. No. 14/553,795 Notice of Allowance dated May 25, 2018.
U.S. Appl. No. 15/888,777 Office Action dated Apr. 26, 2018.
U.S. Appl. No. 14/868,911 Office Action dated May 29, 2018.
U.S. Appl. No. 15/076,402 Office Action dated Mar. 8, 2018.
U.S. Appl. No. 15/356,202 Office Action dated Apr. 26, 2018.
U.S. Appl. No. 15/476,889 Office Action dated Apr. 30, 2018.
U.S. Appl. No. 15/487,181 Corrected Notice of Allowability dated Mar. 1, 2018.
U.S. Appl. No. 15/487,181 Notice of Allowability dated Feb. 13, 2018.
U.S. Appl. No. 15/487,181 Notice of Allowance dated Jan. 30, 2018.
U.S. Appl. No. 15/487,181 Supplemental Notice of Allowability dated Feb. 7, 2018.
Agarwal, et al., Aqueous Au—Pd colloids catalyze selective CH4 oxidation to CH3OH with O2 under mild conditions, Science 358, Oct. 13, 2017, 223-27.
American Petroleum Institute Publication 534 Heat Recovery Steam Generators Jan. 1995 (51 pages).
Autothermal Partial Oxidative Coupling of Methane. IP.com, Prior Art Database Technical Disclosure, Jul. 29, 2008, 5 pages.
Barrett, et al. The determination of pore volume and area distributions in porous substances—Compuatations from nitrogen isotherms. J. Am. Chem. Soc., 1951, vol. 73, pp. 373-380.
Berstad, D. et al. Low-temperature CO2 removal from natural gas. Energy Procedia (2012) 26:41-48.
Bollmann, et al. Ethylene tetramerization: a new route to produce 1-octene in exceptionally high selectivities. J Am Chem Soc. Nov. 17, 2004;126(45):14712-3.
Botella, et al. Effect of Potassium Doping on the Catalytic Behavior of Mo—V—Sb Mixed Oxide Catalysts in the Oxidation of Propane to Acrylic Acid. Catalysis Letters, Sep. 2003, vol. 89, Issue 3-4, pp. 249-253.
Carter, et al. High activity ethylene trimerisation catalysts based on diphosphine ligands. Chem Commun (Camb). Apr. 21, 2002;(8):858-9.
Cavani, et al. Oxidative dehydrogenation of ethane and propane: How far from commercial implementation? Catalysis Today. 2007; 127(1-4):113-131.
Chemsystems PERP Report Ethylene Oxide/Ethylene Glycol 2005.
Chen, et al. M2 Forming—A Process for Aromatization of Light Hydrocarbons. Ind. Eng. Chem. Process. Des. Dev. 1986, 25, 151-155.
Choudhary, et al. Aromatization of dilute ethylene over Ga-modified ZSM-5 type zeolite catalysts. Microporous and Mesoporous Materials 47: 253-267, 2001.
Choudhary, et al. Oxidative conversion of methane/natural gas into higher hydrocarbons. Catalysis Surveys from Asia 8(1): 15-25, Feb. 2004.
Choudhary, et al. Surface Basicity and Acidity of Alkaline Earth-Promoted La2 O3 Catalysts and Their Performance in Oxidative Coupling of Methane. Journal of Chemical Technology and Bio technology 72:125-130, 1998.
Christopher, et al. Engineering Selectivity in Heterogeneous Catalysis: Ag Nanowires as Selective Ethylene Epoxidation Catalysts. Journal of the American Chemical Society 130: 11264-11265, 2008.
Co-pending U.S. Appl. No. 14/789,901, filed Jul. 1, 2015.
Co-pending U.S. Appl. No. 14/868,911, filed Sep. 29, 2015.
Co-pending U.S. Appl. No. 15/076,402, filed Mar. 21, 2016.
Co-pending U.S. Appl. No. 15/354,886, filed Nov. 17, 2016.
Co-pending U.S. Appl. No. 15/356,202, filed Nov. 18, 2016.
Co-pending U.S. Appl. No. 15/359,399, filed Nov. 22, 2016.
Co-pending U.S. Appl. No. 15/476,889, filed Mar. 31, 2017.

(56) References Cited

OTHER PUBLICATIONS

Co-pending U.S. Appl. No. 15/581,996, filed Apr. 28, 2017.
Co-pending U.S. Appl. No. 15/690,090, filed Aug. 29, 2017.
Co-pending U.S. Appl. No. 15/699,798, filed Sep. 8, 2017.
Debart, et al. α-MNO2 Nanowires: A catalyst for the O2 Electrode in Rechargeabl Lithium Batteries. Angewandte Chemie International Edition 47: 4521-4524, 2008.
Enger, et al. A review of catalytic partial oxidation of methane to synthesis gas with emphasis on reaction mechanisms over transition metal catalysts. Applied Catalysis A: General 346 (1-2): 1-27, Aug. 2008.
European search report and search opinion dated Jan. 20, 2016 for EP Application No. 13817389.3.
Extended European search report and opinion dated Jul. 19, 2017 for EP Application No. 15734911.9.
Fallah, et al., A New Nano-(2Li2O/MgO) Catalyst/Porous Alpha-Alumina Composite for the Oxidative Coupling of Methane Reaction, AIChE Journal, Mar. 2010, 56(3):717-28.
Gao, et al. A study on methanol steam reforming to CO2 and H2 over the La2 CO4 nanofiber catalyst. Journal of Solid State Chemistry 181: 7-13, 2008.
Gao, et al. The direct decomposition of NO over the La2 CuO4 nanofiber catalyst. Journal of Solid State Chemistry 181: 2804-2807, 2008.
Ghosh, et al., Absorption of carbon dioxide into aqueous potassium carbonate promoted by boric acid, Energy Procedia, Feb. 2009, pp. 1075-1081.
Graves, C.R. Recycling CO2 into Sustainable Hydrocarbon Fuels: Electrolysis of CO2 and H2O. Dissertation, Columbia University (2010).
Guo, et al. Current Status and Some Perspectives of Rare Earth Catalytic Materials. Journal of The Chinese Rare Earth Society 25(1): 1-15, Feb. 2007.
Guo, X. et al. Direct, Nonoxidative Conversion of Methane to Ethylene, Aromatics, and Hydrogen. Science (2014) 344:616-619.
Gupta, M. Review on Heat Recovery Unit with Thermoelectric Generators. Intl J Eng and Innov Tech (IJEIT) (2014) 4(4):128-131.
Huang, et al. Exploiting shape effects of La2O3 nanocrystals for oxidative coupling of methane reaction. Nanoscale—Electronic Supplementary Material, 2013, 7 pages.
Huang, et al. Exploiting shape effects of La2 $O_3$ nanocrystals for oxidative coupling of methane reaction. Nanoscale 5(22): 10844-10848, 2013.
International preliminary report on patentability dated Jul. 21, 2016 for PCT Application No. US2015/010688.
International search report and written opinion dated Mar. 6, 2014 for PCT/US2013/042480.
International search report and written opinion dated Mar. 17, 2014 for PCT Application No. US2013/021312.
International search report and written opinion dated Jun. 12, 2015 for PCT Application No. US2015/010688.
International search report and written opinion dated Aug. 11, 2016 for PCT/US2016/024195.
International search report and written opinion dated Aug. 16, 2017 for PCT Application US2017027483.
International search report and written opinion dated Aug. 18, 2016 for PCT/US2016/022891.
International search report and written opinion dated Sep. 5, 2017 for PCT Application US2017025544.
International search report and written opinion dated Nov. 1, 2013 for PCT/US2013/049742.
International search report and written opinion dated Nov. 11, 2015 for PCT Application No. US2014/067465.
International search report and written opinion dated Feb. 2, 2017 for PCT Application No. US2016052959.
International search report dated Mar. 19, 2014 for PCT Application No. US2013/073657.
Kaibe, H. et al. Recovery of Plant Waste Heat by a Thermoelectric Generating System. Komatsu Tech Report (2011) 57(164):26-30.
Kaminsky, M.P. et al. Deactivation of Li-Based Catalysts for Methane Oxidative Coupling. Poster ACS Symposium on Natural Gas Upgrading II (Apr. 5-10, 1992).
Kaminsky, M.P. et al. Oxygen X-Ray Absorption Near-Edge Structure Characterization of the Ba-Doped Yttria Oxidative Coupling Catalyst. J Catalysis (1992) 136:16-23.
Keller, et al. Synthesis of Ethylene via Oxidative Coupling of Methane. Journal of Catalysis 73: 9-19, 1982.
Knuuttila, et al. Advanced Polyethylene Technologies—Controlled Material Properties. Long Term Properties of Polyolefins Advances in Polymer Science vol. 169, 2004, pp. 13-28.
Kuang, et al. Grafting of PEG onto lanthanum hydroxide nanowires. Materials Letters 62:4078-4080, 2008.
Labinger. Oxidative coupling of methane: an inherent limit to selectivity? Catal. Lett. 1988; 1:371-376.
Li, B. et al. Advances in CO2 capture technology: A patent review. Applied Energy (2013) 102:1439-1447.
Li, et al. Combined Single-Pass Conversion of Methane via Oxidative Coupling and Dehydroaromatization. Catalysis Letters, Sep. 2003, vol. 89, Issue 3-4, pp. 275-279.
Li, et al. Energy and Fuels. 2008, 22: 1897-1901.
Ling, et al. Preparation of Ag core—A Ushell Nanowires and Their Surface Enhanced Raman Spectroscopic Studies. Acta Chimica Sinica. 65 (9): 779-784, 2007.
Liu, et al. A novel Na2 WO4-Mn.SiC monolithic foam catalyst with improved thermal properties for the oxidative coupling of methane. Catalysis Communications 9: 1302-1306, 2008.
Lunsford, J.H. Catalytic conversion of methane to more useful chemicals and fuels: a challenge for the 21st century. Catalysis Today (2000) 63:165-174.
Lunsford. The Catalytic Oxidative Coupling of Methane. Angew. Chem Int. Ed. Engl. 1995; 34:970-980.
Matherne, et al. Chapter 14, Direct Conversion of Methane to C2's and Liquid Fuels: Process Economics, Methane Conversion by Oxidative Processes (1992), 463-482.
Miltenburg, A.S. Adsorptive Separation of Light Olefin/Paraffin Mixtures: Dispersion of Zeolites. (2007) Ponsen & Looijen B.V., Wageningen, the Netherlands.
Mimoun, H. et al. Oxypyrolysis of Natural Gas. Appl Catalysis (1990) 58:269-280.
Mleczko, et al. Catalytic oxidative coupling of methane—reaction engineering aspects and process schemes. Fuel Processing Technology 42:217-248, 1995.
Natural Gas Spec Sheet, 2003, prepared by Florida Power and Light Company.
Neltner, et al. Production of Hydrogen Using Nanocrystalline Protein-templated catalysts on M12 Phage. ACSNano 4(6):3227-3236, 2010.
Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nghiem, XS. Ethylene Production by Oxidative Coupling of Methane: New Process Flow Diagram based on Adsorptive Separation. Berlin, Mar. 14, 2014.
Nielsen, et al. Treat LPGs with amines. Hydrocarbon Process 79 (1997): 49-59.
Niu, et al. Preparation and characterization of La2 $O_3CO_3$ nanowires with high surface areas. Jounral of the Chinese Rare Earth Society 23 (Spec. Issue): 33-36, Dec. 2005.
Notice of allowance dated Sep. 9, 2016 for U.S. Appl. No. 15/076,480.
Notice of allowance dated Oct. 6, 2016 for U.S. Appl. No. 15,076,480.
Notice of allowance dated Jan. 4, 2016 for U.S. Appl. No. 14/789,953.
Notice of allowance dated Jan. 10, 2017 for U.S. Appl. No. 15/076,480.
Notice of allowance dated Jan. 13, 2016 for U.S. Appl. No. 14/789,946.
Notice of allowance dated Mar. 15, 2017 for U.S. Appl. No. 13/936,783.
Notice of allowance dated Apr. 27, 2016 for U.S. Appl. No. 13/900,898.
Notice of allowance dated May 16, 2017 for U.S. Appl. No. 14/592,668.
Notice of allowance dated Jun. 8, 2015 for U.S. Appl. No. 13/739,954.

(56) References Cited

OTHER PUBLICATIONS

Notice of allowance dated Aug. 9, 2016 for U.S. Appl. No. 15/076,480.
Notice of allowance dated Aug. 10, 2017 for U.S. Appl. No. 15/341,551.
Notice of allowance dated Aug. 11, 2016 for U.S. Appl. No. 13/900,898.
Notice of allowance dated Aug. 22, 2016 for U.S. Appl. No. 14/820,460.
Notice of Allowance dated Sep. 21, 2017 for U.S. Appl. No. 15/341,551.
Notice of allowance dated Sep. 22, 2016 for U.S. Appl. No. 13/936,870.
Notice of allowance dated Oct. 24, 2016 for U.S. Appl. No. 14/789,901.
Notice of allowance dated Dec. 5, 2016 for U.S. Appl. No. 15/076,480.
Office action dated Jan. 14, 2016 for U.S. Appl. No. 13/936,870.
Office Action dated Jan. 25, 2018 for U.S. Appl. No. 15/354,886.
Office action dated Mar. 6, 2017 for U.S. Appl. No. 13/936,870.
Office action dated Mar. 16, 2016 for U.S. Appl. No. 14/789,901.
Office action dated Apr. 22, 2016 for U.S. Appl. No. 15/076,480.
Office action dated May 20, 2016 for U.S. Appl. No. 14/820,460.
Office action dated Jul. 21, 2017 for U.S. Appl. No. 15/076,402.
Office action dated Jul. 29, 2016 for U.S. Appl. No. 14/789,901.
Office action dated Sep. 6, 2017 for U.S. Appl. No. 13/936,870.
Office action dated Sep. 11, 2015 for U.S. Appl. No. 14/789,946.
Office action dated Sep. 11, 2015 for U.S. Appl. No. 14/789,953.
Office action dated Oct. 4, 2016 for U.S. Appl. No. 15/076,402.
Office action dated Oct. 23, 2014 for U.S. Appl. No. 13/739,954.
Office Action dated Oct. 27, 2017 for U.S. Appl. No. 14/553,795.
Office action dated Nov. 2, 2015 for U.S. Appl. No. 14/789,901.
Office Action dated Nov. 6, 2017 for U.S. Appl. No. 14/868,911.
Office action dated Nov. 7, 2016 for U.S. Appl. No. 13/936,783.
Office action dated Nov. 13, 2015 for U.S. Appl. No. 13/900,898.
Office Action dated Nov. 30, 2017 for U.S. Appl. No. 15/272,205.
Office action dated Dec. 23, 2015 for U.S. Appl. No. 13/936,783.
Office action dated Dec. 23, 2016 for U.S. Appl. No. 14/592,668.
Office action dated Jan. 26, 2017 for U.S. Appl. No. 15/341,551.
Ohashi, Y. et al. Development of Carbon Dioxide Removal System from the Flue Gas of Coal Fired Power Plant. Energy Procedia (2011) 4:29-34.
Oil Refinery—Wikipedia, The Free Encyclopedia Website. Jan. 2009.
Olah, G. Hydrocarbon Chemistry. 2nd Edition, John Wiley & Sons, 2003.
Pak, et al. Elementary Reactions in the Oxidative Coupling of Methane over Mn/NA2 WO4/SiO2 and Mn/NA2 WO4/MgO Catalysts. Journal of Catalysis 179:222-230, 1998.
Qiu, et al. Steady-state conversion of methane to aromatics in high yields using an integrated recycle reaction system. Catalysis Letters 48: 11-15, 1997.
Saito, et al. Dehydrogenation of Propane Over a Silica-Supported Gallium Oxide Catalyst. Catalysis Letters, Sep. 2003, vol. 89, Issue 3-4, pp. 213-217.
Schweer, et al. OCM in a fixed bed reactor: limits and perspectives. Catalysis Today, vol. 21, No. 2-3, Dec. 1, 1994, pp. 357-369.
Seeberger, A. et al. Gas Separation by Supported Ionic Liquid Membranes. DGMK-Conference, Hamburg, Germany (2007).
Sheridan, D. et al. PCT/US2014/067465 filed Nov. 25, 2014 for Integrated Mixers and Heat Exchangers for Oxidative Coupling Methane Systems.
Simons, K. Membrane Technologies for CO2 Capture. Dissertation, U. of Twente (2010).
Smith, et al. Recent developments in solvent absorption technologies at the CO2CRC in Australia. Energy Procedia 1(2009): 1549-1555.
Somorjai, et al. High technology catalysts towards 100% selectivity Fabrication, characterization and reaction studies. Catalysis today 100:201-215, 2005.
Sugiyama, et al. Redox Behaviors of Magnesium Vanadate Catalysts During the Oxidative Dehydrogenation of Propane. Catalysis Letters, Sep. 2003, vol. 89, Issue 3-4, pp. 229-233.
Suzuki, K. Toshiba's Activity in Clean Coal and Carbon Capture Technology for Thermal Power Plants. APEC Clean Fossil Energy Technical and Policy Seminar (Feb. 22, 2012).
Takanabe, et al. Mechanistic Aspects and Reaction Pathways for Oxidative Coupling of Methane on Mn/NA2 WO4/SiO2 Catalysts. Journal of Physical Chemistry C 113(23):10131-10145, 2009.
Takanabe, et al. Rate and Selectivity Enhancements Mediated by OH Radicals in the Oxidative coupling of Methane Catalyzed by Mn/NA2 WO4/SiO2 . Angewandte Chemie International Edition 47:7689-7693, 2008.
Tong, et al. Development strategy research of downstream products of ethene in Tianjin. Tianjin Economy, pp. 37-40,1996.
Trautmann, et al. Cryogenic technology for nitrogen rejection from variable content natural gas. Presented at the XIV Convencion Internacional de Gas, Caracas, Venezuela, May 10-12, 2000, 13 pages.
Supplementary European search report dated Jun. 27, 2017 for EP Application No. 14866399.
Wang, et al. Autothermal oxidative coupling of methane on the $SrCO_3/Sm2\ O_3$ catalysts. Catalysis communications 10: 807-810, 2009.
Wang, et al. Comparative study on oxidation of methane to ethane and ethylene over NA2 WO4—Mn/SiO2 catalysts prepared by different methods. Journal of Molecular Catalysis A: Chemical 245:272-277, 2006.
Wang, et al., Critical Influence of BaC03 on Low Temperature Catalytic Activity of BaC03/Zr02 Catalysts for Oxidative Coupling of Methane, Catalysis Letters (2009), 129:156-162.
Wang, et al. Low temperature selective oxidation of methane to ethane and ethylene over $BaCO_3/La2\ O_3$ catalysts prepared by urea combustion method. Catalysis communications 7: 5963, 2006.
Water Electrolysis & Renewable Energy Systems. FuelCellToday (May 2013).
Wikipedia search, Adiabatic Process, Mar. 2011, 10 pages.
Witek-Krowiak, A. et al. Carbon Dioxide Removal in a Membrane Contactor-Selection of Absorptive Liquid/Membrane System. Intl J Chem Eng and Appl. (2012) 3(6):391-395.
Wong, et al. Oxidative coupling of methane over alkali metal oxide promoted La2 $O_3/BaCO_3$ cataylsts. J. Chem. Tech. Biotechnol. 65:351-354, 1996.
Xu, et al. Maximise ethylene gain and acetylene selective hydrogenation efficiency. Petroleum technology quarterly 18.3 (2013): 39-42.
Xu, G. et al. An Improved CO2 Separation and Purification System Based on Cryogenic Separation and Distillation Theory. Energies (2014) 7:3484-3502.
Yan, D. Modeling and Application of a Thermoelectric Generator. Thesis, Univ. Toronto (2011).
Yang, et al. Anistropic synthesis of boat shaped core shell Au—Ag nanocrystals and nanowires. Nanotechnology 17: 2304-2310, 2006.
Yu, et al. Oxidative coupling of methane over acceptor-doped SrTi $O_3$: Correlation between p-type conductivity and C2 selectivity and C2 yield. Journal of Catalysis. 13 (5): 338-344, 1992.
Zhang, Q. Journal of Natural Gas Chem., 12:81, 2003.
Zhao, et al. Technologies and catalysts for catalytic preparation of ethene. Industrial catalysis 12 (Supplement): 285-289, 2004.
Zhou. BP-UOP Cyclar Process. Handbook of Petroleum Refining Processes, The McGraw-Hill Companies (2004), pp. 2.29-2.38.
Zhou, et al. Functionalization of lanthanum hydroxide nanowires by atom transfer radical polymerization. Nanotechnology 18, 2007, 7 pages.
Zimmerman, et al. Ethylene. Ulmann's Encyclopedia of Inudstrial Chemisty, Wiley-VCH Verlag GmbH & Co. KGaA, Weinheim, Germany, 2009, 66 pages.
Co-pending U.S. Appl. No. 16/287,006, filed Feb. 27, 2019.
Co-pending U.S. Appl. No. 16/290,689, filed Mar. 1, 2019.
Co-pending U.S. Appl. No. 16/357,012, filed Mar. 18, 2019.
Duan, et al. Three-dimensional copper (II) metal-organic framework with open metal sites and anthracene nucleus for highly

(56) References Cited

OTHER PUBLICATIONS selective $C_2H_2/CH_4$ and $C_2H_2/CO_2$ gas separation at room temperature.Microporous and Mesoporous Materials. vol. 181, Nov. 15, 2013, pp. 99-104.

He, et al. A microporous metal-organic framework for highly selective separation of acetylene, ethylene, and ethane from methane at room temperature. Chemistry. Jan. 9, 2012;18(2):613-9. doi: 10.1002/chem.201102734. Epub Dec. 8, 2011.

EP13817389.3 Examination Report dated Feb. 13, 2019.

EP16855929.2 The Extended European Search Report dated Mar. 6, 2019.

U.S. Appl. No. 15/690,090 Office Action dated Mar. 15, 2019.

U.S. Appl. No. 15/699,798 Office Action dated Apr. 30, 2019.

Co-pending U.S. Appl. No. 16/442,135, filed Jun. 14, 2019 by Schammel, et al.

Co-pending U.S. Appl. No. 16/444,923, filed Jun. 18, 2019 by Jonnavittula, et al.

Co-pending U.S. Appl. No. 16/445,562, filed Jun. 19, 2019 by Duggal, et al.

Co-pending U.S. Appl. No. 16/509,279, filed Jul. 11, 2019 by Rafique, et al.

\* cited by examiner

| Fouling Resistance<br>Control Function | 1 | 2 | 3 | 4 |
|---|---|---|---|---|
| <1> Valve (steam pocketing middle section boiler) | closed | open | open | open |
| <2> Valve (steam pocketing far end section boiler) | closed | closed | open | open |
| <3a> T controller Exit Gas (acting on steam bypass) | active | active | active | off |
| <3b> T controller SuperHeat (acting on steam bypass) | active | active | active | off |
| <4> T controller acting on Exit Gas (BFW injection) | off | off | active | active |

*FIG. 26*

OXIDATIVE COUPLING OF METHANE FOR OLEFIN PRODUCTION

CROSS-REFERENCE

This application is a of U.S. patent application Ser. No. 15/487,181, filed Apr. 13, 2017, now U.S. Pat. No. 9,944,573, which claims priority to U.S. Provisional Patent Application Ser. No. 62/322,190, filed Apr. 13, 2016, U.S. Provisional Patent Application Ser. No. 62/341,307, filed May 25, 2016, U.S. Provisional Patent Application Ser. No. 62/341,308, filed May 25, 2016, U.S. Provisional Patent Application Ser. No. 62/379,675, filed Aug. 25, 2016, U.S. Provisional Patent Application Ser. No. 62/397,798, filed Sep. 21, 2016, and U.S. Provisional Patent Application Ser. No. 62/417,102, filed Nov. 3, 2016, each of which is entirely incorporated herein by reference.

BACKGROUND

There exists an infrastructure for chemical production throughout the world. This infrastructure is deployed on virtually every continent, addresses wide ranging industries, and employs a wide variety of different implementations of similar or widely differing technologies.

SUMMARY

The present disclosure provides systems and methods for reacting methane in an oxidative coupling of methane ("OCM") process to yield products comprising hydrocarbon compounds with two or more carbon atoms ("$C_{2+}$ compounds"), including propylene.

An aspect of the present disclosure provides a method for producing propylene, comprising: (a) directing methane ($CH_4$) and oxygen ($O_2$) into an oxidative coupling of methane (OCM) reactor that permits the $CH_4$ and the $O_2$ to react to yield an OCM product stream comprising hydrocarbon compounds with two or more carbon atoms ($C_{2+}$ compounds), including ethylene; (b) directing at least a portion of the OCM product stream into a separations unit that yields an ethylene stream comprising the ethylene from the OCM product stream; (c) directing at least a portion of the ethylene stream from the separations unit into a dimerization reactor that permits at least a portion of the ethylene to react in a dimerization reaction to yield a butene stream comprising one or more butene compounds; (d) directing at least a portion of the butene stream into a $C_4$ separations unit that yields a butene-2 stream comprising butene-2 from the at least a portion of the butene stream; and (e) directing at least a portion of the butene-2 stream and at least another portion of the ethylene stream into a metathesis reactor that permits at least a portion of the butene-2 and the ethylene to react to yield a metathesis product stream comprising higher hydrocarbon compounds, including the propylene.

In some embodiments, the method further comprises directing at least a portion of the metathesis product stream into a $C_2$ separations unit that separates the at least a portion of the metathesis product stream to at least a $C_2$ stream comprising hydrocarbon compounds with two carbon atoms ($C_2$ compounds) and a $C_{3+}$ stream comprising hydrocarbon compounds with three or more carbon atoms ($C_{3+}$ compounds), including at least a portion of the propylene. In some embodiments, the method further comprises directing the $C_2$ stream into the separations unit. In some embodiments, the method further comprises directing the $C_{3+}$ stream into a $C_3$ separations unit that separates the $C_{3+}$ stream to at least a $C_3$ stream comprising propylene and a $C_{4+}$ stream comprising hydrocarbon compounds with four or more carbon atoms ($C_{4+}$ compounds). In some embodiments, the method further comprises directing the $C_{4+}$ stream into the $C_4$ separations unit. In some embodiments, the method further comprises directing the propylene from the metathesis product stream into a polypropylene unit that permits the propylene to react to yield a polypropylene product stream comprising polypropylene. In some embodiments, the method further comprises directing at least a portion of the ethylene from the separations unit to the polypropylene unit, wherein the polypropylene unit reacts the at least a portion of the ethylene as a co-monomer with the propylene. In some embodiments, a molar ratio of ethylene co-monomer to total monomer and co-monomer is from about 0.01:0.99 to about 0.15:0.85. In some embodiments, the molar ratio of ethylene co-monomer to total monomer and co-monomer is from about 0.08:0.92 to about 0.15:0.85. In some embodiments, (a) further comprises directing ethane ($C_2H_6$) into the OCM reactor. In some embodiments, the method further comprises injecting olefins with five or more carbon atoms ($C_{5+}$ olefin) into one or more of the separations unit, the dimerization reactor, the $C_4$ separations unit, and the metathesis reactor. In some embodiments, the at least another portion of ethylene stream is a remainder of the ethylene stream.

Another aspect of the present disclosure provides a system for producing propylene, comprising: an oxidative coupling of methane (OCM) reactor that receives methane ($CH_4$) and oxygen ($O_2$) and permits the $CH_4$ and the $O_2$ to react to yield an OCM product stream comprising hydrocarbon compounds with two or more carbon atoms ($C_{2+}$ compounds), including ethylene; a separations unit that receives at least a portion of the OCM product stream and yields an ethylene stream comprising the ethylene from the OCM product stream; a dimerization reactor that receives at least a portion of the ethylene stream and permits at least a portion of the ethylene to react in a dimerization reaction to yield a butene stream comprising one or more butene compounds; a $C_4$ separations unit that receives at least a portion of the butene stream and yields a butene-2 stream comprising butene-2 from the at least a portion of the butene stream; and a metathesis reactor that receives at least a portion of the butene-2 stream and at least another portion of the ethylene stream and permits at least a portion of the butene-2 and the ethylene to yield a metathesis product stream comprising higher hydrocarbon compounds, including the propylene.

In some embodiments, the system further comprises a $C_2$ separations unit that receives at least a portion of the metathesis product stream and separates the at least a portion of the metathesis product stream to at least a $C_2$ stream comprising hydrocarbon compounds with two carbon atoms ($C_2$ compounds) and a $C_{3+}$ stream comprising hydrocarbon compounds with three or more carbon atoms ($C_{3+}$ compounds) including at least a portion of the propylene. In some embodiments, the separations unit receives the $C_2$ stream. In some embodiments, the system further comprises a $C_3$ separations unit that receives the $C_{3+}$ stream and separates the $C_{3+}$ stream to at least a $C_3$ stream comprising propylene and a $C_{4+}$ stream comprising hydrocarbon compounds with four or more carbon atoms ($C_{4+}$ compounds). In some embodiments, the $C_4$ separations unit receives the $C_{4+}$ stream. In some embodiments, the system further comprises a polypropylene unit that receives the propylene from the metathesis product stream and permits the propylene to react to yield a polypropylene product stream comprising polypropylene. In some embodiments, the polypropylene unit receives at least a portion of the ethylene from the separations unit and reacts the at least a portion of the ethylene as a co-monomer with the propylene. In some embodiments, a molar ratio of ethylene co-monomer to total monomer and co-monomer is from about 0.01:0.99 to about 0.15:0.85. In some embodiments, the molar ratio of ethylene co-monomer to total monomer and co-monomer is from about 0.08:0.92 to about 0.15:0.85. In some embodiments, the OCM reactor receives ethane ($C_2H_6$). In some embodiments, the at least another portion of the ethylene stream is a remainder of the ethylene stream.

Another aspect of the present disclosure provides a system for producing hydrocarbon compounds including propylene, comprising: an oxidative coupling of methane (OCM) reactor that receives methane ($CH_4$) and oxygen ($O_2$) and permits the $CH_4$ and the $O_2$ to react to yield an OCM product stream comprising hydrocarbon compounds with two or more carbon atoms ($C_{2+}$ compounds), including ethylene; a separations unit that receives at least a portion of the OCM product stream and yields an ethylene stream comprising the ethylene from the OCM product stream; a dimerization reactor that receives at least a portion of the ethylene stream and permits at least a portion of the ethylene to react in a dimerization reaction to yield a butene stream comprising one or more butene compounds; and a metathesis reactor that receives at least another portion of the ethylene stream and at least a portion of the butene stream and permits at least a portion of the one or more butane compounds and at least another portion of the ethylene to react to produce a product stream comprising the propylene.

In some embodiments, the metathesis reactor receives an external $C_4$ stream comprising hydrocarbon compounds with four carbon atoms, wherein the $C_4$ stream replaces at least a portion of the butane stream from the dimerization unit. In some embodiments, the metathesis reactor is configured to (i) produce only ethylene as the final product, (ii) utilize the dimerization reactor to produce butenes as the final product, (iii) produce propylene as a final product, or (iv) use the propylene to produce polypropylene. In some embodiments, the product stream comprises polymer grade ethylene, polymer grade propylene, chemical grade ethylene, chemical grade propylene, polypropylene, a mixture of butenes, or combinations thereof. In some embodiments, the at least another portion of ethylene is a remainder of the ethylene from the ethylene stream.

Another aspect of the present disclosure provides a system for producing mixed butenes, comprising an oxidative coupling of methane (OCM) reactor, a dimerization reactor in fluid communication with the OCM reactor, and a recovery system in fluid communication with the dimerization reactor, which recovery system is for recovering mixed butenes.

In some embodiments, the mixed butenes comprise at least about 50% butene-2. In some embodiments, the mixed butenes comprise at least about 90% butene-2. In some embodiments, the mixed butenes comprise at least about 99% butene-2.

Another aspect of the present disclosure provides a system for producing butene-1, comprising an oxidative coupling of methane (OCM) reactor, a dimerization reactor in fluid communication with the OCM reactor, and a recovery unit in fluid communication with the dimerization reactor, which recovery unit recovers the butene-1.

Another aspect of the present disclosure provides a method for producing butene-1, comprising: (a) directing methane ($CH_4$) and oxygen ($O_2$) into an oxidative coupling of methane (OCM) reactor that permits the $CH_4$ and the $O_2$ to react to yield an OCM product stream comprising hydrocarbon compounds with two or more carbon atoms ($C_{2+}$ compounds), including ethylene; (b) directing at least a portion of the OCM product stream into a dimerization reactor that permits at least a portion of the ethylene to react to produce a dimerization product stream comprising the butene-1; and (c) directing the dimerization product stream into a separations unit that produces a first stream containing un-reacted ethylene and a second stream containing the butene-1.

In some embodiments, the method further comprises recycling the un-reacted ethylene to the dimerization reactor. In some embodiments, the method further comprises reacting the butene-1 with ethylene to produce low linear density polyethylene (LLDPE). In some embodiments, the dimerization reactor contains a catalyst containing titanium.

Another aspect of the present disclosure provides a method for producing butene-2, comprising: (a) directing methane ($CH_4$) and oxygen ($O_2$) into an oxidative coupling of methane (OCM) reactor that permits the $CH_4$ and the $O_2$ to react to yield an OCM product stream comprising hydrocarbon compounds with two or more carbon atoms ($C_{2+}$ compounds), including ethylene; (b) directing at least a portion of the OCM product steam into a dimerization reactor that permits at least a portion of the ethylene to react to produce a dimerization product stream comprising butene-1; and (c) directing the dimerization product stream into a hydroisomerization reactor that converts the butene-1 to the butene-2.

In some embodiments, the method further comprises directing the butene-2 and at least a portion of the ethylene to a metathesis reactor to produce propylene. In some embodiments, the method further comprises recycling un-reacted ethylene to the dimerization reactor.

Another aspect of the present disclosure provides a system for producing butadiene, comprising an oxidative coupling of methane (OCM) reactor, a dimerization reactor in fluid communication with the OCM reactor, and a $C_4$ dehydrogenation unit in fluid communication with the dimerization reactor.

Another aspect of the present disclosure provides a method for producing butadiene, comprising: (a) directing methane ($CH_4$) and oxygen ($O_2$) into an oxidative coupling of methane (OCM) reactor that permits the $CH_4$ and the $O_2$ to react to yield an OCM product stream comprising hydrocarbon compounds with two or more carbon atoms ($C_{2+}$ compounds), including ethylene; (b) directing at least a portion of the OCM product stream into a dimerization reactor that permits at least a portion of the ethylene to react to produce a dimerization product stream comprising butene-1; and (c) directing the dimerization product stream into a $C_4$ dehydrogenation reactor that converts the butene-1 to the butadiene.

Another aspect of the present disclosure provides a method for performing an oxidative coupling of methane (OCM) reaction, comprising: (a) heating a first stream comprising methane ($CH_4$) to a first temperature; (b) heating a second stream comprising oxygen ($O_2$) to a second temperature, which second temperature is less than the first temperature; and (c) mixing the first stream and the second stream to produce a third stream, which third stream is contacted with an OCM catalyst to perform an OCM reaction.

In some embodiments, the first stream is natural gas. In some embodiments, the second stream is air. In some embodiments, the first stream and second stream are mixed in (c) prior to performing the OCM reaction. In some embodiments, portions of the third stream having a higher concentration of $O_2$ have a lower initial temperature when the second temperature is lower than the third temperature, and a maximum temperature of the OCM reaction in (c) is reduced when the first stream and the second stream is perfectly mixed and/or the second temperature is substantially equal to the third temperature. In some embodiments, the heat capacity of the second stream is at least about 30% of the heat capacity of the third stream. In some embodiments, a difference between the first temperature and the second temperature is at least about 20° C. In some embodiments, the first temperature is at most about 550° C. when the first stream comprises greater than about 5 mol % hydrocarbon compounds with two or more carbon atoms ($C_{2+}$ compounds). In some embodiments, the first temperature is at most about 600° C. when the first stream comprises less than about 5 mol % hydrocarbon compounds with two or more carbon atoms ($C_{2+}$ compounds).

Another aspect of the present disclosure provides a method for performing an oxidative coupling of methane (OCM) reaction, comprising: (a) heating a first stream comprising oxygen ($O_2$) to a first temperature; (b) dividing a second stream comprising methane ($CH_4$) into at least two portions and heating each of the at least two portions to a different temperature; (c) directing the each of the at least two portions of the second stream into a different area of a mixer, which mixer mixes the $CH_4$ with the first stream to generate mixtures; and (d) contacting the mixtures generated in (c) with an OCM catalyst bed to perform the OCM reaction.

In some embodiments, the first stream is air. In some embodiments, the second stream is natural gas. In some embodiments, areas of the mixer into which the at least two portions of the second stream are directed in (c) are selected to reduce a maximum temperature of the OCM catalyst bed during the reaction in (d). In some embodiments, areas of the mixer into which the at least two portions of the second stream are directed in (c) are selected to bypass a portion of the $O_2$ further into the OCM catalyst bed.

Another aspect of the present disclosure provides a method for performing an oxidative coupling of methane (OCM) reaction, comprising: (a) heating a first stream comprising methane ($CH_4$) to a first temperature; (b) dividing a second stream comprising oxygen ($O_2$) into at least two portions and heating each of the at least two portions to a different temperature; (c) directing the each of the at least two portions of the second stream into a different area of a mixer, which mixer mixes the $O_2$ with the first stream; and (d) contacting the mixtures produced in (c) with an OCM catalyst bed to perform the OCM reaction.

In some embodiments, the first stream is natural gas. In some embodiments, the second stream is air. In some embodiments, areas of the mixer into which the at least two portions of the second stream are directed in (c) are selected to reduce a maximum temperature of the OCM catalyst bed during the reaction in (d). In some embodiments, areas of the mixer into which the at least two portions of the second stream are directed in (c) are selected to bypass a portion of the $O_2$ further into the OCM catalyst bed.

Another aspect of the present disclosure provides a method for performing an oxidative coupling of methane (OCM) reaction, comprising: (a) providing a first stream comprising methane ($CH_4$) at a first temperature; (b) providing a second stream comprising oxygen ($O_2$) at a second temperature; and (c) alternately directing the first stream and the second stream into an OCM reactor that comprises an OCM catalyst to perform the OCM reaction.

In some embodiments, the second temperature is less than the first temperature. In some embodiments, the first stream and the second stream are alternated at a frequency that is varied in response to a temperature measured in the OCM reactor. In some embodiments, less $O_2$ is directed into the OCM reactor when the temperature in the OCM reactor approaches a maximum temperature. In some embodiments, the frequency is between about 0.1 and about 10 hertz (Hz). In some embodiments, (c) is performed with piezo-electric injectors.

Another aspect of the present disclosure provides a method for performing an oxidative coupling of methane (OCM) reaction, the method comprising: (a) providing a first stream comprising methane ($CH_4$) and oxygen ($O_2$) at a first temperature; (b) providing a second stream comprising $CH_4$ at a second temperature; and (c) alternately directing the first stream and the second stream into an OCM reactor which comprises an OCM catalyst to perform an OCM reaction. In some embodiments, the second stream further comprises $O_2$.

Another aspect of the present disclosure provides a method for performing an oxidative coupling of methane (OCM) reaction, comprising: (a) directing a first portion of methane ($CH_4$) and a first portion of oxygen ($O_2$) into a first OCM reactor, wherein the first OCM reactor is an adiabatic reactor; (b) in the first OCM reactor, producing a first product stream comprising hydrocarbon compounds with two or more carbon atoms ($C_{2+}$ compounds) and liberating a first portion of heat, which first portion of heat increases the temperature of the first product stream; (c) directing a second portion of $CH_4$ and a second portion of oxygen $O_2$ into a second OCM reactor, wherein the second OCM reactor is an isothermal reactor; (d) in the second OCM reactor, producing a second product stream comprising hydrocarbon compounds with two or more carbon atoms ($C_{2+}$ compounds) and liberating a second portion of heat, which second portion of heat is removed from the second OCM reactor; and (e) combining the second product stream with the first product stream, wherein the first portion of heat aids in converting ethane ($C_2H_6$) in the first and/or second product streams into ethylene ($C_2H_4$).

In some embodiments, the method further comprises (i) adding $C_2H_6$ to the first product stream, and (ii) converting the $C_2H_6$ added in (i) into $C_2H_4$. In some embodiments, the method further comprises (i) adding $C_2H_6$ to the combined stream in (e), and (ii) converting the $C_2H_6$ added in (i) into $C_2H_4$. In some embodiments, the second OCM reactor is a tubular reactor. In some embodiments, the second OCM reactor is a fluidized bed reactor. In some embodiments, the first portion of heat increases the temperature of the first product stream to at least about 800° C. In some embodiments, the second portion of heat is removed from the second OCM reactor such that the temperature of the second product stream is less than about 800° C. In some embodiments, the first OCM reactor converts between about 10% and about 13% of the first portion of $CH_4$ into $C_{2+}$ compounds. In some embodiments, the first OCM reactor converts the first portion of $CH_4$ into $C_{2+}$ compounds with a $C_{2+}$ selectivity from about 55% to about 65%. In some embodiments, the first OCM reactor has a $C_{2+}$ yield from about 6% to about 9%. In some embodiments, the second OCM reactor converts between about 20% and about 22% of the second portion of $CH_4$ into $C_{2+}$ compounds. In some embodiments, the second OCM reactor converts the second portion of $CH_4$ into $C_{2+}$ compounds with a $C_{2+}$ selectivity from about 60% to about 70%. In some embodiments, the second reactor has a $C_{2+}$ yield from about 12% to about 15%. In some embodiments, the first OCM reactor comprises a reaction zone comprising an OCM catalyst and a post-bed cracking zone in which (e) is performed. In some embodiments, a ratio of the amount of second product stream to the amount of first product stream in (e) is such that a temperature of the combined stream is reduced below about 400° C. following conversion of $C_2H_6$ into $C_2H_4$.

Another aspect of the present disclosure provides an apparatus for exchanging heat, the apparatus comprising: a first chamber and a second chamber; a plurality of tubes configured to contain a process fluid that flows from an inlet in the first chamber to an exit of the second chamber, passing through the first chamber and the second chamber; and a steam drum configured to contain a liquid phase and a gas phase of a cooling fluid, wherein (i) the steam drum is in fluidic communication with the first chamber such that the liquid phase of the cooling fluid is contacted with an exterior of the plurality of tubes in the first chamber to boil the cooling fluid using heat derived from the process fluid, and (ii) the steam drum is in fluidic communication with the second chamber such that the gas phase of the cooling fluid is contacted with an exterior of the plurality of tubes in the second chamber to super-heat the cooling fluid using heat derived from the process fluid.

In some embodiments, the boiled cooling fluid is returned from the first chamber to the steam drum. In some embodiments, the super-heated cooling fluid is used to provide energy to a chemical process. In some embodiments, the first chamber shares a wall with the second chamber. In some embodiments, each of the plurality of tubes comprises a first tube adjoined to a second tube to provide a continuous conduit for the process fluid. In some embodiments, the first tube passes through the first chamber and the second tube passes through the second chamber, and the first chamber is adjoined to the second chamber. In some embodiments, leakage of the cooling fluid from the first chamber to the second chamber is prevented by a seal, by bonding, welding, or brazing the first chamber to the second chamber, and/or by expanding each of the plurality of tubes in a joint. In some embodiments, the apparatus does not comprise a cross-over duct between the first chamber and the second chamber. In some embodiments, the first chamber comprises at least one of (a) a down-comer connected to the steam drum to distribute the cooling fluid over the exterior of the plurality of tubes, (b) a riser connected to the steam drum to collect the cooling fluid, and (c) a baffle that supports the plurality of tubes and/or guides the cooling fluid from the down-comer to the riser. In some embodiments, the apparatus comprises (a), (b) and (c). In some embodiments, the apparatus comprises a plurality of down-comers, and each down-comer is controlled by a valve, which valves are capable of modulating an amount of the cooling fluid that is boiled in the first chamber. In some embodiments, the second chamber comprises a plurality of baffles that supports the plurality of tubes and/or directs the cooling fluid over the exterior of the plurality of tubes. In some embodiments, the apparatus further comprises an atomizer for adding an aerosol of the cooling fluid to the gas phase of the cooling fluid prior to flowing into the second chamber, which atomizer is controlled by a valve that is capable of modulating an amount of the cooling fluid that is super-heated in the second chamber. In some embodiments, the apparatus further comprises a valve that is capable of modulating an amount of the gas phase of the cooling fluid that is withdrawn from the steam drum, which valve is capable of modulating an amount of the super-heated cooling fluid that is produced. In some embodiments, the cooling fluid flows substantially perpendicularly with respect to the process fluid in the first chamber. In some embodiments, the cooling fluid flows substantially co-currently with the process fluid in the second chamber. In some embodiments, the process fluid is a hot gas. In some embodiments, the cooling fluid is water. In some embodiments, the first chamber is a fire-tube boiler. In some embodiments, the second chamber is a fire-tube steam superheater. In some embodiments, the apparatus further comprises a valve, obstruction, or one or more other units capable of controlling the number of tubes through which the process fluid flows.

Another aspect of the present disclosure provides a method for exchanging heat, the method comprising: (a) providing a heat exchanger comprising a first chamber and a second chamber; (b) flowing a process fluid into the first chamber at an initial temperature; (c) in the first chamber, decreasing the initial temperature of the process fluid to an intermediate temperature by boiling a first quantity of a cooling fluid using a first quantity of heat derived from the process fluid; (d) flowing the process fluid into the second chamber at the intermediate temperature; and (e) in the second chamber, further decreasing the intermediate temperature of the process fluid to an exit temperature to a target temperature by super-heating the boiled cooling fluid from (b) using a second quantity of heat derived from the process fluid, wherein no more than about 100 milliseconds (ms) of time passes between the process fluid reaching the intermediate temperature and initiation of super-heating the boiled cooling fluid.

In some embodiments, no more than about 50 milliseconds (ms) of time passes between the process fluid reaching the intermediate temperature and initiation of super-heating the boiled cooling fluid. In some embodiments, no more than about 10 milliseconds (ms) of time passes between the process fluid reaching the intermediate temperature and initiation of super-heating the boiled cooling fluid. In some embodiments, the first chamber and the second chamber share a wall. In some embodiments, the heat exchanger is operated for at least about 6 months without cleaning. In some embodiments, a second quantity of the cooling fluid in thermal communication with the process fluid in (c) is not boiled. In some embodiments, the method further comprises, when the exit temperature is lower than the target temperature, decreasing the first quantity of the cooling fluid that is boiled, thereby increasing the exit temperature to the target temperature. In some embodiments, the exit temperature is less than the target temperature because the heat exchanger is not fouled. In some embodiments, the method further comprises, when the exit temperature is greater than the target temperature, increasing the first quantity of the cooling fluid that is boiled, thereby decreasing the exit temperature to the target temperature. In some embodiments, the exit temperature is greater than the target temperature because the heat exchanger is fouled. In some embodiments, the cooling fluid is super-heated to at least about 500° C. In some embodiments, a temperature of the process fluid is decreased from the initial temperature to the target temperature within about 250 milliseconds (ms).

Another aspect of the present disclosure provides an oxidative coupling of methane (OCM) system, comprising: an OCM subsystem that (i) takes as input a first feed stream comprising methane ($CH_4$) and a second feed stream comprising an oxidizing agent, and (ii) generates from the methane and the oxidizing agent a product stream comprising compounds with two or more carbon atoms ($C_{2+}$ compounds); and a dual compartment heat exchanger downstream of, and fluidically coupled to, the OCM subsystem, the dual compartment heat exchanger comprising a first compartment and a second compartment, wherein a temperature of the product stream entering an inlet of the first compartment is reduced to a target temperature at an outlet of the second compartment, and wherein: (1) the first compartment comprises (i) a first plurality of tubes to direct the process stream through the first compartment, (ii) a first plurality of baffles, and (iii) a plurality of down-comer pipes, wherein the plurality of down-comer pipes is fluidically coupled to a steam drum configured to generate a saturated steam; and (2) the second compartment comprises (i) a second plurality of tubes fluidically coupled to the first plurality of tubes, and (ii) a second plurality of baffles, wherein the second plurality of baffles is configured to direct the saturated steam in substantially co-current flow with the product stream.

In some embodiments, the dual compartment heat exchanger further comprises a tube sheet positioned between the first compartment and the second compartment. In some embodiments, the tube sheet is positioned substantially perpendicularly with respect to the first plurality of tubes and the second plurality of tubes. In some embodiments, the tube sheet comprises one or more cavities. In some embodiments, the dual compartment heat exchanger does not comprise a cross-over duct. In some embodiments, the first compartment is at least about 4 meters in length. In some embodiments, the second compartment is at least about 6 meters in length. In some embodiments, the target temperature is less than or equal to about 500° C. In some embodiments, when the system comprises a process fouling resistance less than or equal to about 0.003 meters squared Kelvin per Watts ($m^2$ K/W), the product stream exiting the outlet of the second compartment reaches the target temperature. In some embodiments, the OCM subsystem comprises a post-bed cracking unit.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also referred to herein as "FIG." and "FIGS."), of which:

FIG. 26 is a table of control functions in relation to process fouling resistance;

DETAILED DESCRIPTION

Figure 1:
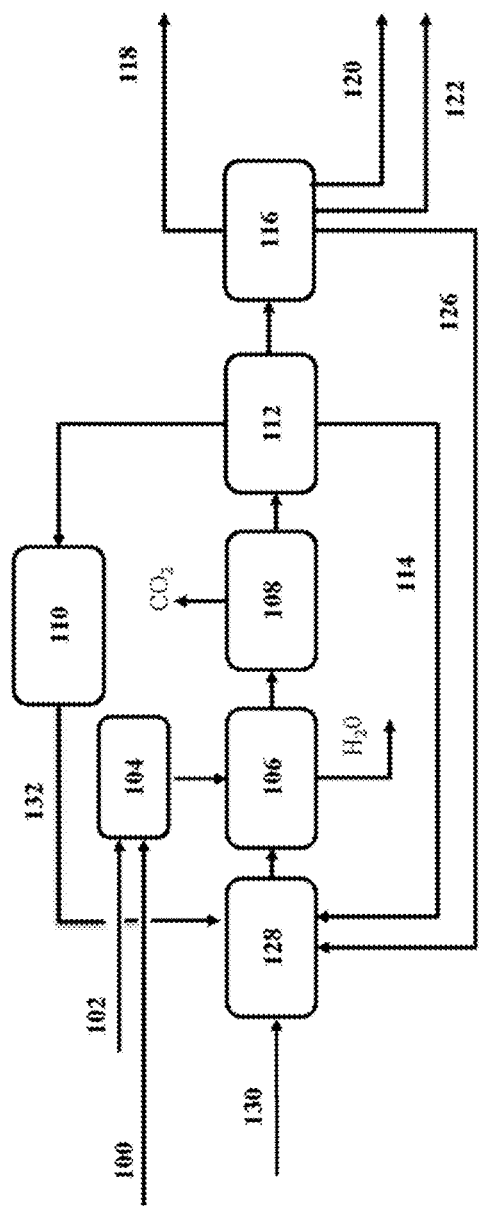
FIG. 1 is a schematic illustration of an example oxidative coupling of methane (OCM) process.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "higher hydrocarbon," as used herein, generally refers to a higher molecular weight and/or higher chain hydrocarbon. A higher hydrocarbon can have a higher molecular weight and/or carbon content that is higher or larger relative to starting material in a given process (e.g., OCM or ETL). A higher hydrocarbon can be a higher molecular weight and/or chain hydrocarbon product that is generated in an OCM or ETL process. For example, ethylene is a higher hydrocarbon product relative to methane in an OCM process. As another example, a $C_{3+}$ hydrocarbon is a higher hydrocarbon relative to ethylene in an ETL process. As another example, a $C_{5+}$ hydrocarbon is a higher hydrocarbon relative to ethylene in an ETL process. In some cases, a higher hydrocarbon is a higher molecular weight hydrocarbon.

The term "OCM process," as used herein, generally refers to a process that employs or substantially employs an oxidative coupling of methane (OCM) reaction. An OCM reaction can include the oxidation of methane to a higher hydrocarbon and water, and involves an exothermic reaction. In an OCM reaction, methane can be partially oxidized and coupled to form one or more $C_{2+}$ compounds, such as ethylene. In an example, an OCM reaction is $2CH_4 + O_2 \rightarrow C_2H_4 + 2H_2O$. An OCM reaction can yield $C_{2+}$ compounds. An OCM reaction can be facilitated by a catalyst, such as a heterogeneous catalyst. Additional by-products of OCM reactions can include CO, $CO_2$, $H_2$, as well as hydrocarbons, such as, for example, ethane, propane, propene, butane, butene, and the like.

The term "non-OCM process," as used herein, generally refers to a process that does not employ or substantially employ an oxidative coupling of methane reaction. Examples of processes that may be non-OCM processes include non-OCM hydrocarbon processes, such as, for example, non-OCM processes employed in hydrocarbon processing in oil refineries, a natural gas liquids separations processes, steam cracking of ethane, steam cracking or naphtha, Fischer-Tropsch processes, and the like.

The terms "$C_{2+}$" and "$C_{2+}$ compound," as used herein, generally refer to a compound comprising two or more carbon atoms. For example, $C_{2+}$ compounds include, without limitation, alkanes, alkenes, alkynes and aromatics containing two or more carbon atoms. $C_{2+}$ compounds can include aldehydes, ketones, esters and carboxylic acids. Examples of $C_{2+}$ compounds include ethane, ethene, acetylene, propane, propene, butane, and butene.

The term "non-$C_{2+}$ impurities," as used herein, generally refers to material that does not include $C_{2+}$ compounds. Examples of non-$C_{2+}$ impurities, which may be found in certain OCM reaction product streams, include nitrogen ($N_2$), oxygen ($O_2$), water ($H_2O$), argon (Ar), hydrogen ($H_2$) carbon monoxide (CO), carbon dioxide ($CO_2$) and methane ($CH_4$).

The term "small scale," as used herein, generally refers to a system that generates less than or equal to about 250 kilotons per annum (KTA) of a given product, such as an olefin (e.g., ethylene).

The term "world scale," as used herein, generally refers to a system that generates greater than about 250 KTA of a given product, such as an olefin (e.g., ethylene). In some examples, a world scale olefin system generates at least about 1000, 1100, 1200, 1300, 1400, 1500, or 1600 KTA of an olefin.

The term "item of value," as used herein, generally refers to money, credit, a good or commodity (e.g., hydrocarbon). An item of value can be traded for another item of value.

The term "carbon efficiency," as used herein, generally refers to the ratio of the number of moles of carbon present in all process input streams (in some cases including all hydrocarbon feedstocks, such as, e.g., natural gas and ethane and fuel streams) to the number of moles of carbon present in all commercially (or industrially) usable or marketable products of the process. Such products can include hydrocarbons that can be employed for various downstream uses, such as petrochemical or for use as commodity chemicals. Such products can exclude CO and $CO_2$. The products of the process can be marketable products, such as $C_{2+}$ hydrocarbon products containing at least about 99% $C_{2+}$ hydrocarbons and all sales gas or pipeline gas products containing at least about 90% methane. Process input streams can include input streams providing power for the operation of the process, such as with the aid of a turbine (e.g., steam turbine). In some cases, power for the operation of the process can be provided by heat liberated by an OCM reaction.

The term "nitrogen efficiency," as used herein, generally refers to the ratio of the number of moles of nitrogen present in all process input streams (in some cases including all nitrogen feedstocks, such as, e.g., air or purified nitrogen) to the number of moles of nitrogen present in all commercially (or industrially) usable or marketable products of the process. Such products can include ammonia and other nitrogen products that can be employed for various downstream uses, such as petrochemical use, agricultural use, or for use as commodity chemicals. Such products can exclude nitrogen oxides (NOx), such as NO and $NO_2$. The products of the process can be marketable products, such as ammonia and derivatives thereof containing at least about 90% or 99% ammonia or ammonia derivatives. Process input streams can include input streams providing power for the operation of the process, such as with the aid of a turbine (e.g., steam turbine). In some cases, power for the operation of the process can be provided by heat liberated by a reaction, such as an OCM reaction.

The term "$C_{2+}$ selectivity," as used herein, generally refers to the percentage of the moles of methane that are converted into $C_{2+}$ compounds.

The term "$C_{2+}$ yield," as used herein, generally refers to the amount of carbon that is incorporated into a $C_{2+}$ product as a percentage of the amount of carbon introduced into a reactor in the form of methane. This may generally be calculated as the product of the conversion and the selectivity divided by the number of carbon atoms in the desired product. $C_{2+}$ yield is typically additive of the yield of the different $C_{2+}$ components included in the $C_{2+}$ components identified, e.g., ethane yield+ethylene yield+propane yield+propylene yield etc.).

The term "specific oxygen consumption," as used herein, generally refers to the mass (or weight) of oxygen consumed by a process divided by the mass of $C_{2+}$ compounds produced by the process.

The term "specific $CO_2$ emission," as used herein, generally refers to the mass of $CO_2$ emitted from the process divided by the mass of $C_{2+}$ compounds produced by the process.

The term "unit," as used herein, generally refers to a unit operation. A unit operation may be one or more basic steps in a process. A unit may have one or more sub-units (or sub-systems). Unit operations may involve a physical change or chemical transformation, such as separation, crystallization, evaporation, filtration, polymerization, isomerization, and other reactions. A unit may include one or more individual components. For example, a separations unit may include one or more separations columns or an amine unit may include one or more amine columns.

The term "methane conversion," as used herein, generally refers to the percentage or fraction of methane introduced into the reaction that is converted to a product other than methane.

The term "airfoil" (or "aerofoil" or "airfoil section"), as used herein, generally refers to the cross-sectional shape of a blade. A blade may have one or more airfoils. In an example, a blade has a cross-section that is constant along a span of the blade, and the blade has one airfoil. In another example, a blade has a cross-section that varies along a span of the blade, and the blade has a plurality of airfoils.

The term "auto-ignition" or "autoignition," as used herein in the context of temperature, generally refers to the lowest temperature at which a substance, given sufficient time, will spontaneously ignite without an external source of ignition, such as a flame or spark. Use of the term "auto-ignites" with reference to oxygen refers to the amount of oxygen that reacts with (e.g., combustion reaction) any or all hydrocarbons that are mixed with oxygen (e.g., methane).

The term "substantially equivalent," as used herein in the context of methane concentration, generally means that the methane concentration is within approximately plus or minus 80%, 70%, 60%, 50%, 40%, or 30%, and preferably within plus or minus 20%, 10%, 5%, or less of the methane concentration that may be passed into an existing fractionation train of a gas facility or cracker facility.

The term "quench," as used herein, generally refers to rapid cooling or reducing of the temperature of a process stream, such as a process gas. The rapid cooling may be performed by a system component, such as a heat exchanger. Quenching may prevent undesired reactions low-temperature processes from occurring.

The term "fouling," as used herein, generally refers to the accumulation of unwanted material(s) on a surface of a component of a system, such as an inner surface of a heat exchanger. Fouling may cause altered function to the heat exchanger. Fouling may impede or interfere with the function of the heat exchanger. Fouling may include precipitation fouling, particulate fouling, corrosion fouling, chemical reaction fouling, solidification fouling, biofouling, composite fouling, or any combination thereof. Heavily fouled systems may need to be cleaned to remove the fouling layer from the surface of the system component.

OCM Processes

In an OCM process, methane ($CH_4$) may react with an oxidizing agent over a catalyst bed to generate $C_{2+}$ compounds. For example, methane can react with oxygen over a suitable catalyst to generate ethylene, e.g., $2CH_4 + O_2 \rightarrow C_2H_4 + 2 H_2O$ (See, e.g., Zhang, Q., *Journal of Natural Gas Chem.*, 12:81, 2003; Olah, G. "Hydrocarbon Chemistry", Ed. 2, John Wiley & Sons (2003)). This reaction may be exothermic ($\Delta H=-280$ kJ/mol) and occur at very high temperatures (e.g., >450° C. or >700° C.). Non-selective reactions that can occur include (a) $CH_4 + 2O_2 \rightarrow CO_2 + 2H_2O$ and (b) $CH_4 + \frac{1}{2}O_2 \rightarrow CO + 2H_2$. These non-selective reactions may also be exothermic, with reaction heats of -891 kJ/mol and -36 kJ/mol respectively. The conversion of methane to COx products may be undesirable due to both heat management and carbon efficiency concerns.

Experimental evidence suggests that free radical chemistry may be involved. (Lunsford, *J. Chem. Soc., Chem. Comm.*, 1991; H. Lunsford, *Angew. Chem., Int. Ed. Engl.*, 34:970, 1995). In the reaction, methane ($CH_4$) may be activated on the catalyst surface, forming methyl radicals which then couple on the surface or in the gas phase to form ethane ($C_2H_6$), followed by dehydrogenation to ethylene ($C_2H_4$). The OCM reaction pathway can have a heterogeneous/homogeneous mechanism, which involves free radical chemistry. Experimental evidence has shown that an oxygen active site on the catalyst activates the methane, removes a single hydrogen atom and creates a methyl radical. Methyl radicals may react in the gas phase to produce ethane, which may be either oxidative or non-oxidatively dehydrogenated to ethylene. The main reactions in this pathway can be as follows: (a) $CH_4 + O^- \rightarrow CH_3^* + OH^-$; (b) $2 CH_3^* \rightarrow C_2H_6$; (c) $C_2H_6 + O \rightarrow C_2H_4 + H_2O$. In some cases, to improve the reaction yield, ethane can be introduced downstream of the OCM catalyst bed and thermally dehydrogenated via the following reaction: $C_2H_6 \rightarrow C_2H_4 + H_2$. This reaction is endothermic ($\Delta H=144$ kJ/mol), which can utilize the exothermic reaction heat produced during methane conversion. Combining these two reactions in one vessel can increase thermal efficiency while simplifying the process.

Catalysts for OCM, may include, e.g., various forms of iron oxide, $V_2O_5$, $MoO_3$, $Co_3O_4$, Pt—Rh, $Li/ZrO_2$, Ag—Au, $Au/Co_3O_4$, Co/Mn, $CeO_2$, MgO, $La_2O_3$, $Mn_3O_4$, $Na_2WO_4$, MnO, ZnO, and/or combinations thereof, on various supports. A number of doping elements may be used in combination with the above-mentioned catalysts.

Various limitations of the conventional approach to C—H bond activation may limit the yield of OCM reaction under practical operating conditions. For example, publications from industrial and academic labs have shown characteristic performance of high selectivity at low conversion of methane, or low selectivity at high conversion (J. A. Labinger, Cat. Lett., 1:371, 1988). Limited by this conversion/selectivity threshold, no OCM catalyst has been able to exceed 20-25% combined $C_2$ yield (i.e., ethane and ethylene). In addition, almost all such reported yields required extremely high reactor inlet temperatures (>800° C.). Catalysts and processes adapted for performing OCM reaction at substantially more practicable temperatures, pressures and catalyst activities have been described in U.S. Patent Publication Nos. 2012/0041246, 2013/0023709, 2013/0165728, 2013/0158322, 2014/0121433, 2014/0274671, and 2015/0314267, each of which is incorporated herein by reference in its entirety for all purposes.

An OCM reactor can include a catalyst that facilitates an OCM process. The catalyst may include a compound including at least one of an alkali metal, an alkaline earth metal, a transition metal, and a rare-earth metal. The catalyst may be in the form of a honeycomb, packed bed, or fluidized bed. In some embodiments, at least a portion of the OCM catalyst in at least a portion of the OCM reactor can include one or more OCM catalysts and/or nanostructure-based OCM catalyst compositions, forms and formulations. Examples of OCM reactors, separations for OCM, and OCM process designs are described in U.S. Patent Publication Nos. 2013/0225884, 2014/0107385, 2014/0012053, and 2015/0152025, each of which is incorporated herein by reference in its entirety for all purposes. An OCM reactor can be adiabatic or substantially adiabatic (including, for example, a post-bed cracking unit). An OCM reactor can be isothermal or substantially isothermal.

With reference to FIG. 1, natural gas 100 and ethane 102 can enter the process through a de-sulfurization module (or unit) 104, which can flow into a process gas compression module 106 where water can be removed. OCM product gas can be added to the process gas compression module 106 as well. A process gas cleanup module 108 can remove carbon dioxide ($CO_2$), some or all of which can be taken to a methanation module 110. Following cleanup, the process gas can flow into a first separations module 112 that removes $C_{2+}$ compounds from the process gas stream. The remaining process gas can flow to the methanation module 110 and/or a fired heater (e.g., to heat incoming OCM gas streams 114). The $C_{2+}$ compounds can be fractionated in a second separations module 116 to produce ethylene ($C_2H_4$) 118, $C_3$ compounds 120, and $C_{4+}$ compounds 122 for example. The second separations module 116 can produce an ethane ($C_2H_6$) stream 126 that can be returned to the OCM reactor 128. At the OCM reactor 128, oxygen 130 can be reacted with methane from the methanation module 132. Outside boundary limits (OSBL) systems may include a steam system, a boiler feed water system and a cooling water system.

Figure 2:
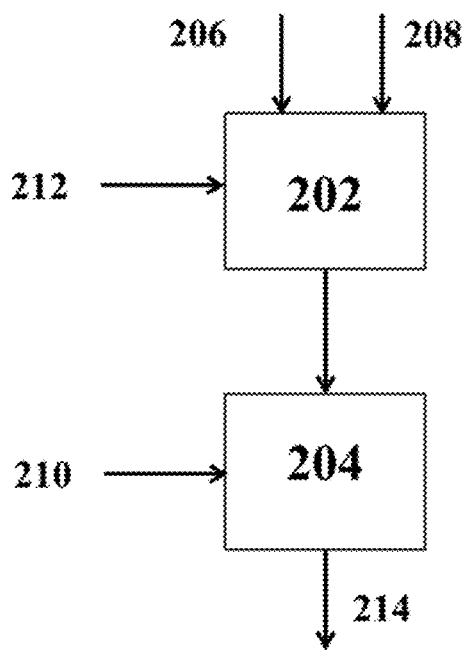
FIG. 2 is a schematic illustration of addition of ethane to an example OCM reactor.

The OCM reactor can perform the OCM reaction and a post-bed cracking (PBC) reaction, as described in U.S. Patent Publication No. 2015/0152025, which is incorporated herein by reference in its entirety. With reference to FIG. 2, the OCM reactor 200 can have an OCM reaction section 202 and a PBC section 204. Methane 206 (e.g., from natural gas) and oxygen 208 can be injected (via a mixer) into the OCM reaction region (which comprises an OCM catalyst). The OCM reaction may be exothermic and the heat of reaction can be used to crack additional ethane 210 that can be injected into the PBC region 204. In some cases, yet more ethane 212 can also be injected into the OCM reaction region 202 and/or the methane feed is supplemented with ethane or other $C_{2+}$ alkanes (e.g., propane or butane). The OCM reactor may produce an OCM effluent 214.

The relative amounts of supplemental ethane 210 and 212 can be varied to achieve a range of product outcomes from the system. In some cases, no ethane is injected into the OCM reaction region 202 (referred to herein as Case-1). Another example presented herein has 3.5 mol % ethane injected into the OCM region (referred to herein as Case-2). Some process design results are presented in Table 1.

TABLE 1

Examples of various amounts of ethane in OCM feed

|  | Case-1 | Case-2 |
|---|---|---|
| Natural gas consumed (MMSCFD) | 15.5 | 16 |
| Ethane consumed (MMSCFD) | 2.2 | 8.3 |
| [Ethane] at inlet (mol %) | 0.07 | 3.5 |
| [Ethylene] at outlet (mol %) | 3.6 | 4.9 |
| $C_2$ products (kTa) | 85 | 115 |
| $C_3$ products (kTa) | 10.3 | 21.1 |
| $C_{4+}$ products (kTa) | 2.7 | 2.5 |
| $O_2$ consumed (ton/ton ethylene) | 2.2 | 1.8 |
| $CO_2$ produced from OCM (ton/ton ethylene) | 0.9 | 0.7 |
| $CO_2$ produced from fired heater (ton/ton ethylene) | 0.6 | 0.4 |

In some cases, an amount of hydrogen ($H_2$) exiting the OCM reactor is relatively higher for cases having relatively more ethane injection (e.g., 8% $H_2$ for Case-1 and about $H_2$ 10% for Case-2). The amount of ethane that can be injected can be limited by the desired temperature exiting the OCM reaction region 202 or the OCM reactor 214.

Methane can be combined with a recycle stream from downstream separation units prior to or during introduction into an OCM reactor. In the OCM reactor, methane can catalytically react with an oxidizing agent to yield $C_{2+}$ compounds. The oxidizing agent can be oxygen ($O_2$), which may be provided by way of air or enriched air. Oxygen can be extracted from air, for example, in a cryogenic air separation unit.

To carry out an OCM reaction in conjunction with some catalytic systems, the methane and oxygen containing gases may need to be brought up to appropriate reaction temperatures, e.g., in excess of 450° C. for some catalytic OCM processes, before being introduced to the catalyst, in order to allow initiation of the OCM reaction. Once that reaction begins or "lights off," then the heat of the reaction may be sufficient to maintain the reactor temperature at appropriate levels. Alternatively or additionally, these processes may operate at a pressure above atmospheric pressure, such as in the range of about 1 to 30 bars (absolute).

Once formed, $C_{2+}$ compounds can be subjected to further processing to generate one or more desired or otherwise predetermined chemicals. In some situations, alkane components of the $C_{2+}$ compounds are subjected to cracking in an OCM reactor or a reactor downstream of the OCM reactor to yield other compounds, such as alkenes (or olefins). See, e.g., U.S. Patent Publication No. 2015/0152025, which is entirely incorporated herein by reference.

The OCM effluent can be cooled after the conversion to ethylene has taken place. The cooling can take place within a portion of the OCM reactor and/or downstream of the OCM reactor (e.g., using at least about 1, 2, 3, 4, 5 or more heat exchangers). In some cases, a heat exchanger is a heat recovery steam generator (HRSG), such as the apparatus described herein. Cooling the OCM effluent suitably rapidly and to a suitably low temperature can prevent undesirable reactions from occurring with the OCM effluent, including, but not limited to the formation of coke or other by-products.

In some embodiments, the OCM effluent is cooled to a target temperature of less than or equal to about 700° C., 650° C., 600° C., 550° C., 500° C., 450° C., 400° C., 350° C., 300° C., ° C., 200° C., or less. In some cases, the OCM effluent is cooled to the target temperature less than or equal to about 1 second, 900 milliseconds (ms), 800 ms, 700 ms, 600 ms, 500 ms, 400 ms, 300 ms, 200 ms, 100 ms, 80 ms, 60 ms, 40 ms, 20 ms, or less of the production of the desired or otherwise predetermined concentration of a compound (e.g., ethylene) in the OCM reaction.

In some situations, an OCM system generates ethylene that can be subjected to further processing to produce different hydrocarbons with the aid of one or more conversion processes (or systems). Such a process can be part of an ethylene to liquids (ETL) process flow comprising one or more OCM reactors, separations units, and one or more conversion processes for generating higher molecular weight hydrocarbons. The conversion processes can be integrated in a switchable or selectable manner in which at least a portion or all of the ethylene containing product can be selectively directed to at least about 1, 2, 3, 4, 5, 6, 7, 8, 9, 10, or more different process paths to yield as many different hydrocarbon products. An example OCM and ETL (collectively "OCM-ETL" herein) is provided in U.S. Patent Publication No. 2014/0171707, which is entirely incorporated herein by reference.

An aspect of the present disclosure provides OCM processes that are configured to generate olefins (or alkenes), such as ethylene, propylene (or propene), butylenes (or butenes), etc. An OCM process can be a standalone process or can be integrated in a non-OCM process, such as a natural gas liquid(s) (NGL or NGLs) or gas processing system.

Reference will now be made to the figures, wherein like numerals refer to like parts throughout. It will be appreciated that the figures and features therein are not necessarily drawn to scale. In the figures, the direction of fluid flow between units is indicated by arrows. Fluid may be directed from one unit to another with the aid of valves and a fluid flow system. In some examples, a fluid flow system can include compressors and/or pumps, as well as a control system for regulating fluid flow, as described elsewhere herein.

In some cases, the process equipment is sized to accommodate a range of amounts of additional ethane such that the process is flexible. For example, more ethane can be injected into the process when the price of ethane is relatively cheap in comparison to the price of natural gas (e.g., low frac spread).

The ethane can be mixed with the natural gas and recycled to the OCM unit. The ethane can go straight to the OCM reactor, optionally through a separate de-sulfurization module. Injection of ethane through a separate de-sulfurization module can reduce the load in the recycle loop of the process and/or give additional production capacity keeping the same recirculation rate. The purge gas from the process can be used for fuel gas to the fired heater or sales gas.

The concentration of ethane in the feed to the OCM reactor can be any suitable value, including greater than or equal to about 0.0 mol %, 0.25 mol %, 0.5 mol %, 0.75 mol %, 1.0 mol %, 1.25 mol %, 1.5 mol %, 1.75 mol %, a 2.0 mol %, 2.25 mol %, 2.5 mol %, 2.75 mol %, 3.0 mol %, 3.25 mol %, 3.5 mol %, 3.75 mol %, 4.0 mol %, 4.25 mol %, 4.5 mol %, 4.75 mol %, 5.0 mol %, 25 mol %, 5.5 mol %, 5.75 mol %, 6.0 mol %, 7.0 mol %, 8.0 mol %, 9.0 mol %, 10.0 mol % or more. In some cases, the concentration of ethane in the feed to the OCM reactor is less than or equal to about 25 mol %, 20 mol %, 15 mol %, 10 mol %, 9 mol %, 8 mol %, 7 mol %, 6 mol %, 5 mol %, 4 mol %, 3 mol %, 2 mol %, 1 mol %, 0.8 mol %, 0.6 mol %, 0.4 mol %, 0.2 mol %, 0.1 mol % or less. In some cases, the concentration of ethane in the feed to the OCM reactor is between any of the two values described above, for example, between about 0.01 mol % to about 5 mol %.

The systems and methods of the present disclosure can be carbon-efficient and/or energy-efficient. In some cases, the systems or methods of the present disclosure have a carbon efficiency of at least about 50%, at least about 55%, at least about 60%, at least about 65%, at least about 70%, at least about 75%, at least about 80%, at least about 85%, at least about 90%, or more. In some cases, a system of the present disclosure or method for use thereof has a ratio of all carbon atoms output from the system as hydrocarbons to all carbon atoms input to the system of at least about 0.40, at least about 0.50, at least about 0.55, at least about 0.60, at least about 0.65, at least about 0.70, at least about 0.75, at least about 0.80, at least about 0.85, at least about 0.90, at least about 0.95, or more.

In some cases, the systems or methods of the present disclosure have a carbon efficiency of between about 50% and about 85%, between about 55% and about 80%, between about 60% and about 80%, between about 65% and about 85%, between about 65% and about 80%, or between about 70% and about 80%. In some cases, a system of the present disclosure or method for use thereof has a ratio of all carbon atoms output from the system as hydrocarbons to all carbon atoms input to the system of between about 0.50 and about 0.85, between about 0.55 and about 0.80, between about 0.60 and about 0.80, between about 0.65 and about 0.85, between about 0.65 and about 0.80, or between about 0.70 and about 0.80.

In some cases, the systems and methods combine OCM reaction, post-bed cracking (PBC), separations and methanation reactions. The separations can include oligomerization of ethylene to $C_{3+}$ compounds, which are more easily separated as described in PCT Patent Publication No. WO/2015/105911, which is incorporated herein by reference in its entirety. Additional details of OCM reactor and process design can be found in PCT Patent Publication Nos. WO/2015/081122 and WO/2015/106023, each of which is incorporated herein by reference in their entirety.

In an aspect, provided herein is a method for performing oxidative coupling of methane (OCM). The method can comprise (a) reacting oxygen ($O_2$) with methane ($CH_4$) to form heat, ethylene ($C_2H_4$) and optionally ethane ($C_2H_6$), hydrogen ($H_2$), carbon monoxide (CO) or carbon dioxide ($CO_2$); (b) reacting the heat produced in (a) with ethane ($C_2H_6$) to form ethylene ($C_2H_4$) and hydrogen ($H_2$); (c) performing at least one of (i) enriching the ethylene ($C_2H_4$) produced in (a) and (b) or (ii) oligomerizing the ethylene ($C_2H_4$) produced in (a) and (b) to produce $C_{3+}$ compounds and enriching the $C_{3+}$ compounds; and (d) reacting the hydrogen ($H_2$) produced in (a) and (b) with carbon monoxide (CO) and/or carbon dioxide ($CO_2$) to form methane ($CH_4$).

In another aspect, provided herein is a system for performing oxidative coupling of methane (OCM). The system can comprise an OCM reactor that permits oxygen ($O_2$) and methane ($CH_4$) to react in an OCM process to form heat, ethylene ($C_2H_4$) and optionally ethane ($C_2H_6$), hydrogen ($H_2$), carbon monoxide (CO) or carbon dioxide ($CO_2$). The system can further comprise a cracking vessel in fluid communication with the OCM reactor, which cracking vessel may utilize the heat produced in the OCM reactor to convert ethane ($C_2H_6$) into ethylene ($C_2H_4$) and hydrogen ($H_2$). The system can further comprise a separations module in fluid communication with the cracking vessel. The separations module may (i) enrich the ethylene ($C_2H_4$) produced in the OCM reactor and the cracking vessel or (ii) oligomerize the ethylene ($C_2H_4$) produced in the OCM reactor and the cracking vessel to produce $C_{3+}$ compounds and enriches the $C_{3+}$ compounds. The system can further comprise a methanation reactor in fluid communication with the separations module. The methanation reactor may permit the hydrogen ($H_2$) produced in the OCM reactor and the cracking vessel to react with carbon monoxide (CO) and/or carbon dioxide ($CO_2$) to form methane ($CH_4$).

In some cases, the ethane ($C_2H_6$) that is cracked in the cracking vessel is produced in the OCM reactor. In some instances, at least some of the ethane ($C_2H_6$) that is cracked is in addition to the ethane ($C_2H_6$) that was produced in the OCM reactor. In some cases, the OCM reactor produces ethane ($C_2H_6$), hydrogen ($H_2$), carbon monoxide (CO) and carbon dioxide ($CO_2$). In some cases, the carbon monoxide (CO) and carbon dioxide ($CO_2$) produced in the OCM reactor is methanated. The separations module can separate ethylene ($C_2H_4$) or $C_{3+}$ compounds from methane ($CH_4$), ethane ($C_2H_6$), hydrogen ($H_2$), carbon monoxide (CO) or carbon dioxide ($CO_2$). In some instances, the cracking vessel is a portion of the OCM reactor.

The methane formed in the methanation reactor can be returned to the OCM reactor or sold as sales gas. In some embodiments, the OCM reactor has an OCM catalyst. In some embodiments, the methanation reactor has a methanation catalyst. In some embodiments, the separations module comprises an ethylene-to-liquids (ETL) reactor comprising an oligomerization catalyst. At least some of the heat produced in the OCM reactor can be converted to power.

In another aspect, described herein is a method for producing $C_{2+}$ compounds from methane ($CH_4$). The method can comprise: (a) performing an oxidative coupling of methane (OCM) reaction which converts methane ($CH_4$) and oxygen ($O_2$) into ethylene ($C_2H_4$) and optionally ethane ($C_2H_6$); (b) optionally oligomerizing the ethylene ($C_2H_4$) to produce $C_{3+}$ compounds; and (c) isolating the $C_{2+}$ compounds, wherein the $C_{2+}$ compounds may comprise the ethylene ($C_2H_4$), the ethane ($C_2H_6$) and/or the $C_{3+}$ compounds. In some cases, the method has a carbon efficiency of at least about 50%, 60%, 70%, 80%, 905, 95%, or more. In some cases, the isolated the $C_{2+}$ compounds are not pure. In some cases, the isolated the $C_{2+}$ compounds comprise methane, CO, $H_2$, $CO_2$ and/or water.

In some cases, the systems or methods of the present disclosure consume less than or equal to about 150, 140, 130, 120, 110, 100, 95, 90, 85, 80, 75, 70, 65, 60, 55, or 50, or less million British Thermal Units (MMBtu) of energy per ton of ethylene ($C_2H_4$) or $C_{3+}$ compounds enriched. In some cases, the amount of energy consumed by the system includes the energy content of the feedstock used to make the ethylene ($C_2H_4$) or $C_{3+}$ compounds.

In some cases, the systems or methods of the present disclosure have consume between about 65 and about 100, between about 70 and about 110, between about 75 and about 120, between about 85 and about 130, between about 40 and about 80, or between about 50 and about 80 MMBtu of energy per ton of ethylene ($C_2H_4$) or $C_{3+}$ compounds enriched. In some cases, the amount of energy consumed by the system includes the energy content of the feedstock used to make the ethylene ($C_2H_4$) or $C_{3+}$ compounds.

In some cases, the systems or methods of the present disclosure have a specific oxygen consumption of greater than or equal to about 1.2, about 1.3, about 1.4, about 1.5, about 1.6, about 1.7, about 1.8, about 1.9, about 2.0, about 2.1, about 2.2, about 2.3, about 2.4, about 2.5, about 2.6 about 2.7, about 2.8, about 2.9, about 3, about 3.2, about 3.4, about 3.6, about 3.8, about 4.0, or more.

In some cases, the systems or methods of the present disclosure have a specific oxygen consumption of between about 1.2 and about 2.7, between about 1.5 and about 2.5, between about 1.7 and about 2.3 or between about 1.9 and about 2.1.

In some cases, the systems or methods of the present disclosure have a specific $CO_2$ emission of greater than or equal to about 0.5, about 0.6, about 0.7, about 0.8, about 0.9, about 1.0, about 1.1, about 1.2, about 1.3, about 1.4, about 1.5, about 1.6, about 2.0, about 2.2, about 2.4, about 2.6, about 2.8, about 3.0, about 3.2, about 3.4, about 3.6, or more.

In some cases, the systems or methods of the present disclosure have a specific $CO_2$ emission of between about 0.5 and about 1.7, between about 0.7 and about 1.4, between about 0.8 and about 1.3 or between about 0.9 and about 1.1.

In some cases, the systems or methods of the present disclosure produces $C_{2+}$ products, and the $C_{2+}$ products comprise at least about 1%, 2.5%, 5%, 7.5%, 10%, 12.5%, 15%, 17.5%, 20% (wt % or mol %) or more $C_{3+}$ hydrocarbons.

In some cases, the systems or methods of the present disclosure produces $C_2$ products and $C_{3+}$ products, and a molar ratio of the $C_2$ products to the $C_{3+}$ products is at least or equal to about 2, 3, 4, 5, 6, 7, 8, 9, 10, 11, 12, 13, 14, 15, 16, 17, 18, 19, 20 or more. In some cases, the molar ratio of the $C_2$ products to the $C_{3+}$ products is less than or equal to about 50, 45, 40, 35, 30, 25, 20, 18, 16, 14, 12, 10, 8, 6, 4, 2, or less. In some cases, the molar ratio of the $C_2$ products to the $C_{3+}$ products is between any of the two values described above, for example, from about 5 to about 20.

In another aspect, provided herein is a method for producing $C_{2+}$ compounds from methane ($CH_4$), the method comprising: (a) performing an oxidative coupling of methane (OCM) reaction which may convert methane ($CH_4$) and oxygen ($O_2$) into ethylene ($C_2H_4$) and optionally ethane ($C_2H_6$); (b) optionally oligomerizing the ethylene ($C_2H_6$) to produce $C_{3+}$ compounds; and (c) isolating the $C_{2+}$ compounds, wherein the $C_{2+}$ compounds may comprise the ethylene ($C_2H_4$), the ethane ($C_2H_6$) and/or the $C_{3+}$ compounds. In some cases, the amount of energy consumed by the system includes the energy content of the feedstock used to make the isolated $C_{2+}$ compounds. In some cases, the isolated the $C_{2+}$ compounds are not pure. In some cases, the isolated the $C_{2+}$ compounds comprise methane, CO, $H_2$, $CO_2$ and/or water.

In some cases, the method consumes less than or equal to about 150, 140, 130, 120, 110, 100, 95, 90, 85, 80, 75, 70, 65, 60, 55, 50, or less MMBtu of energy per ton of $C_{2+}$ compounds isolated. In some cases, the method consumes greater than or equal to about 20, 30, 40, 50, 60, 70, 80, 90, 100, or more MMBtu of energy per ton of $C_{2+}$ compounds isolated. In some cases, the method consumes between about 65 and about 100, between about 70 and about 110, between about 75 and about 120, between about 85 and about 130, between about 40 and about 80, or between about 50 and about 80 MMBtu of energy per ton of $C_{2+}$ compounds isolated.

In another aspect, provided herein is a method for producing $C_{2+}$ compounds from methane ($CH_4$). The method may comprise performing an oxidative coupling of methane (OCM) reaction using an OCM catalyst. The OCM reaction may be performed at a set of reaction conditions to convert a quantity of methane ($CH_4$) into ethylene ($C_2H_4$) at a carbon efficiency. The OCM catalyst may have a $C_{2+}$ selectivity at the set of reaction conditions that is less than the carbon efficiency at the set of reaction conditions. The set of reaction conditions can include a temperature, a pressure, a methane to oxygen ratio and a gas hourly space velocity (GHSV).

In another aspect, provided herein is a method for producing $C_{2+}$ compounds from methane ($CH_4$). The method may comprise (a) performing an oxidative coupling of methane (OCM) reaction using an OCM catalyst at a set of reaction conditions to convert a quantity of methane ($CH_4$) into ethylene ($C_2H_4$) and ethane ($C_2H_6$); and (b) cracking the ethane ($C_2H_6$) to produce additional ethylene ($C_2H_4$). The combined carbon efficiency of (a) and (b) may be greater than the $C_{2+}$ selectivity of the OCM catalyst at the set of reaction conditions. The set of reaction conditions can include a temperature, a pressure, a methane to oxygen ratio and a gas hourly space velocity (GHSV).

In some instances, the $C_{2+}$ selectivity is less than or equal to about 70%, 65%, 60%, 55%, 50%, 45%, 40%, 35%, 30% or less. In some instances, the $C_{2+}$ selectivity is greater than or equal to about 20%, 25%, 30%, 35%, 40%, 50%, 60%, 70%, 80%, or more. In some cases, the $C_{2+}$ selectivity is between any of the two values described herein, for example, from about 25% to about 50%.

In another aspect, provided herein is a method for producing $C_{2+}$ compounds. The method may comprise a) providing a first feedstock comprising methane ($CH_4$) and optionally a first amount of ethane ($C_2H_6$); (b) performing an OCM reaction on the first feedstock to produce an OCM product comprising a first amount of ethylene ($C_2H_4$); (c) combining the OCM product with a second feedstock comprising a second amount of ethane ($C_2H_6$) to produce a third feedstock; and (d) cracking the third feedstock to produce a second amount of ethylene ($C_2H_4$). In some cases, the second amount of ethylene includes ethylene produced in (b) and (d).

In some cases, the fraction of the second amount of ethylene ($C_2H_4$) that is derived from the first or the second amounts of ethane ($C_2H_6$) is at least about 1%, at least about 3%, at least about 5%, at least about 7%, at least about 10%, at least about 15%, at least about 20%, at least about 25%, at least about 30%, at least about 35%, at least about 40%, at least about 45%, at least about 50%, at least about 55%, or more.

In some cases, the combined moles of the first amount and second amount of ethane ($C_2H_6$) divided by the combined moles of the first feedstock and the second feedstock is greater than or equal to about 1%, 3%, 5%, 7%, 10%, 15%, 20%, 25%, 30%, 35%, 40%, 45%, 50%, 55%, 60%, or more. In some cases, the combined moles of the first amount and second amount of ethane ($C_2H_6$) divided by the combined moles of the first feedstock and the second feedstock is less than or equal to about 90%, 80%, 70%, 60%, 50%, 40%, 30%, 20%, 10% or less.

In some cases, the combined moles of the first amount and second amount of ethane ($C_2H_6$) divided by the combined moles of the first feedstock and the second feedstock is between about 1% and about 50%, between about 1% and about 40%, between about 1% and about 30%, between about 1% and about 20%, between about 1% and about 15%, between about 1% and about 10%, or between about 10% and about 50%.

In some cases, the first feedstock is natural gas. In some cases, the first feedstock is natural gas supplemented with the first amount of ethane ($C_2H_6$). In some cases, the first feedstock is natural gas having passed through a separations system to substantially remove the hydrocarbons other than methane.

In some cases, the molar percent of ethane ($C_2H_6$) in methane ($CH_4$) in the first feedstock is greater than or equal to about 1%, 3%, 5%, 7%, 10%, 15%, 20%, or more.

In some cases, some or all of a methane-containing feed stream (e.g., natural gas) can be processed in a separation system prior to being directed into an OCM reactor. Directing a methane-containing feed stream into an OCM reactor via a separation system or subsystem rather than into an OCM reactor directly can provide advantages, including but not limited to increasing the carbon efficiency of the process, optimizing the OCM process for methane processing, and optimizing the post-bed cracking (PBC) process for ethane processing. Such a configuration can result in higher back-end sizing for the system. In some cases (e.g., when using high pressure pipeline natural gas as a feedstock, high recycle ratio), the back-end sizing increase can be reduced or moderated. The separation system or subsystem can comprise a variety of operations including any discussed in the present disclosure, such as $CO_2$ removal via an amine system, caustic wash, dryers, demethanizers, deethanizers, and $C_2$ splitters. In some cases, all of the methane and ethane in the methane-containing feed stream (e.g., natural gas) passes through a separations system or separations subsystem prior to passing through an OCM reactor. Some or all of the ethane from the feed stream can be directed from the separation system or subsystem into the inlet of an OCM reactor or into a post-bed cracking (PBC) unit.

In some configurations, an OCM system can be operated in a cycle, with at least some of the products from one unit or subsystem being processed or reacted in the next unit or subsystem. For example, oxygen ($O_2$) and methane ($CH_4$) feed can be provided to an OCM reactor, which produces an OCM product stream comprising ethane ($C_2H_6$), ethylene ($C_2H_4$), carbon monoxide (CO) and/or carbon dioxide ($CO_2$), and heat. The OCM product stream can then be fed into an ethane conversion subsystem (e.g., a cracking vessel or an ethane cracker) in fluid communication with the OCM reactor. The ethane conversion subsystem can also receive an additional $C_2H_6$ stream. The ethane conversion subsystem can convert $C_2H_6$ (e.g., crack $C_2H_6$ to $C_2H_4$) with the aid of the heat liberated by the OCM reaction. The heat can also be used to crack the $C_2H_6$ in the additional $C_2H_6$ stream. A $C_2H_4$ product stream can then be directed from the ethane conversion subsystem into a separations module in fluid communication with the ethane conversion subsystem. The separations module can enrich products such as $C_2H_4$ in the product stream. The separations module can also oligomerize $C_2H_4$ to form compounds comprising three or more carbon atoms ($C_{3+}$ compounds). An enriched product stream enriched in $C_2H_4$ and/or $C_{3+}$ compounds can be recovered from the separations module. A lights stream comprising components such as hydrogen ($H_2$) (e.g., hydrogen generated from the cracking of $C_2H_6$) and CO and/or $CO_2$ can be recovered from the separations module and directed into a methanation reactor in fluid communication with the separations module. The methanation reactor can react $H_2$ with CO and/or $CO_2$ to form a methanated stream comprising $CH_4$. The methanated stream can then be directed into the OCM reactor to provide additional methane for the OCM process. In some cases, energy generated in the methane conversion section in the form of high pressure steam, high temperature steam, heat, electricity, heat transferred via gas-gas heat exchanger, heat transferred via gas-liquid heat exchanger, or other forms, can be used to provide all of the energy and power required to run the entire plant or system.

In some cases, a cyclical system or process can operate with a carbon efficiency such as those discussed in this disclosure. For example, such a system or process can operate with a carbon efficiency of greater than or equal to about 50%, 55%, 60%, 65%, 70%, 75%, 80%, 85%, 90%, or more. In some cases, such a system or process can operate with a carbon efficiency of between about 50% and about 85%, between about 55% and about 80%, between about 60% and about 80%, between about 65% and about 85%, between about 65% and about 80%, or between about 70% and about 80%.

In some cases, such a system or process (or method) can operate such that a ratio of all carbon atoms output from the system as hydrocarbons to all carbon atoms input to the system is greater than or equal to about 0.50, 0.55, 0.60, 0.65, 0.70, 0.75, 0.80, 0.85, 0.90, or more. In some cases, such a system or process can operate such that a ratio of all carbon atoms output from the system as hydrocarbons to all carbon atoms input to the system is between about 0.50 and about 0.85, between about 0.55 and about 0.80, between about 0.60 and about 0.80, between about 0.65 and about 0.85, between about 0.65 and about 0.80, or between about 0.70 and about 0.80.

An example process can comprise an OCM unit, a process gas compressor, a process gas cleanup unit, a cryogenic separations unit, a fractionation unit, a methanation unit, and a sulfur-removal unit. An oxygen stream may be fed into the OCM unit, along with a $C_1$ recycle stream from the methanation unit and a $C_2$ recycle stream from the fractionation unit. A natural gas stream and an ethane stream may be fed into the sulfur removal unit. Output from the OCM unit and the sulfur removal unit may be directed into the process gas compressor, and then into the process gas cleanup unit, which removes a $CO_2$ stream. The remaining product stream may be directed into the cryogenic separations unit, where light components including $H_2$ and CO or $CO_2$ may be directed into the methanation unit, and the remaining product stream, including ethylene and other $C_{2+}$ compounds, may be directed into the fractionation unit. The fractionation unit may be configured to separate an ethylene stream and a $C_{3+}$ compound stream comprising $C_3$ compounds, $C_4$ compounds, and $C_{5+}$ compounds, as well as the $C_2$ recycle which may be directed back to the OCM unit. The methanation unit may convert the light components into methane, a first portion of which may be recycled to the OCM unit and a second portion of which may be output as sales gas. The operating flow rates for the input streams may be as follows: 20.3 MT/h of oxygen, 16.0 MT/h of natural gas, and 2.9 MT/h of ethane. The operating flow rates for the output streams may be as follows: 9.0 MT/h of ethylene, 1.4 MT/h of $C_{3+}$ compounds, 4.3 MT/h of sales gas, and 8.2 MT/h of $CO_2$. The corresponding carbon content of the input streams may be 972 kmol/h of carbon in the natural gas stream, and 194 kmol/h of carbon in the ethane stream. The corresponding carbon content of the output streams may be 642 kmol/h of carbon in the ethylene stream, 96 kmol/h of carbon in the $C_{3+}$ compounds stream, 247 kmol/h of carbon in the sales gas stream, and 181 kmol/h of carbon in the $CO_2$ stream. The amount of carbon input to the system may be 1166 kmol/h, and the amount of carbon output from the system in hydrocarbon products (e.g., excluding $CO_2$) is 985 kmol/h, for a resulting carbon efficiency of 84.5%.

Reaction heat (e.g., OCM reaction heat) can be used to supply some, most, or all of the energy used to operate systems and perform processes of the present disclosure. In some examples, reaction heat can be used to supply greater than or equal to about 50%, 55%, 60%, 65%, 70%, 75%, 80%, 85%, 90%, 95%, 96%, 97%, 98%, 99%, or 100% of energy for operating systems and performing processes of the present disclosure. For example, the reaction heat can be used to supply at least about 80% or 90% of all of the energy for operating systems or processes of the present disclosure. This can provide for an efficient, substantially self-contained system with reduced or even minimum external energy input.

Integration of OCM Processes with Other Chemical Processes

The present disclosure provides systems and methods for integrating OCM systems and methods with various chemical processes, such as methanol (MeOH) production, chlorine ($Cl_2$) and sodium hydroxide (NaOH) production (e.g., chloralkali process), vinylchloride monomer (VCM) production, ammonia ($NH_3$) production, processes having syngas (e.g., mixtures of hydrogen ($H_2$) and carbon monoxide (CO) in any proportion), olefin derivative production, or combinations thereof.

As will be appreciated, the capital costs associated with each of the facility types described above can run from tens of millions to hundreds of millions of dollars each. Additionally, there are inputs and outputs, of these facilities, in terms of both energy and materials, which may have additional costs associated with them, both financial and otherwise that may be further optimized in terms of cost and efficiency. In some cases, because different facilities tend to be optimized for the particularities (e.g., products, processing conditions) of the market in which they exist, they tend to be operated in an inflexible manner, in some cases without the flexibility or option to optimize for their given market. The present inventors have recognized surprising synergies when integrating OCM with the aforementioned chemical processes which can result in improved economics and/or operational flexibility.

In some cases, the OCM processes described herein are integrated with an olefin oligomerization process, such as an ethylene-to-liquids ("ETL") process as described in U.S. Patent Publication Nos. 2014/0171707 and 2015/0232395, each of which is incorporated herein by reference in its entirety for all purposes.

In some instances, the OCM process can be sized to fit the needs of an ethylene derivatives plant. Such a synergy can liberate the derivatives producer from being a merchant buyer of ethylene, allowing the producer more ethylene cost and supply certainty. Examples of ethylene derivatives include polyethylene, including low-density polyethylene (LDPE), linear low-density polyethylene (LLDPE), and high-density polyethylene (HDPE). Additional ethylene derivatives may include ethylbenzene, styrene, acetic acid, vinylacetate monomer, ethylene dichloride, vinylchloride monomer, ethylene oxide, alpha olefins and combinations thereof.

Integration of OCM Processes with a Butene Process

OCM processes can be integrated with processes for the production of Butenes. Polymer grade Ethylene from the OCM process can be a feedstock to a dimerization system. The dimerization system may comprise a dimerization Reactor loop, and associated recovery and purification systems. The ethylene may be dimerized to a C4 olefin, i.e., butene-2, butene-1, iso-butene, and/or some higher hydrocarbons like hexene and octene. Selectivity to butene-2 can be as high as about 90%, 91%, 92%, 93%, 94%, 95%, or more. The dimerization reactor outlet, can be treated to recover the butene-2, or isomerized to further increase the yield of butene-2. The mix butenes product can be used to manufacture sec-butyl alcohol (SBA) via hydration. The SBA can be further converted to methyl ethyl ketones. Alternately, the mix butenes stream can be fed to a metathesis unit, as discussed below, to produce e.g., polymer grade propylene.

The butene production reaction process can take place in a liquid phase reactor loop. The liquid phase reactor may use a nickel-based phosphine complex with an ethyl aluminum dichloride (EADC) co-catalyst. The reactions may comprise dimerization (to butene-2), butene-1 production, dimerization of ethylene and butene to make hexene, dimerization of butenes to form octene and dimerization of hexene and ethylene to form octene. The catalyst and co-catalyst can be stored in a hexane solvent. Dimerization may be an exothermic reaction that liberates heat. The liberated heat can be used in the process.

Figure 3:
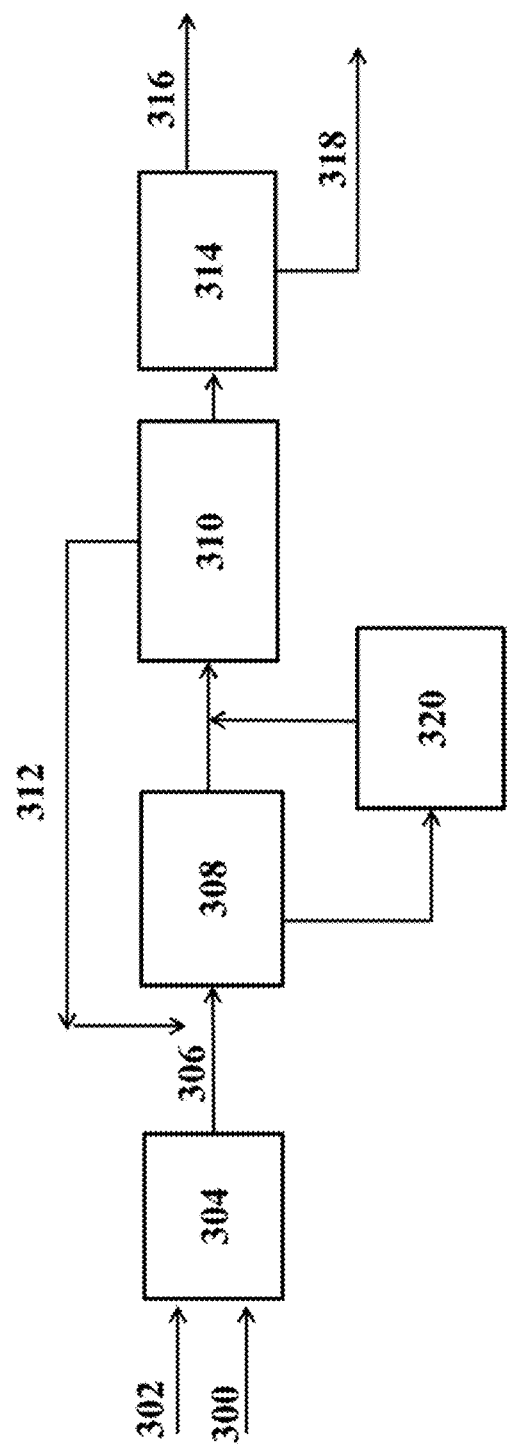
FIG. 3 shows a schematic illustration of an example OCM process that can produce butene-1.

OCM process described herein can be integrated with a process that produces butene-1. With reference to FIG. 3, oxygen 300 can be mixed with methane 302 in an OCM process 304 to produce ethylene 306. The ethylene can be enriched or purified (e.g., to polymer grade ethylene) using any suitable separations operations (e.g., cryogenic separations). The ethylene can be sent to a dimerization unit 308 that produces butene-1 and some olefinic material such as hexenes and octenes. An ethylene recovery module 310 can be used to separate un-reacted ethylene from the dimerization product stream, and optionally recycle 312 the ethylene. A butene-1 recovery module 314 can be used to produce an enriched butene-1 stream 316 along with some co-products 318 (e.g., $C_{6+}$ compounds). Ethane can be recycled to OCM (not shown). The dimerization reaction can selectively dimerize ethylene into butene-1 using a titanium based catalyst, which can be recovered in a catalyst recovery module 320. The titanium catalyst may be a homogenous catalyst based on a Ziegler-Natta type titanium complex that affords a titanium (IV) cyclic compound in the presence of ethylene, which decomposes to butene-1 by an intramolecular β-hydrogen transfer reaction (i.e., the Alphabutol™ process). The reaction can be performed at 50° C. and 1-3 MPa. The reaction can take place without solvent in a one stage stirred reactor. The reactor effluent can be treated with an amine to deactivate the catalyst and prevent isomerization of buten-1 to butene-2. The butene-1 can be used as a co-monomer in linear low density polyethylene production (LLDPE). An integrated OCM and polyethylene plant with an option to produce butene-1 required as a co-monomer for LLDPE can produce high value end-products and provide operational flexibility.

Integration of OCM Processes with a Propylene Process

OCM processes can be integrated with processes for the production of propylene, such as metathesis processes.

Metathesis reaction may be a disproportionation reaction, redistribution of fragments of alkenes (olefins) by the scission and regeneration of carbon-carbon double bonds. Metathesis unit may comprise a reactor system, where the disproportionation reaction takes place, and associated recovery and purification systems.

The primary feedstocks to the metathesis unit may be a C4 rich stream and ethylene. The product may comprise propylene. The C4 stream may contain butene-2, butene-1, iso-butene, butanes, or combinations thereof. Higher concentration of butene-2 (e.g., at least about 30%, 40%, 50%, 60%, 70% (wt %, or mol %) or more of the C4 stream may be butene-2) may be desired in some cases. The propylene produced can be of polymer grade and used as a feedstock to produce polypropylene.

Metathesis can be conducted as a vapor phase equilibrium reaction. Metathesis can achieve n-butene conversion greater than or equal to about 50%, 60%, 65%, 70%, 75%, or more single pass and greater than or equal to about 75%, 80%, 85%, 90%, 95% or more overall conversion. Propylene selectivity may be greater than or equal to about 80%, 82%, 84%, 86%, 88%, 90%, 91%, 92%, 93%, 94%, 95%, 96%, 97%, 98%, 99% or higher. The reaction can be conducted at isothermal or nearly isothermal conditions, and can be energy neutral.

The metathesis reaction can utilize an ethylene feed and a C4 olefinic feed to produce propylene via a disproportionation reaction. In the absence of a $C_4$ feed, ethylene can be dimerized to produce the $C_4$ olefins used for metathesis. The $C_4$ olefin can be a butene-2 rich stream where the butene-2 content can be greater than or equal to about 75%, 80%, 85%, 90%, 93%, 95%, 97%, 99% or more. An OCM module can provide (polymer grade) ethylene to a dimerization unit, and/or to a metathesis unit. The metathesis reactor may contain a section for isomerization of butene-1 to butene-2. The product from the metathesis unit can contain predominantly propylene (and varying amounts of unreacted ethylene and butenes), along with some heavy $C_{5+}$ components. Metathesis units can include $C_2$ separation, $C_3$ separation and a removal section to remove $C_{5+}$ components.

Feedstocks to the metathesis unit can be derived from a steam cracker, which can supply polymer grade ethylene and a C4 stream rich in butenes. Alternatively, polymer grade ethylene can be fed to a dimerization reactor loop where the ethylene may be dimerized to produce butenes. The concentration of butene-2 in the produced butenes can be greater than or equal to about 85%, 88%, 90%, 92%, 95% or more. The dimerization system integrated with an OCM may be an ideal situation to produce propylene using a metathesis unit. The OCM unit may provide ethylene to both the dimerization unit and the metathesis unit, the capacities are defined so that the entire Ethylene produced from the OCM is utilized either in the dimerization unit to produce C4 feedstock for the metathesis or as a feedstock to the metathesis unit. Alternatively, the OCM can be sized to produce extra ethylene, which can be sent to the polypropylene unit as a co-monomer.

In some cases, the dimerization unit can produce predominantly 1-butene (i.e., more butene-1 than butene-2, e.g., at least about 70%, at least about 80%, at least about 90%, or at least about 95% butene-2). In some cases, the systems and methods of the present disclosure can have a process unit to enhance the production of 2-butene. Non-limiting examples of such process units may include, a hydroisomerization unit to convert 1-butene to 2-butene, a selective hydrogenation unit to hydrogenate any butadiene to butenes, or combinations thereof. The hydroisomerization and hydrogenation units can be within one reactor system, or separate reactor systems. In some cases, the isomerization, hydrogenation and separation systems are contained in one vessel (e.g., tower) or reactor system. Such a system can take in a mixed C4 feed, containing predominantly 2-butene, and some 1-butene, butadiene, and i-butene. The system can hydroisomerize the 1-butene to 2-butene, hydrogenate the butadiene and also separate 2-butene from the rest of the C4 components which can then be fed to a metathesis reactor. If the dimerization system produces mainly 1-butene, the hydroisomerization system can be a separate reactor system (e.g., that hydroisomerizes and hydrogenates) with an additional separate separation system to separate the 2-butene from i-butene and remaining butanes and other C4 compounds.

In some cases, the catalytic hydroisomerization takes place under an atmosphere of hydrogen. In some cases, sulfur can be present in either the feed or added to the hydrogen stream as an additive to reduce the hydrogenation tendency of the catalyst and thus increase the hydroisomerization.

Figure 4:
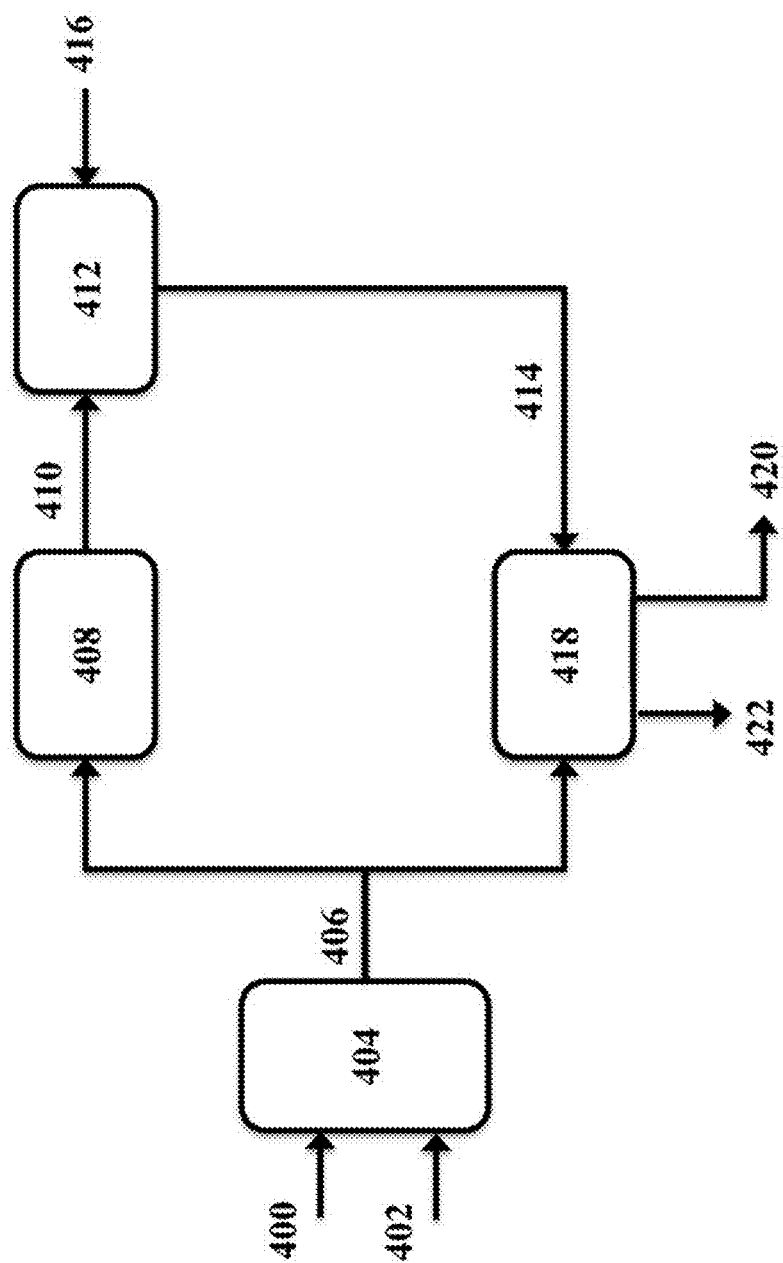
FIG. 4 shows a schematic illustration of an example OCM process that can produce propylene using butene-1 as an intermediate.

FIG. 4 shows an example system of the present disclosure, where the ethylene from OCM is the feedstock to the dimerization unit and the metathesis unit. Oxygen 400 and a feedstock comprising methane 402 can be fed to an OCM reactor 404 to produce ethylene 406. Some of the ethylene can be dimerized 408 to produce butene-1 410, which can be isomerized 412 to butene-2 414 using hydrogen 416. The butene-2 can be reacted with additional ethylene in a metathesis reactor 418 to produce propylene 420. In some cases, the system also produces a C4 stream 422 that can be recycled or purged.

Some selective hydrogenation of butadienes can take place in the isomerization reactor 412. The isomerization reactor can be followed by a separation module (not shown) which separates the 2-butene to be fed to the metathesis reactor unit 418. In some cases, the up-front separation module is not required. In these cases, the C4 product which contains mainly 2-butene 414 is fed to the metathesis reactor 418 and a final separation is carried out on the metathesis effluent 420 and/or 422.

In some cases, the system has separate separation modules for OCM and metathesis. In these cases, an OCM unit can be designed to produce polymer grade ethylene (i.e., using a separations module dedicated to the OCM effluent into high purity, in some cases polymer grade ethylene). The polymer grade ethylene may be sent to the dimerization and metathesis unit. Butene-2 can be produced in a dimerization reactor. The butene-2 rich stream and the polymer grade ethylene from the OCM separation module can go to the metathesis reactor where propylene is produced. The metathesis section of the process can have its own separation module (i.e., separate from the OCM separations module), which produces polymer grade propylene by separating unreacted ethylene and heavier molecules (such as fuel oil and gasoline). The heavier molecules can be separated in two separate columns or a single column and sent for further processing. In some instances, the system produces polymer grade propylene. Maintaining separate OCM and metathesis separation modules can be advantageous in some instances (in contrast with integrated separations) with respect to the simplicity of operation, sizing of various equipment and economic implications thereof.

In some instances, a metathesis unit integrated with an OCM system can have a common separations and purification system where the product stream from the metathesis unit is routed to the $C_2$ separations section of the OCM module (de-ethanizer). The de-ethanizer overhead can be sent to the $C_2$ splitter to generate polymer grade ethylene and an ethane product. The ethane product can be recycled to the OCM reactor. A part of the ethylene produced can be sent to the dimerization reactor and the remaining ethylene is sent to the metathesis unit. The de-ethanizer bottoms stream can be sent to a de-propanizer, followed by a $C_3$ splitter to produce (polymer grade) propylene. The de-propanizer bottoms can be sent to a de-butanizer or a de-pentanizer to recover a $C_4$ raffinate. In some cases, the butene rich stream from dimerization reactor can be isomerized in a reactive distillation section to convert butene-1 to butene-2 and separate the butene-2 for the metathesis reactor. The debutanizer overhead may be the C4 feed to the metathesis reactor and may be routed to the metathesis unit. Some treatment may be required to ensure the feed purity to the metathesis unit as the catalysts may be very sensitive to impurities.

In some cases, the $C_4$ rich stream can be sourced from a refinery or a steam cracker. The C4 stream can also be a crude C4 mix stream or a raffinate I or a raffinate II stream. These C4 streams can be sufficient to provide for the C4 requirement of the metathesis unit with no dimerization required. In some cases, the $C_4$ stream can be mixed with the $C_4$ stream from the dimerization reactor. In either case (i.e., dimerization alone, dimerization plus off gas recovery or only off gas processing), the $C_4$ processing can also include either a selective hydrogenation unit (SHU) to hydrogenate any $C_4$ dienes to olefins, or a butadiene recovery unit or a reactive distillation unit or a total hydrogenation unit to hydrogenate the remaining $C_4$s after butene-2 has been utilized. In some cases, the final product is a $C_4$ LPG/$C_4$ raffinate containing butanes, and unreacted butenes.

A raffinate stream can directly be fed to the debutanizer in the unit, from where the overhead can be routed to the metathesis reactor. The overhead should be predominantly a butene rich stream. The higher the butene content, lower is the $C_4$ purge from the system, and lower are the recycle rates. If a mixed crude $C_4$ stream is available, it can either be subjected to selective hydrogenation unit where the diolefins (butadienes) may be hydrogenated to butenes, or sent to a butadiene recovery unit to recover the butadiene. This may depend on the feed composition and the economics of the particular location and the petrochemical complex configuration. The $C_4$ purge stream that contains unreacted butenes, butanes and some other $C_4$s, can be either sent to a refinery or hydrogenated and sent to a cracking furnace or sold as a $C_4$ stream.

In some cases, a $C_{5+}$ stream can be added to the system (e.g., to the debutanizer). The addition of $C_5$ components (e.g., pentenes) can further increase the yield of propylene, as the additional pentenes can be converted to ethylene and propylene in the system.

The integration described herein (e.g., OCM+dimerization+metathesis+polypropylene) can yield many advantages from a process and economic standpoint. The combined system can have a common separations and recovery system, a common refrigeration system, and take advantage of an integrated site with respect to utilities and off-sites. Additionally, the OCM system can generate excess steam for the entire system.

Operational Flexibility:

The combined system comprising OCM, dimerization, metathesis, polypropylene unit and an option to import C4 stream may provide immense operational flexibility which can produce attractive economic returns. All the units can operate at capacity to produce polymer grade propylene, or polypropylene product. The ethylene produced from OCM can be routed to the dimerization unit if the C4s are not available (or are not available as per the entire C4 demand of metathesis). Alternatively or additionally, the ethylene produced from the OCM can be, wholly or in part be sold as a polymer grade ethylene product. In the event of high value for butenes, the dimerization unit can be operated without the metathesis unit and the butenes can be exported as a product. The system can in effect, produce polymer grade ethylene, polymer grade propylene, mixed butenes stream, in the desired ratio depending on the market conditions, feedstock availability and the product demand. The feedstock may be natural gas, which makes the system a highly desirable gas monetizing option.

In some cases, the product can be butadiene. An OCM unit can be operated with a dimerization unit, where the dimerization unit is designed to selectively produce butene-1, and the butene-1 can be fed to a C4 dehydrogenation unit to produce butadiene.

In some cases, the dimerization unit can produce 1-butene as the main product, and the 1-butene product can be used as a separate product and/or as a co-monomer in linear low-density poly ethylene production, or used as a feedstock to produce butadiene by oxidative dehydrogenation of 1-butene, or produce polypropylene resins, butylene oxide, or secondary butyl alcohol (SBA) or methyl ethyl ketone (MEK).

Additionally, ethylene from an OCM process can be supplied as a co-monomer for polypropylene production (e.g., 8-15% ethylene co-monomer). A separations section of an OCM process can handle the recycle streams from a metathesis unit and a polypropylene unit in addition to the separations for the OCM process itself.

Figure 5:
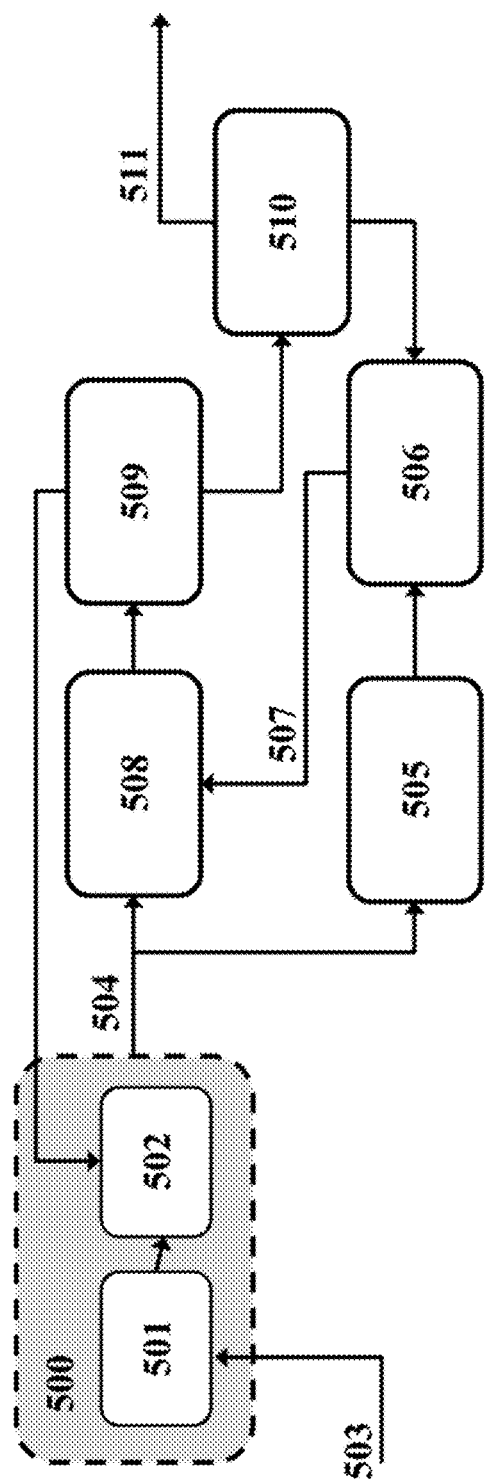
FIG. 5 shows a schematic illustration of an example OCM process integrated with dimerization and a metathesis-based propylene production process.

For example, FIG. 5 shows an example schematic for integration of OCM with metathesis for propylene production. An OCM unit 500 with an OCM reactor 501 and a separations section 502 receives a methane stream 503 (e.g., natural gas) and produces an ethylene product stream 504 (e.g., polymer-grade ethylene). A portion of the ethylene stream can be directed into a dimerization reactor 505 to produce $C_4$ products, which can then be separated in a $C_4$ separation unit 506. Butene-2 507 from the $C_4$ separation unit can be directed into a metathesis reactor 508 along with ethylene from the OCM unit. The metathesis product stream can be directed to a $C_2$ separation unit 509, with $C_2$ compounds being sent as a recycle stream to the OCM unit separations section. $C_{3+}$ compounds can be directed from the $C_2$ separations unit to a $C_3$ separations unit 510. Propylene 511 can be recovered from the $C_3$ separations unit, with $C_{4+}$ compounds directed to the $C_4$ separation unit.

Figure 6A:
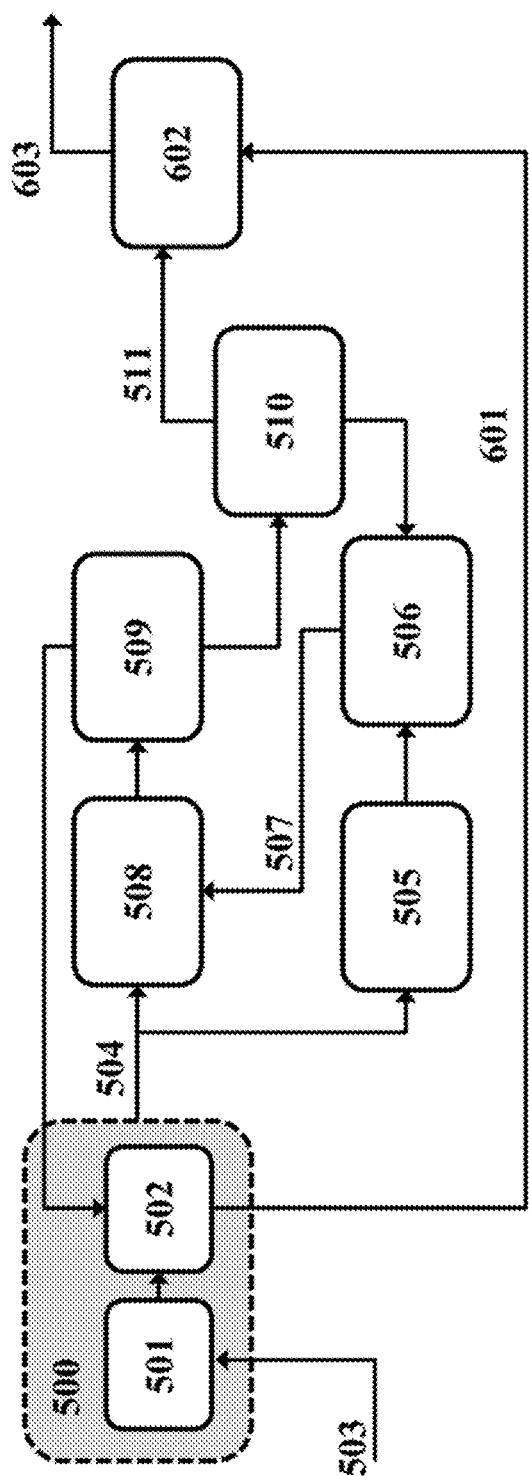
FIG. 6A shows a schematic illustration of an example OCM process integrated with dimerization and a metathesis-based propylene production process with polypropylene production.

Propylene can be further processed into polypropylene. For example, FIG. 6A shows the propylene 511 being directed, along with ethylene co-monomer 601 from the OCM unit, into a polypropylene unit 602 to produce polypropylene 603. Polypropylene production can be an optional addition to the process shown in FIG. 5.

Figure 6B:
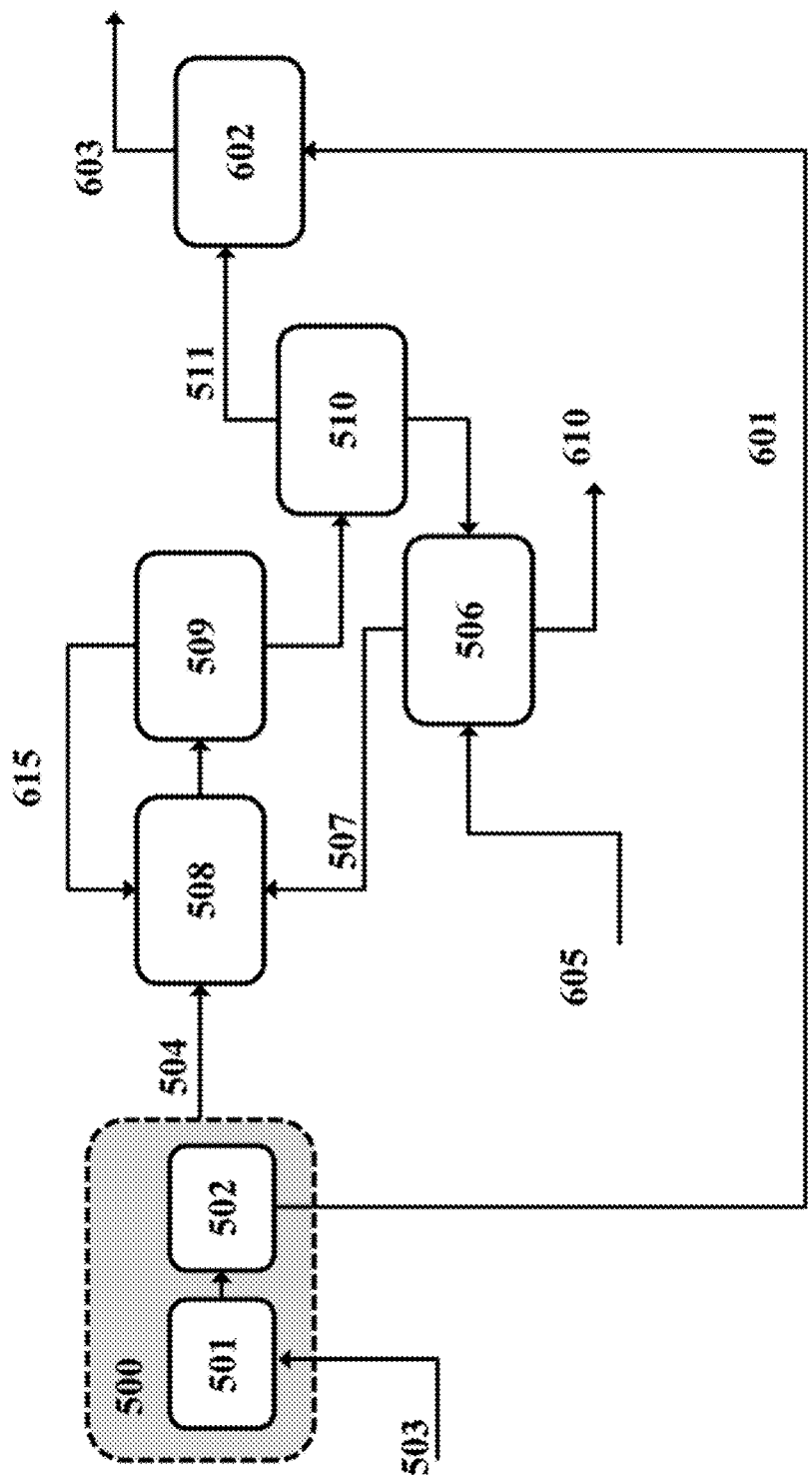
FIG. 6B shows a schematic illustration of an example OCM process integrated with a metathesis unit to produce propylene using an external C4 feedstock.

FIG. 6B shows an example system where enough $C_4$ compounds are available (e.g., as a $C_4$ raffinate stream, as a crude $C_4$ stream, as a concentrated butene stream, or any combination thereof), such that the dimerization unit is no longer required to provide the $C_4$ compounds for metathesis. As shown in FIG. 6B, where like-numbered elements correspond to those in FIG. 6A, the ethylene 504 from the OCM unit 500 can be directly routed to the metathesis reactor 508, with a part of the ethylene optionally being routed to the polypropylene unit 602 to be used as a co-monomer. The external $C_4$ stream 605 can enter the process at various locations including to the debutanizer 506 where the overhead butene rich stream 507 can be sent to the metathesis reactor. In some cases, e.g., depending on the iso-butene and butadiene content of the external $C_4$ stream, the external $C_4$ stream can be treated further, which is not shown in the FIG. 6B. In some cases, the external $C_4$ stream is fed directly to the metathesis unit 508. In some cases, the process can produce a $C_{5+}$ product stream 610. In some cases, a recycle stream 615 from the $C_2$ separation unit 509 can be returned directly to the metathesis reactor 508 (i.e., rather than the OCM separations module 502).

In some cases, the recovery systems are integrated. For example, with reference to FIG. 7A, a case is shown having a $C_2$ splitter 700 that produces enriched ethylene 701 for the metathesis unit 702 and/or the dimerization unit 704. In some cases, the enriched ethylene is polymer-grade ethylene (which can also be used as a co-monomer in the production of polypropylene). In some instances, the $C_2$ splitter 700 is not operated at conditions that result in polymer-grade ethylene. The enriched ethylene stream can comprise greater than or equal to about 60%, about 70%, about 80%, about 90%, about 95%, about 99%, or more ethylene by mass.

Figure 7A:
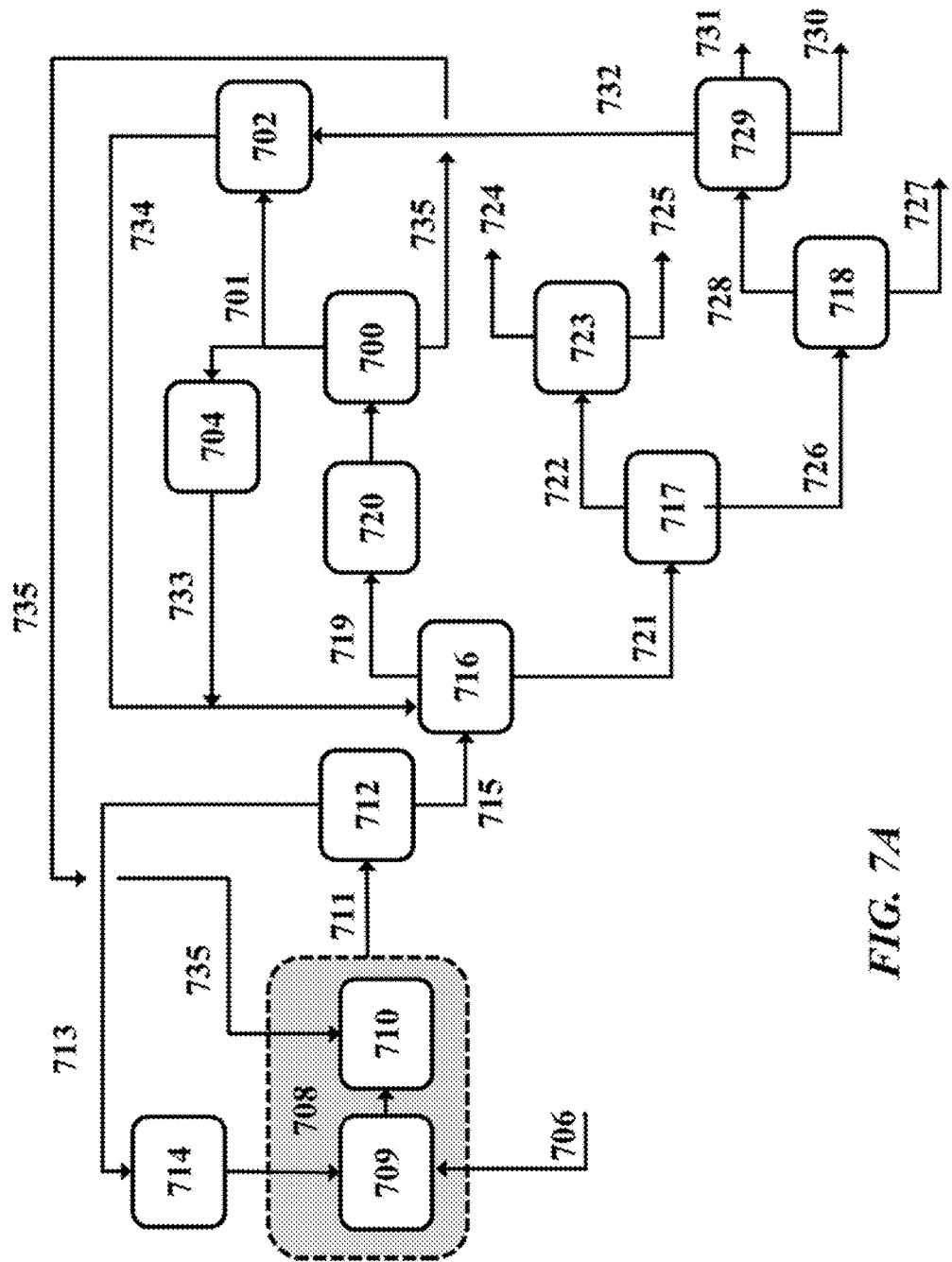
FIG. 7A shows a schematic illustration of an example OCM process integrated with dimerization and a metathesis-based propylene production process having a $C_2$ splitter.

Continuing with FIG. 7A, reactants 706 (i.e., methane and $O_2$) can be fed into an OCM reactor 708 having a catalyst bed 709 and an ethane conversion section 710. The OCM reactor can produce an OCM effluent 711 that goes to a de-methanizer 712. In some cases, there are additional units in the OCM process that are not shown, such as compressors, $CO_2$ removal units, drying units, desulfurization units, quenchers and heat exchangers. The de-methanizer overhead 713 can contain $C_1$ compounds and go to a methanation unit 714 for conversion into methane and recycle to the OCM reactor 708. As used herein, the terms "overhead" and "bottoms" do not limit the portion of the separation column from which the stream emerges (e.g., in some cases, the "bottoms" can come out of the middle or top of the separation column).

Figure 7B:
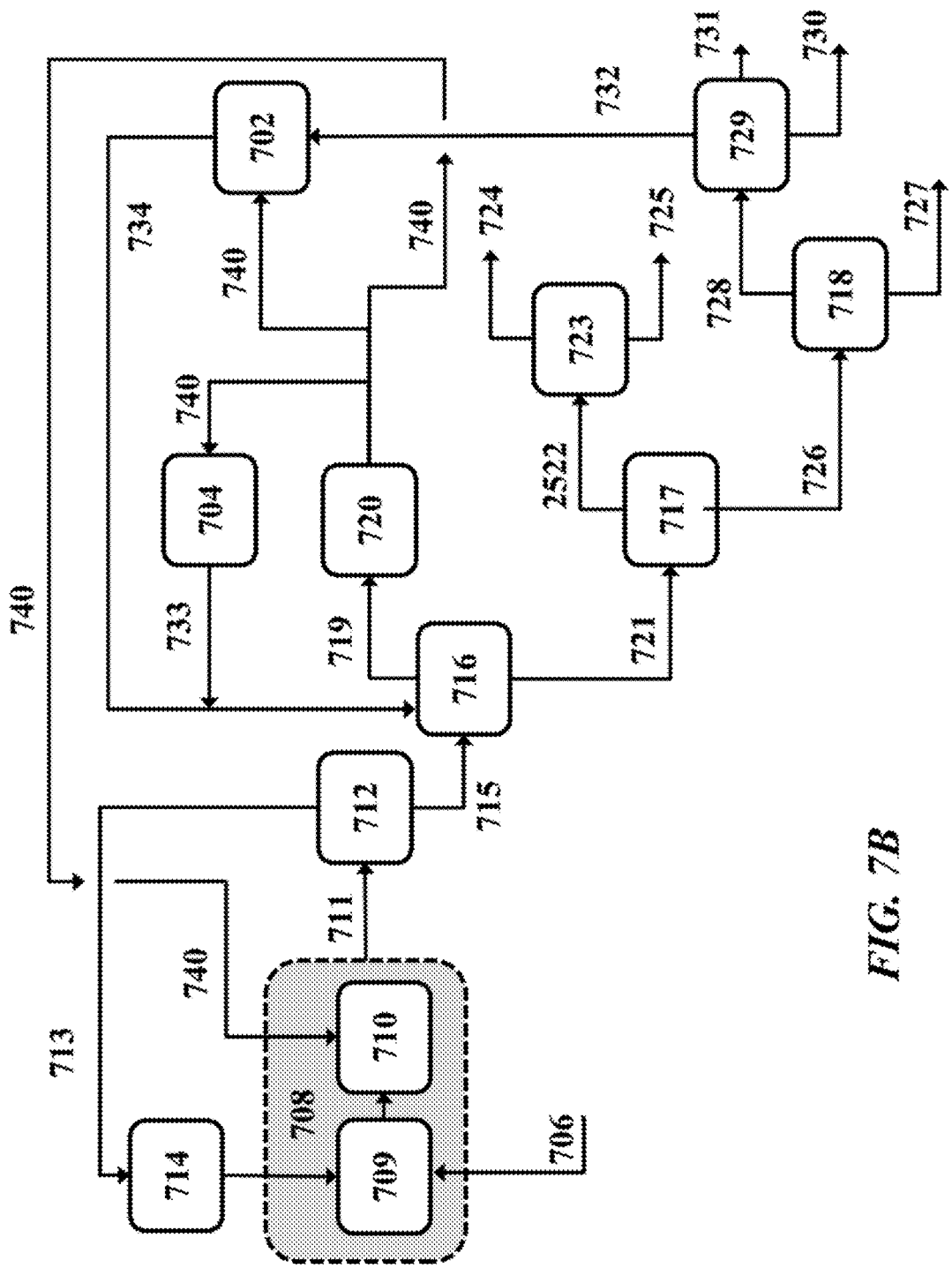
FIG. 7B shows a schematic illustration of an example OCM process integrated with dimerization and a metathesis-based propylene production process without a $C_2$ splitter.

The de-methanizer bottoms 715 can include $C_{2+}$ compounds and continue into a fractionation train including a de-ethanizer 716, a de-propanizer 717 and a de-butanizer 718. The de-ethanizer overhead 719 can contain $C_2$ compounds and go to a hydrogenation unit 720, which hydrogenation unit can (selectively) hydrogenate acetylene. As described herein, the $C_2$ compounds can be separated into an enriched ethylene stream (e.g., using the $C_2$ splitter 700), or not separated as shown in FIG. 7B.

The de-ethanizer bottoms 721 can contain $C_{3+}$ compounds and be taken to the de-propanizer 717. The de-propanizer overhead 722 can contain $C_3$ compounds that can be split in a $C_3$ splitter 723 into propane 724 and propylene 725. In some cases, the propylene is polymer-grade. In some cases, the propylene is used to make polypropylene (optionally with an ethylene co-monomer, such as derived from the present process, i.e., from the $C_2$ splitter 700). In some cases, the propylene 725 is at least about 85%, about 90%, about 95%, about 99%, about 99.5%, about 99.9%, about 99.95%, or more pure.

The de-propanizer bottoms 726 can contain $C_{4+}$ compounds and be directed to a de-butanizer 718. The de-butanizer can produce a bottoms stream 727 that includes $C_{5+}$ compounds and an overhead stream 728 comprising $C_4$ compounds, which $C_4$ compounds can be sent to a $C_4$ splitter 729. The $C_4$ splitter can produce a plurality of streams (i.e., 730, 731 and 732) including a stream enriched in butene-2 732. In some cases, the butene-2 732 is at least about 85%, about 90%, about 95%, about 99%, about 99.5%, about 99.9%, or about 99.95% pure. The butene-2 732 can go to the metathesis unit 702.

Additional butene-2 733 can be produced from the dimerization module 704 (e.g., from ethylene). The additional butene-2 733 can be used directly in the metathesis reactor 702 in some cases. However, as shown here, the additional butene-2 can be recycled to the fractionation train (e.g., to the de-ethanizer 716) to enrich the concentration of butene-2 prior to metathesis. In some cases, the C4 mix product from the dimerization reactor is sent to the debutanizer since the dimerization reactor effluent may comprise C4 components. Also, the product stream 733 can be a mix of butenes (butene-2, butene-2, n-butenes, iso-butenes) or can be a pure butene-2 rich stream.

The metathesis unit can produce a propylene stream 734 that can be utilized directly or enriched (e.g., to polymer grade propylene) by recycling the dilute propylene stream 734 to the fractionation train (e.g., to the de-ethanizer 716).

The process can produce a number of additional streams that can be utilized directly or recycled in the process, such as an ethane stream 735 coming from the $C_2$ splitter that can be recycled to the catalyst bed 709 and/or ethane conversion section 710 of the OCM reactor 708.

In some cases, the $C_2$ compounds are not split into enriched ethylene or enriched ethane streams. With reference to FIG. 7B, the de-ethanizer overhead 719 can be used in the metathesis module 702, in the dimerization module 704, and/or can be recycled to the OCM reactor 708 directly (e.g., without first being separated in a $C_2$ splitter). In some cases, the $C_2$ stream 719 can go through a hydrogenation unit 720 (e.g., that hydrogenates acetylene) to produce a hydrogenated $C_2$ stream 740, which hydrogenated $C_2$ stream 740 can be used in the metathesis module 702, in the dimerization module 704. In some cases, the hydrogenated $C_2$ stream 740 can contain at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more compounds other than ethylene.

Figure 8:
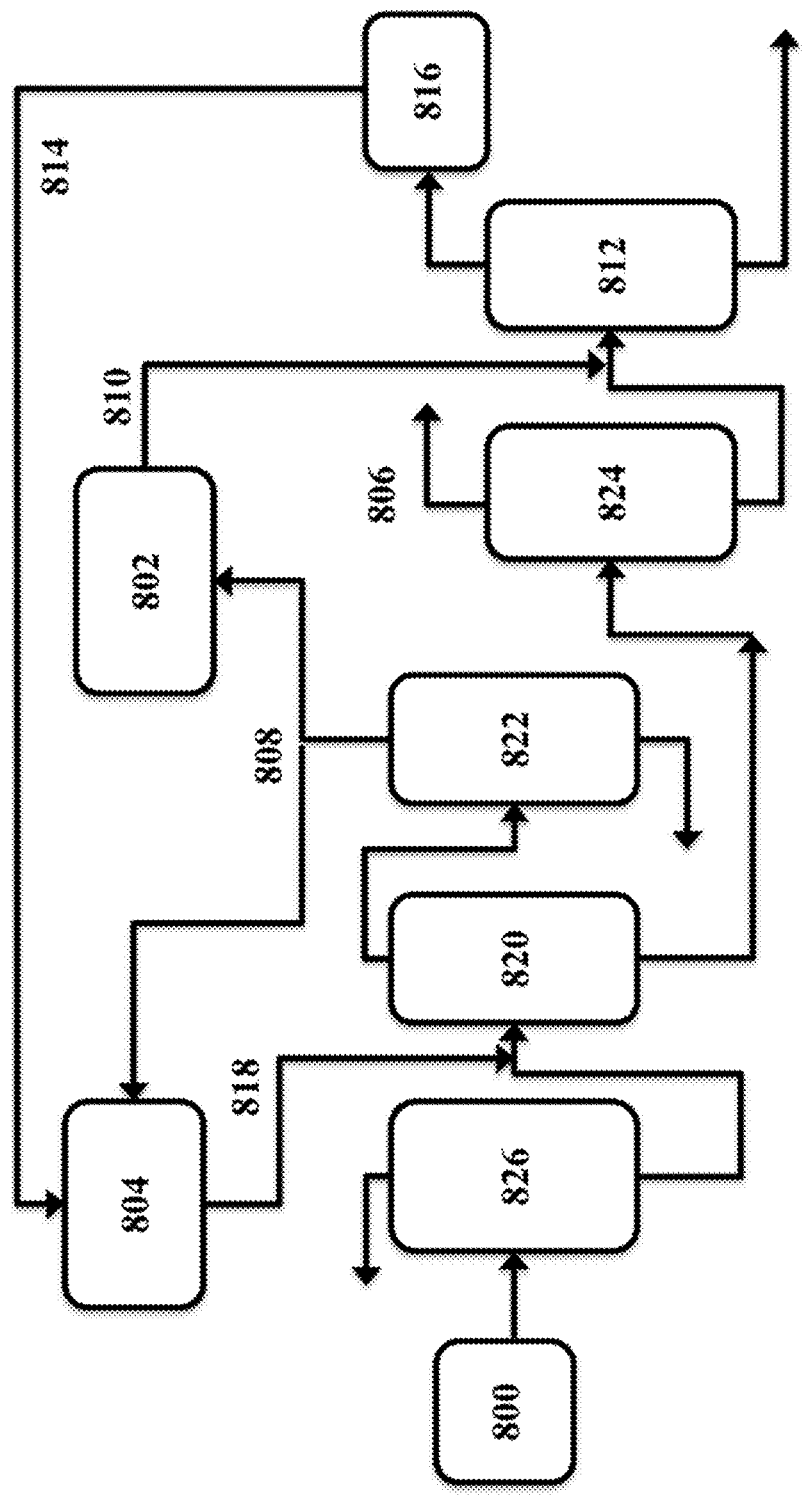
FIG. 8 shows a schematic illustration of an example OCM process integrated with a dimerization, metathesis and polypropylene unit, with integrated separation section and an optional C3 splitter.

FIG. 8 shows an example of an integrated plant having OCM 800, dimerization 802 and metathesis 804. The C3 product 806 can be used for polypropylene production. The polymer grade ethylene stream 808 can be routed to the dimerization and the metathesis unit. The dimerization effluent 810, which may comprise predominantly C4s stream can be sent to the debutanizer 812. The mix butenes rich debutanizer overhead 814 can be routed to the metathesis reactor 804 via a feed treater 816 that can remove any potential poisons for the metathesis catalysts. The metathesis reactor effluent 818 can comprise propylene, some unreacted C4s and ethylene. The metathesis effluent can be routed to the de-ethanizer 820, the de-ethanizer overhead can be sent to the C2 splitter 822 for ethylene recovery. The de-ethanizer bottoms can be routed to the de-propanizer 824, the de-propanizer overhead 806 can contain greater than about 95% propylene. In some cases, a C3 splitter (not shown) can be used to further purify the C3 overhead to polymer grade propylene. In some cases, a C3 splitter can be installed in the system to produce high purity polymer grade propylene. A de-methanizer 826 can recover non-reacted methane from the OCM product.

Mixing Devices, Systems and Methods

Recognized herein is the need for systems and methods for converting methane to higher chain hydrocarbons, such as hydrocarbon compounds with two or more carbon atoms (also "$C_{2+}$ compounds" herein), in an efficient and/or commercially viable process. An oxidative coupling of methane ("OCM") reaction is a process by which methane can form one or more $C_{2+}$ compounds.

In an aspect of the present disclosure, pre-conditioning of OCM reactant streams may be achieved by mixing using mixer devices, systems and methods for OCM processes. Such devices or systems can (i) mix the methane-containing and oxygen-containing streams with the required degrees of uniformity in terms of temperature, composition and velocity; and/or (ii) mix the methane-containing and oxygen-containing streams substantially completely, rapidly and efficiently in order to minimize the residence time of the heated mixed gases before they can be contacted with and reacted in the catalyst bed, which may be less than, or substantially less than the amount of time for autoignition of the mixed heated gases to occur.

Required composition uniformity can be such that the deviation of the most oxygen-rich and oxygen-poor post-mixing areas in terms of $CH_4/O_2$ ratio is less than or equal to about 50%, 40%, 30%, 20%, 15%, 10%, 5%, 4%, 3%, 2%, 1%, or less, as compared to a perfectly mixed stream. Required temperature uniformity can be such that the deviation of the hottest and coldest post-mixing zones from the temperature of the ideally mixed stream is less than or equal to about 30° C., 20° C., 10° C., 5° C., or less. Required velocity uniformity can be such that the deviation in flow of the post-mixing areas with the largest and smallest flow from the flow of the ideally mixed stream is less than or equal to about 50%, 40%, 30%, 20%, 15%, 10%, 5%, 4%, 3%, 2%, 1%, or less. Any larger deviations of these variables from the average may cause the catalytic bed located downstream of the mixer to perform with a reduced efficiency. Mixers of the present disclosure can aid in achieving a desired degree of compositional, pressure, temperature and/or flow uniformity in a time period lower than the auto-ignition delay time, such as within a time period from about 5 milliseconds (ms) to 200 ms and/or a range of flow rates from about 1 Million standard cubic feet per day (MMSCFD) to 2,000 MMSCFD. In some cases, the auto-ignition delay time is from about 10 milliseconds (ms) to 1000 ms, or 20 ms to 500 ms, at a pressure from about 1 bar (absolute) and 100 bars, or 1 bar to 30 bars, and a temperature from about 300° C. to 900° C., or 400° C. and 750° C.

If any portion of the mixed stream is allowed to spend longer than the auto-ignition delay time in the mixing zone before coming in contact with a catalyst in the OCM reactor, this particular portion can auto-ignite and propagate combustion throughout the entire stream. In some cases, 100% of the stream spends less than the auto-ignition time, which may require the mixer to be characterized by a substantially narrow distribution of residence times and the absence of a right tail in the distribution curve beyond the auto-ignition threshold. Such a mixer can provide a non-symmetric distribution of residence times.

An aspect of the present disclosure provides an oxidative coupling of methane (OCM) process comprising a mixing member or device (or mixer) in fluid communication with an OCM reactor. The mixer is configured to mix a stream comprising methane and a stream comprising oxygen to yield a stream comprising methane and oxygen, which is subsequently directed to the OCM reactor to yield products comprising hydrocarbon compounds. The hydrocarbon compounds can subsequently undergo separation into various streams, some of which can be recycled to the mixer and/or the OCM reactor.

The hydrocarbon compounds can include compounds with two or more carbon atoms ($C_{2+}$ compounds). The hydrocarbon compounds can include $C_{2+}$ compounds at a concentration (e.g., mole % or volume %) of at least about 5%, 10%, 20%, 30%, 40%, 50%, 60%, 70%, 80%, 90%, 95%, 99%, or more. In some situations, the hydrocarbon compounds substantially or exclusively include $C_{2+}$ compounds, such as, for example, $C_{2+}$ compounds at a concentration of at least about 60%, 70%, 80%, 90%, 95%, 99%, 99.9%, or more.

Mixing can be employed in a mixer fluidically coupled to an OCM reactor. The mixer can be integrated with the OCM reactor, or be a standalone unit. In some examples, the mixer is upstream of the OCM reactor. In other examples, the mixer is at least partly or substantially integrated with the OCM reactor. For example, the mixer can be at least partly or substantially immersed in a reactor bed of the OCM reactor. The reactor bed can be a fluidized bed.

Systems and methods of the present disclosure can maximize the efficiency of an OCM reaction and reduce, if not eliminate, undesired reactions.

Fluid properties can be selected such that methane and an oxidizing agent (e.g., $O_2$) do not auto-ignite at a location that is before the catalyst of the OCM reactor. For instance, a stream comprising methane and oxygen can have a composition that is selected such that at most 5%, 4%, 3%, 2%, 1%, 0.1%, 0.01%, or less of the oxygen in the mixed gas stream auto-ignites. The fluid properties include the period of time in which methane is in contact with oxygen (or another oxidizing agent). The residence time can be minimized so as to preclude auto-ignition. In some cases, the stream comprising methane and oxygen can have a substantially non-symmetric distribution of residence (or delay) times along a direction of flow of said third stream. The residence (or delay) time is the period in which a stream comprising methane and oxygen does not auto-ignite. In some examples, the distribution of residence times is skewed towards shorter residence times, such as from about 5 ms to 50 ms. Auto-ignition delay time may be primarily a function of temperature and pressure and, secondarily, of composition. In some cases, the higher the pressure or the temperature, the shorter the auto-ignition delay time. Similarly, the closer the composition to the stoichiometry required for combustion, the shorter the auto-ignition delay time. Diagrams based on empirical data and thermodynamic correlations may be used to determine i) the auto-ignition region (i.e., the threshold values of temperature, pressure and composition above or below which auto-ignition may occur); and ii) the auto-ignition delay time inside the auto-ignition region. Once the auto-ignition delay time is determined for the desired or otherwise predetermined operating conditions, the mixer may be designed such that 100% of the mixed stream spends less than the auto-ignition time in the mixer itself prior to contacting the OCM catalyst.

During mixing, flow separation may cause a portion of the flow to spend a substantially long period of time in a limited region due to either the gas continuously recirculating in that region or being stagnant. In some cases, flow separation causes this portion of the flow to spend more time than the auto-ignition time prior to contact with the catalyst, thus leading to auto-ignition and propagation of the combustion to the adjacent regions, and eventually, to the entire stream.

Mixers of the present disclosure may be operated in a manner that drastically reduces, if not eliminates, flow separation. In some situations, fluid properties (e.g., flow regimes) and/or mixer geometries are selected such that upon mixing a stream comprising methane with a stream comprising oxygen in a mixer flow separation does not occur between the mixer and the first gas stream, the second gas stream, and/or the third gas stream.

Figure 9:
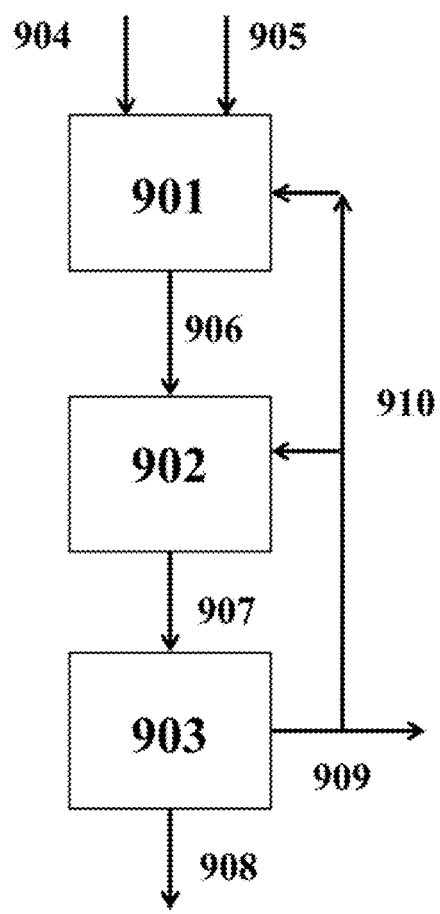
FIG. 9 schematically illustrates an example system for the oxidative coupling of methane (OCM)

FIG. 9 shows an OCM system 900 comprising a mixer 901, an OCM reactor 902 downstream of the mixer 901, and a separation unit 903 downstream of the OCM reactor 902. The arrows indicate the direction of fluid flow. A first fluid stream ("stream") 904 comprising methane ($CH_4$) and a second fluid stream 905 comprising oxygen ($O_2$) may be directed into the mixer 901, where they may be mixed to form a third mixed gas stream 906 that is directed into the OCM reactor 902. The second fluid stream 905 may comprise $CH_4$ (e.g., natural gas) and $O_2$ mixed and maintained at a temperature below the auto-ignition temperature. In some cases, diluting pure $O_2$ with methane may be desirable to enable relatively simpler material of construction for the mixer compared to situations in which pure $O_2$ is used. In situations where pure $O_2$ is used, materials such as Hastelloy X, Hastelloy G, Nimonic 90, and others should be used as they are high temperature stable and resist metal ignition in oxygen environments. Such restrictions may be relaxed in the case of oxygen diluted with methane. In the OCM reactor 902, methane and oxygen may react in the presence of a catalyst provided within reactor 902, to form $C_{2+}$ compounds, which are included in a fourth stream 907. The fourth stream 907 can include other species, such as non-$C_{2+}$ impurities like Ar, $H_2$, CO, $CO_2$, $H_2O$, $N_2$, $NO_2$ and $CH_4$. The fourth stream 907 may then be optionally directed to other unit operations for processing the outlet gas stream 907, such as separation unit 903, used for separation of at least some, all, or substantially all of the $C_{2+}$ compounds from other components in the fourth stream 907 to yield a fifth stream 908 and a sixth stream 909. The fifth stream 908 can include $C_{2+}$ compounds at a concentration (e.g., mole % or volume %) that is at least about 10%, 20%, 30%, 40%, 50%, 60%, 70%, 80%, 90%, 95%, 99%, or more, and the sixth stream 909 can include $C_{2+}$ compounds at a concentration that is less than or equal to about 99%, 95%, 90%, 80%, 70%, 60%, 50%, 40%, 30%, 20%, 10%, or less. The concentration of $C_{2+}$ compounds in the fifth stream 908 can be higher than the concentration of $C_{2+}$ compounds in the sixth stream 909. The sixth stream 909 can include other species, such as Ar, $H_2$, CO, $CO_2$, $H_2O$, $N_2$, $NO_2$ and $CH_4$. The fifth stream and the sixth stream can have different ethylene to ethane ratios. At least some, all or substantially all of $CH_4$ in the sixth stream 909 may optionally be recycled to the mixer 901 and/or the OCM reactor 902 in a seventh stream 910. Ethane and/or propane can also be recycled. Propane, for example, can be recycled using a $C_3$ splitter. A separations unit can comprise reactive separations units, such as an ethylene-to-liquids reactor. Although illustrated in FIG. 9 as a separate unit operation, the mixer component of the system may be integrated into one or more unit operations of an overall OCM process system. For example, in some cases, mixer 901 is an integrated portion of reactor 902, positioned immediately adjacent to the catalyst bed within the reactor 902, so that that the mixed gas stream 906 may be more rapidly introduced to the reactor's catalyst bed, in order to minimize the residence time of mixed stream 906.

Methane in the first fluid stream 904 can be provided from any of a variety of methane sources, including, e.g., a natural gas source (e.g., natural gas reservoir) or other petrochemical source, or in some cases recycled from product streams. Methane in the first fluid stream may be provided from an upstream non-OCM process.

The product stream 908 can be directed to one or more storage units, such as $C_{2+}$ storage. In some cases, the product stream can be directed to a non-OCM process.

Fluid properties (e.g., flow regimes) may be selected such that optimum mixing is achieved. Fluid properties can be selected from one or more of flow rate, temperature, pressure, and concentration. Fluid properties can be selected to achieve a given (i) temperature variation in the third stream 906, (ii) variation of concentration of methane to the concentration of oxygen in the third stream 906, and/or (iii) variation of the flow rate of the third stream 906. Any one, two or all three of (i)-(iii) can be selected. In some cases, the temperature variation of the third stream 906 is less than or equal to about 100° C., 90° C., 80° C., 70° C., 60° C., 50° C., 40° C., 30° C., 20° C., 10° C., 5° C., 1° C., or less. The variation of the concentration of methane to the concentration of oxygen ($CH_4/O_2$) in the third stream 906 can be less than about 50%, 40%, 30%, 20%, 15%, 10%, 5%, 4%, 3%, 2%, 1%, or less compared to a perfectly mixed (or ideal) stream. The variation of the flow rate of the third stream 906 can be less than about 50%, 40%, 30%, 20%, 15%, 10%, 5%, 4%, 3%, 2%, 1%, or less. Such variations can be as compared to a perfectly mixed or thermally equilibrated stream and may be taken along a direction that is orthogonal to the direction of flow. Variations can be measured at the exit plane of 906, for example.

The mixer 901 can mix the first stream 904 and the second stream 905 to generate a stream characterized by uniform or substantially uniform composition, temperature, pressure and velocity profiles across a cross section of a mixing zone of the mixer 901 or reactor 902 (e.g., along a direction that is orthogonal to the direction of flow). Uniformity can be described in terms of deviation of the extremes from an average profile. For example, if the various streams possess different temperatures, the resulting profile of the mixed stream can show a maximum deviation of +/−1 to 20° C. between the hottest and coldest areas compared to the ideal (e.g., perfectly mixed) stream. Similarly, if the various streams possess different compositions, the resulting profile of the mixed stream may show a maximum deviation of +/−0.1 to 20 mole % of all reacting compounds compared to the composition of the ideal stream. Similar metrics can be used for velocity and pressure profiles.

In some cases, the system 900 can include at least about 1, 2, 3, 4, 5, 6, 7, 8, 9, or 10 separation units. For example, the system 900 may include one separation unit 903. The separation unit 903 can be, for example, a distillation column, scrubber, or absorber. In cases where the system 900 includes multiple separation units 903, the separation units 903 can be in series and/or in parallel.

The system 900 can include any number of mixers and OCM reactors. The system 900 can include at least about 1, 2, 3, 4, 5, 6, 7, 8, 9, or 10 mixers 901. The system 900 can include at least about 1, 2, 3, 4, 5, 6, 7, 8, 9, or 10 reactors 902. The mixers 901 can be in series and/or in parallel. The reactors 902 can be in series and/or in parallel.

Although described for illustration of preferred aspects as gas streams passing into, through and out of the reactor systems in FIG. 9, it will be appreciated that the streams 904, 905, 906, 907, 908, 909 and 910 can be gaseous streams, liquid streams, or a combination of gaseous and liquid streams. In some examples, the streams 904 and 905 are gaseous streams, and the stream 908 and 909 are liquid streams. In some examples, the streams 904, 905, and 909 are gaseous streams, and the stream 908 is a liquid stream.

In some cases, the system 900 includes multiple OCM reactors 902. The OCM reactors 902 can be the same, similar or dissimilar reactors or reactor types arranged in series or parallel processing trains.

The OCM reactor 902 can include any vessel, device, system or structure capable of converting at least a portion of the third stream 906 into one or more $C_{2+}$ compounds using an OCM process. The OCM reactor 902 can include a fixed bed reactor where the combined methane/oxygen gas mixture is passed through a structured bed, a fluidized bed reactor where the combined methane/oxygen mixture is used to fluidize a solid catalyst bed, and/or a membrane type reactor where the combined methane/oxygen mixture passes through an inorganic catalytic membrane.

The OCM reactor 902 can include a catalyst that facilitates an OCM process. The catalyst may include a compound including at least one of an alkali metal, an alkaline earth metal, a transition metal, and a rare-earth metal. The catalyst may be in the form of a honeycomb, packed bed, or fluidized bed.

Although other OCM catalysts can be disposed in at least a portion of the OCM reactors 902, in some cases, at least a portion of the OCM catalyst in at least a portion of the OCM reactor 902 can include one or more OCM catalysts and/or nanostructure-based OCM catalyst compositions, forms and formulations described in, for example, U.S. Patent Publication Nos. 2012/0041246, 2013/0023709, 2013/0158322, 2013/0165728, and 2014/0274671, each of which is entirely incorporated herein by reference. Using one or more nanostructure-based OCM catalysts within the OCM reactor 902, the selectivity of the catalyst in converting methane to desirable $C_{2+}$ compounds can be about 10% or greater; about 20% or greater; about 30% or greater; about 40% or greater; about 50% or greater; about 60% or greater; about 65% or greater; about 70% or greater; about 75% or greater; about 80% or greater; or about 90% or greater.

In the OCM reactor 902, methane and $O_2$ are converted to $C_{2+}$ compounds through an OCM reaction. The OCM reaction (e.g., $2CH_4+O_2 \rightarrow C_2H_4+2H_2O$) may be exothermic ($\Delta H=-67$ kcals/mole) and may require substantially high temperatures (e.g., temperature greater than 700° C.). As a consequence, the OCM reactor 902 can be sized, configured, and/or selected based upon the need to dissipate the heat generated by the OCM reaction. In some cases, multiple, tubular, fixed bed reactors can be arranged in parallel to facilitate heat removal. At least a portion of the heat generated within the OCM reactor 902 can be recovered, for example the heat can be used to generate high temperature and/or pressure steam. Where co-located with processes requiring a heat input, at least a portion of the heat generated within the OCM reactor 902 may be transferred, for example, using a heat transfer fluid, to the co-located processes. Where no additional use exists for the heat generated within the OCM reactor 902, the heat can be released to the environment, for example, using a cooling tower or similar evaporative cooling device. OCM reactor systems useful in the context of the present invention may include those described in, for example, U.S. Patent Publication Nos. 2014/0107385 and 2015/0152025, each of which is incorporated herein by reference in its entirety for all purposes.

As described above, in certain aspects, a mixer device or system can be provided coupled to or integrated with an OCM reactor or reactor system. Such mixers are described in greater detail below.

In some cases, two or more different reactant streams are mixed rapidly and sufficiently for carrying out a reaction involving the two or more streams. In some cases, mixing may be substantially completely within a rapid timeframe within the mixer systems and devices described herein.

In some cases, two or more gaseous streams can be mixed in a mixer within a narrow window of time targeted to be less than the time in which autoignition may occur at the temperatures and pressures of the mixed gas streams. Such narrow window of time can be selected such that the streams are mixed before any OCM reaction has commenced. In some cases, the mixing time is no longer than the maximum residence time before auto-ignition occurs. The mixing time can be less than or equal to about 99%, 95%, 90%, 80%, 70%, 60%, 50% or less of the maximum residence time. Each and all portions of the mixed stream can spend nearly the requisite amount of time in a mixing zone of a mixer or reactor that is configured to effect mixing. If the reacting mixture spends more time, then undesired reactions, some-times irreversible, may take place, which may generate undesired products and possibly impede or prevent the formation of the desired products. Such undesired reactions may generate a greater proportion of non-$C_{2+}$ impurities than $C_{2+}$ compounds, which may not be desirable.

In some situations, in order for the optimal residence time to be achieved by each portion of the mixing stream, the distribution of the residence times in the mixing zone can be substantially narrow so as to reduce the possibility for even a small portion of the stream to spend less or more than the allowed time in the mixing area. Such phenomenon can occur if recirculation and/or stagnant areas are formed due to the design of the mixer itself. For example, if the mixing device is a perforated cylinder located in the mainstream of the larger gaseous stream, the cylinder itself can produce significant recirculation zones in the areas immediately downstream, thus generating a wide right tail in the statistical distribution of residence times. Systems and methods of the present disclosure can advantageously avoid such problems.

The present disclosure provides systems and methods for mixing reactant species (e.g., methane and $O_2$) prior to or during reaction to form $C_{2+}$ compounds, such as by an OCM reaction. In some examples, i) two or more gaseous streams may be mixed together within a certain time frame and with a given (e.g., minimum) degree of uniformity, and/or ii) the resulting mixed stream may afford a limited overall residence time and a narrow distribution of residence times before operating conditions of the stream are significantly affected by undesired chemical reactions. Prior to or during mixing, reactant species may be preheated.

Figure 10:
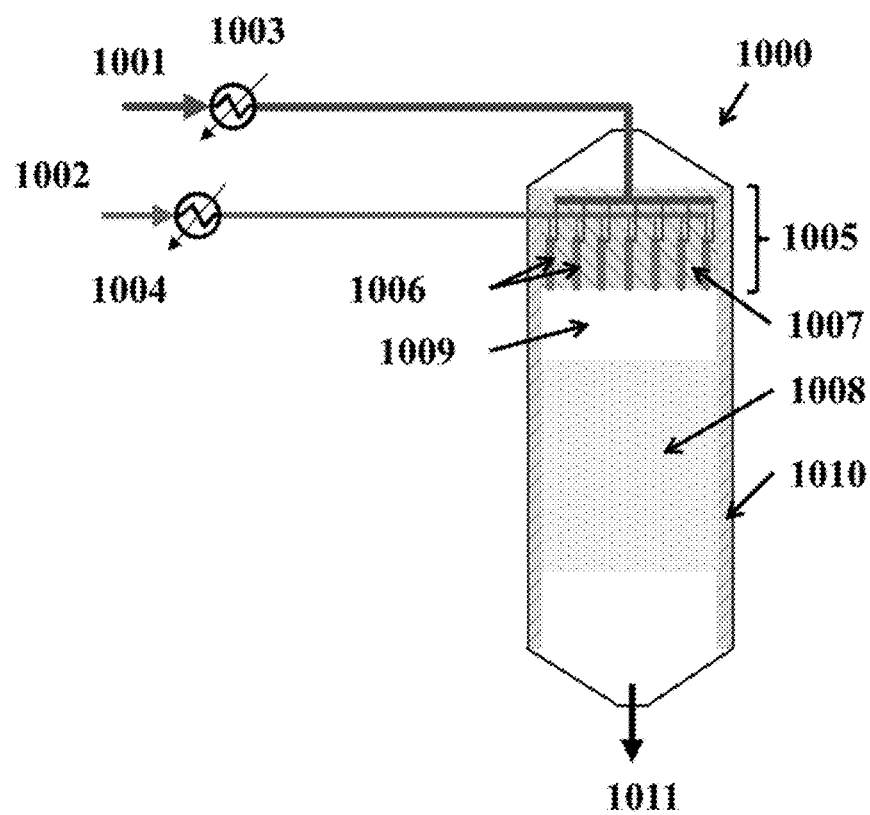
FIG. 10 shows an example OCM system comprising methane and oxygen containing gas streams.

A mixer can be integrated with an OCM reactor or separate from the OCM reactor, such as a standalone mixer. FIG. 10 shows an example OCM system 1000 comprising a methane stream 1001 and an air stream (comprising $O_2$) 1002 that are each directed through heat exchangers 1003 and 1004, where each of the streams 1001 and 1002 can be preheated. Next, the streams 1001 and 1002 may be directed to a mixer 1005 comprising a plurality of mixing nozzles 1006. The nozzles 1006 can be in two-dimensional array or in concentric circles, for example. The nozzles can each have the shape of an airfoil, as described elsewhere herein. Void space 1007 between the nozzles 1006 can be filled with a packing material (e.g., silica) to aid in preventing recirculation of the mixed gas.

The system 1000 may further comprise a catalyst bed 1008 downstream of the mixer 1005. The catalyst bed 1008 can include an OCM catalyst, as described elsewhere herein. A void space 1009 between the mixer 1005 and catalyst bed 1008 can be unfilled, or filled with an inert medium, such as, for example, aluminum oxide (e.g., alumina) or silicon oxide (e.g., silica) beads. In some cases, the void space can be filled with a material that increases the auto ignition delay time (AIDT), for example by changing the heat capacity of the media and/or interacting with the initial stage of combustion chemistry by scavenging highly reactive species that can act as combustion initiators. Suitable materials can include zirconia beads, ceramic foams, metal foams, metal or ceramic honeycomb structures, or combinations thereof. The use of materials that increase the AIDT can be advantageous at elevated pressures (e.g., above about 3, 5, 10, 15, 20, 25, 30, 35, or 40 barg). The system 1000 can include a reactor liner 1010 that can insulate the system 1000 from the external environment. The liner 1010 can thermally insulate the mixer 1005 and catalyst bed 1008 from the external environment.

In each nozzle 1006 of the mixer 1005, methane and air (including oxygen) can be mixed to form a mixed stream that is directed to the catalyst bed 1008. In the catalyst bed 1008, methane and oxygen mat react to form $C_{2+}$ compounds in an OCM process. The $C_{2+}$ compounds along with other compounds, such as unreacted methane and oxygen, may be directed out of the system 1000 in a product stream 1011.

Figure 11A:
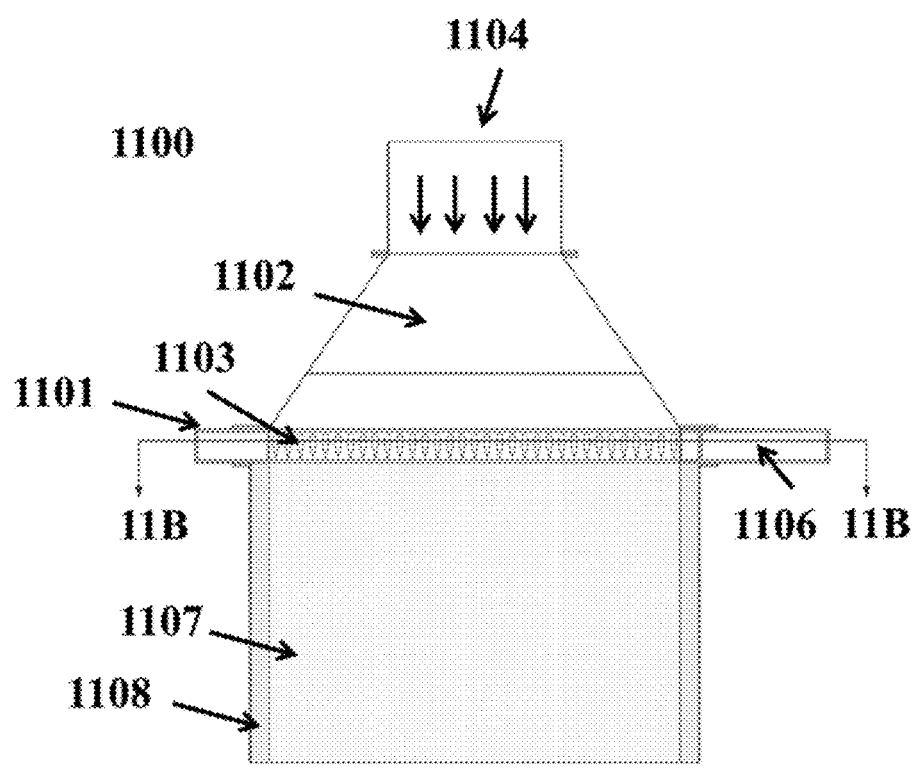
FIG. 11A shows a schematic side view of an example OCM reactor designed with an airfoil-shaped mixer.
Figure 11B:
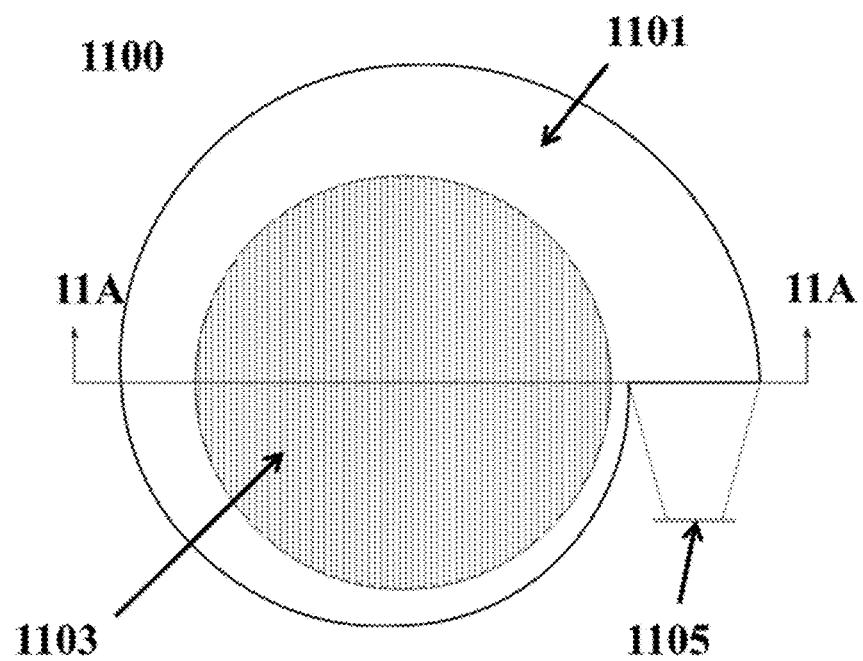
FIG. 11B shows a schematic cross sectional side view of an example OCM reactor designed with an airfoil-shaped mixer.

In some cases, mixers include one or more airfoils. FIGS. 11A and 11B show an example OCM system 1100 comprising a mixer (or injector) 1101 and a gas distribution manifold 1102 adjacent to the mixer 1101. FIG. 11B schematically illustrates a cross-section of the system 1100, taken along line 11B-11B in FIG. 11A. The mixer 1101 may comprise a plurality of ribs 1103 that are airfoils. An upstream portion of each of the ribs 1103 may have a larger cross-section than a downstream portion of each of the ribs 1103. The ribs 1103 may or may not be hollow.

In some cases, a mixer is capable of mixing a first gas (e.g., $CH_4$) and a second gas (e.g., $O_2$) within about 1,000 milliseconds (ms), 900 ms, 800 ms, 700 ms, 600 ms, 500 ms, 400 ms, 300 ms, 200 ms, 100 ms, 50 ms, 10 ms, or less. The mixer can include a plurality of manifolds, such as airfoil-shaped manifolds, distributed across a fluid flow path.

In FIGS. 11A and 11B, a first fluid stream may be directed into the gas distribution manifold 1102 at a first inlet 1104. A second fluid stream may be directed into the mixer 1101 at a second inlet 1105 (along the direction of the arrows (i.e., upstream do downstream), at which point the second fluid stream may be directed to along a fluid flow path 1106 to the ribs 1103. The fluid flow path 1106 can be a chamber that is in fluid communication with the inlet 1105 and the ribs 1103. In some examples, the first fluid stream comprises a hydrocarbon (e.g., methane) and the second fluid stream comprises an oxidizing agent. In some cases, the second fluid stream is air and the oxidizing agent is $O_2$.

The system 1100 may further comprise an OCM reactor 1107 downstream of the mixer 1101. The ribs 1103 are situated along a fluid flow path that leads from the inlet 1104 to the OCM reactor 1107. During use, the first fluid stream may enter the system 1100 at the inlet 1104 and may be directed to the gas distribution manifold 1102. The second fluid stream may enter the system 1100 at the inlet 1105 and may be directed along the fluid flow path 1106 to the ribs 1103. As the second fluid stream is directed along the fluid flow path, heat from the OCM reactor 1107 can heat the second fluid stream. The heated fluid stream may enter the ribs 1103 and may be directed out of the ribs to mix with the first fluid stream that is directed towards the OCM reactor 1107 from the gas distribution manifold 1102.

The mixer 1101 can be close coupled with the OCM reactor 1107. In some cases, the OCM reactor 1107 includes a catalyst. The catalyst may be included in a space between the ribs 1103. The OCM reactor 1107 can have various shapes and sizes. The OCM reactor 1107 can have a cross-section that is circular, oval, triangular, square, rectangular, pentagonal, hexagonal or any partial shape and/or combination thereof. In an example, the OCM reactor 1107 is cylindrical in shape. In some examples, the OCM reactor 1107 has a diameter between about 1 foot and 100 feet, or 5 feet and 50 feet, or 10 feet and 20 feet. In an example, the OCM reactor 1107 has a diameter that is about 12 feet.

The OCM reactor 1107 can include a liner 1108 that can be formed of a refractory material. Examples of refractory materials include the oxides of aluminum (e.g., alumina), silicon (e.g., silica), zirconium (e.g., zirconia) and magnesium (e.g., magnesia), calcium (e.g., lime) and combinations thereof. Other examples of refractory materials include binary compounds, such as tungsten carbide, boron nitride, silicon carbide or hafnium carbide, and ternary compounds, such as tantalum hafnium carbide. Refractory material can be coated and/or doped with rare earth elements or oxides, or other basic alkaline earth and/or alkali metals. This may aid in preventing coking. OCM catalyst nanowires may also be used to coat refractory material to prevent coking. The liner 1108 can have a thickness from about 0.5 inches and 24 inches, or 1 inch and 12 inches, or 3 inches and 9 inches. In an example, the liner 1108 has a thickness of about 6 inches.

The inlets 1104 and 1105 can have various shapes and sizes. The inlet 1105 can have cross-section that is circular, oval, triangular, square, rectangular, pentagonal, hexagonal or any partial shape and/or combination thereof. In some examples, the inlet 1104 has a diameter between about 10 inches and 100 inches, or 20 inches and 80 inches, or 40 inches and 60 inches. In an example, the inlet 1104 has a diameter that is about 56 inches. In some examples, the inlet 1105 has a diameter between about 1 inch and 50 inches, or 10 inches and 30 inches, or 15 inches and 20 inches. In an example, the inlet 1105 has a diameter that is about 18 inches.

Each of the ribs 1103 can be an airfoil mixer that is configured to bring the second fluid stream in contact with the first fluid stream. This can provide for uniform mixing. Each of the ribs 1103 can include one or more openings that are in fluid communication with a fluid flow path leading from the inlet 1104 to the OCM reactor 1107. In some examples, each of the ribs 1103 has an opening on a top or bottom portion of a rib (with respect to the plane of the figure) and/or on opposing side portions—i.e., along a direction that is orthogonal to the direction of fluid flow from the inlet 1104 to the OCM reactor 1107. By introducing the second fluid stream to the first fluid stream prior to the OCM reactor 1107, the ribs can enable mixing of the first and second fluid streams prior to an OCM reaction in the OCM reactor 1107.

In some cases, the point along a given rib 1103 at which the second fluid stream is introduced to the first fluid stream, as well as the fluid properties of the respective streams (e.g., pressure, flow rate and/or temperature), is selected such that the auto-ignition (e.g., automatic combustion or partial combustion of methane) prior to the OCM reactor 1107 can be minimized, if not eliminated. This can help ensure that reaction between a hydrocarbon (e.g., methane) and an oxidizing agent (e.g., oxygen) occurs in the OCM reactor 1107 to yield $C_{2+}$ compounds, and helps reduce (e.g., by at least 50%, 60%, 70%, 805%, 90%, or more), if not eliminate, unwanted reactions, such as the partial or complete combustion of the hydrocarbon. In some examples, the second stream is introduced to the first stream at the top of each of the ribs 1103.

Figure 12:
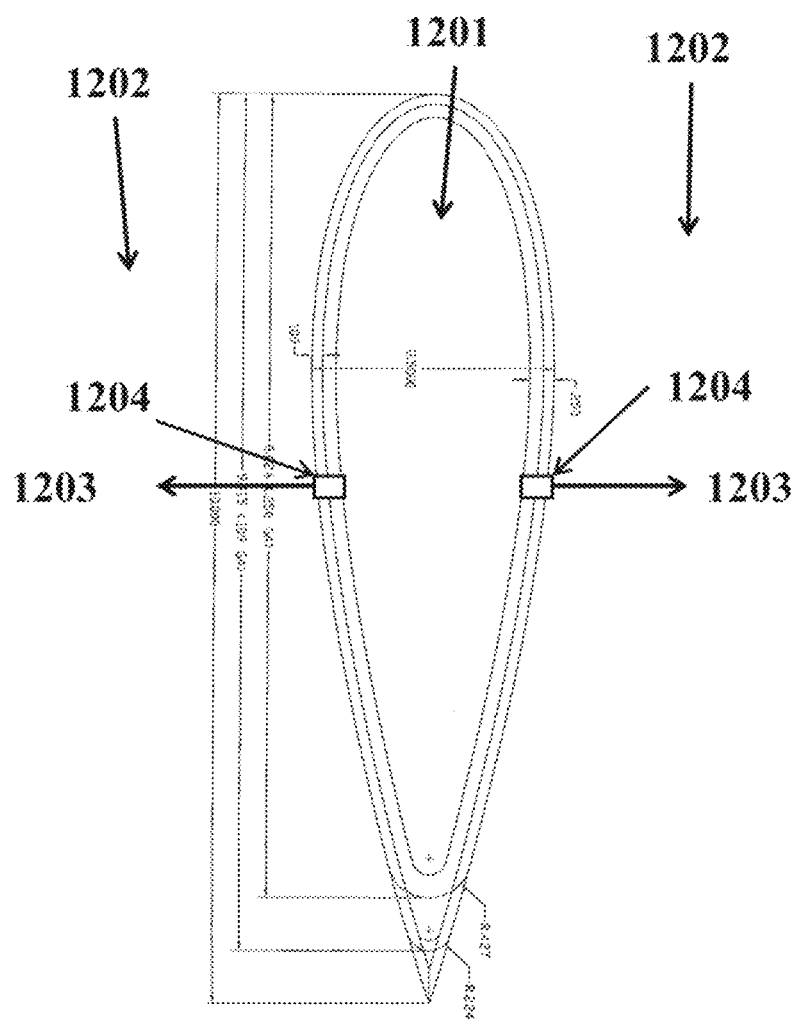
FIG. 12 schematically illustrates an example blade that may be employed for use as a rib of a mixer.

A rib can be a blade that is in the shape of an airfoil. FIG. 12 shows an example blade 1201 that may be employed for use as a rib. In some examples, the blade can have a width (the widest portion, 'W') from about 0.5 inches to 10 inches, and a length from about 0.5 ft. to 10 ft. The blade 1201 can be part of a mixer upstream of an OCM reactor. The mixer can be integrated with the OCM reactor. The mixer and OCM reactor can be integrated with a heat exchanger (see below). During operation of an OCM system having the blade 1201, a first fluid stream may be directed along a fluid flow path 1202. The first fluid stream can include a hydrocarbon, such as methane. A second fluid stream 1203 may be directed out of the blade 1201 through openings 1204 on opposing sides of the surfaces of the blade 1201. The openings 1204 can be holes or slits, for example. The second fluid stream 1203 can include an oxidizing agent, such as oxygen ($O_2$). In some cases, the second fluid stream 1203 includes air. The second fluid stream can include a mixture of oxygen and methane.

The openings 1204 can be on the sides of the blade 1201. As an alternative or in addition to, the openings 1204 can be on a top and/or bottom portion of the blade (with respect to the plane of the figure). The blade 1201 can have at least about 1, 2, 3, 4, 5, 6, 7, 8, 9, 10, 20, 30, 40, 50, or 100 openings, which can have various sizes and configurations. For example, the openings 1204 can be holes or slits. The openings can be disposed side-by-side along the length of the blade 1201 (i.e., along an axis orthogonal to the width of the blade ('W') and in the plane of the figure), or side by side along a thickness of the blade 1201 (i.e., along an axis orthogonal to the width of the blade and orthogonal to the plane of the figure).

The mixer can provide rapid and complete mixing of two or more gas streams. Additionally, the airfoil shape can help minimize, if not eliminate, stagnant or re-circulation zones in a mixing zone downstream of the mixer. This may allow for every portion of the mixed stream to spend the same amount of time within the mixing zone, thus leading to a very narrow and controlled distribution of the residence times in the mixing zone itself.

Pre-Heating Devices, Systems and Methods

Another aspect of the present disclosures provides heating devices, systems and methods. Such devices, systems and methods may be employed for use in pre-heating reactant streams prior to an OCM reaction. Pre-heating devices, systems and methods of the present disclosure can be used separately or in conjunction with other pre-conditioning approaches of the present disclosure, such as mixing. For example, a pre-heater can be integrated with a mixer. As another example, a pre-heater can be separate from a mixer and situated upstream or downstream of the mixer but situated prior to an OCM reactor.

In some cases, streams comprising an oxidizing agent (e.g., $O_2$, which may be provided by way of air) and/or methane are heated by reaction heat prior to being mixed. This can advantageously reduce the amount of reaction heat that is lost as waste heat, which can decrease the amount of energy that is used in external heat exchangers to pre-heat the streams.

For example, an air stream or methane stream can be heated by heat from an OCM reactor. As another example, a mixed stream comprising air and methane may be heated by heat from an OCM reactor. The air and/or methane stream can be directed along a location that is in thermal communication with a catalyst bed to provide heat to the air and/or methane stream prior to mixing or an OCM reaction to generate $C_{2+}$ compounds. In some examples, the air and/or methane stream are directed to a heat exchanger that is integrated with the OCM reactor, where at least a portion of the heat from the OCM reaction is transferred to the air and/or methane stream.

In some cases, a system for performing an OCM reaction to generate $C_{2+}$ compounds comprises an OCM reactor comprising an OCM catalyst that facilitates the OCM reaction to generate the $C_{2+}$ compounds, and an injector comprising a fluid flow conduit that directs a first gas stream through at least a portion of the OCM reactor to one or more openings that are in fluid communication with the OCM reactor. The fluid flow conduit may be in thermal and/or fluidic communication with the OCM reactor, and the first gas stream comprises one of methane and an oxidizing agent. In some examples, the oxidizing agent includes oxygen ($O_2$). The system may further comprise a gas distribution manifold comprising one or more openings that are in fluid communication with the one or more openings of the injector and the OCM reactor. The gas distribution manifold may direct a second gas stream into the OCM reactor. The second gas stream may comprise the methane and/or the oxidizing agent.

An OCM reactor can be integrated with a heat exchanger, which can enable reactant streams to be preheated by heat liberated from a reactor to optimize a downstream reaction, such as an OCM reaction. For example, a stream comprising an oxidizing agent (e.g., $O_2$), such as an air stream, can be heated with a stream comprising a hydrocarbon stream (e.g., methane) prior to mixing. The mixed stream can then be directed to the OCM reactor, as described above or elsewhere herein.

A mixture of methane and oxygen can be reactive above a given temperature. The auto-ignition temperature of methane in air is about 580° C. at atmospheric pressure. Under such conditions, bringing methane in contact with oxygen at such elevated temperature may lead to premature reaction, such as partial or complete combustion, leading to potentially undesirable products, such as CO and $CO_2$. However, in some cases, it may not be desirable to decrease the temperature of a methane and/or $O_2$ stream (e.g., below the auto-ignition temperature) as this may decrease the overall conversion in an OCM process.

The present disclosure provides various approaches for reducing the auto-ignition of methane. In some cases, the time that methane is in contact with $O_2$ is reduced while the temperature of the methane and/or $O_2$ streams is maintained at a requisite level to effect a given degree of conversion. The light off temperature for an OCM reaction can be a function of linear flow rate through the OCM reactor (e.g., catalyst bed). Similarly, minimal inlet temperature under operating conditions may be affected by the linear flow rate though the OCM reactor.

In some cases, an inlet section is used to process a fraction of the inlet gas feed (e.g., less than 33%) at reduced local flow rate and inject the reaction product in a second section of the OCM reactor where unreacted bypass feed will contact a hotter reacted product stream (e.g., stream containing $C_{2+}$ compounds), such as in a counter flow fashion. The hotter product stream can be used to promote the OCM reaction by increasing the OCM reactor temperature relative to the reactor feed inlet. In some examples, an artificially created bypass channel is provided through at least a portion of an OCM reactor, which can decrease the feed linear flow rate in the front end of the OCM reactor compared to the feed linear flow rate in the back of the OCM reactor.

OCM systems of the disclosure can be integrated with heat exchangers, which can enable heat liberated in an OCM reaction to be used to heat (or preheat) methane and/or an oxidizing agent (e.g., O, which may be provided by air) prior to an OCM reaction.

Integrated heat exchangers of the disclosure may enable the creation and maintenance of a hot spot within an OCM catalyst, allowing an OCM reactor to be operated with a reduced temperature inlet compared to cases in which an integrated heat exchanger is not used. In some implementations, the inlet gas is heated to the necessary temperature by a heat exchanger, which enables the OCM reaction in a fixed bed reactor. This temperature can be between 300° C.-550° C. This approach may be sensitive to the oxygen concentration in the feed and require substantially short residence times from the heater to the catalyst bed to prevent combustion, such as via auto-ignition. The heat exchanger capital cost may also be an issue. For example, the inlet temperature can be about 350° C. for a fluidized bed reactor (in some cases with relatively high reverse flow direction heat transfer), which can enable increased conversion in an adiabatic bed as well as minimizing the risk of premature ignition, especially when using pure $O_2$ as the oxidizing agent in the OCM reaction.

In some cases, a heating element is lined externally with an OCM catalyst (e.g., coated or a sleeve is placed over heater surface). The heating element can have a relatively low heat transfer efficiency so as to maintain a high skin (or boundary layer) temperature of the OCM catalyst that externally coats the heating element. As the inlet gas passes adjacent to the heating element, gas near the surface of the catalyst can be heated to a temperature that is at or near the skin temperature, which can initiate the OCM reaction and release heat that can mix with the bulk gas, uniformly heating the process gas stream. The skin temperature of the OCM-catalyst lined heating element can be sufficiently high so as to help ensure that the OCM reaction is highly selective (e.g., from about 750° C. to about 900° C.) for a desirable product (e.g., $C_{2+}$ compounds). In some cases, as the OCM reaction proceeds on the heating element surfaces, it produces heat that increases the inlet gas temperature as well as produces desirable OCM reaction products (e.g., $C_{2+}$ compounds, water). This can be an approach to both reduce inlet heat exchanger capital costs as well as enable much higher single stage conversions, because the inlet $O_2$ (or other oxidizing agent) concentration can be sufficiently high to heat the inlet gas from low temperatures (e.g., 25° C.-300° C.) to the desired reactor inlet temperature (e.g., 400° C.-600° C.). For example, about 10% conversion of methane at a $C_2$ selectivity approaching 60% may heat the inlet gas from 200° C. to 500° C. An additional 10% conversion can be attained in the fixed bed portion of the reactor, for example, resulting in a much higher single stage conversion. Heat exchangers lined with OCM catalysts of the present disclosure can take advantage of the substantially rapid OCM reaction kinetics at temperatures in excess of 750° C., which may only require a limited number of catalyst coated heating elements to heat the inlet gas, while still maintaining a substantially short residence times to prevent combustion prior to the catalyst bed. The limited number of tubes and poor heat transfer to the gas stream may keep the heating duty of the inlet gas heat exchanger low, and the exit gas from the reactor can potentially be used as the heating medium. In such a case, at least an additional heater may be required to initiate the reaction.

Integrated heat exchangers of the present disclosure can be used to transfer heat to a gas stream undergoing a homogeneous endothermic reaction, such as alkane cracking into alkenes. For example, an OCM reactor may include a cracking unit downstream of a catalyst unit comprising an OCM catalyst. The cracking unit can be heated using heat generated in the catalyst unit in an OCM reaction.

Reactors of the present disclosure can be operated or designed to operate with reduced linear velocity. Reduced linear velocity operation can promote feed pre-heating. Reduced linear velocity operation can reduce axial convective heat transfer. Reduced linear velocity operation can move the peak bed temperature location toward the front end of the bed. Reaction heat can be used for stream preheating. Reduced linear velocity operation can result in reduced oxygen consumption in low selectivity regions. Reduced linear velocity operation can increase reaction selectivity across the reactor. A reactor can operate with reduced linear velocity in part of or in the entire reactor. For example, a reactor can comprise a low linear velocity region followed by a high linear velocity region. Linear velocity can be controlled between reactor regions by changing the reactor diameter or width. A reactor can comprise an annular reactor, wherein a feed stream enters the central region and flows from the central region to the outer region.

The linear velocity can be any suitably low value, such as less than or equal to about 3 meters per second (m/s), about 2.5 m/s, about 2 m/s, about 1.5 m/s, about 1 m/s, about 0.5 m/s, about 0.4 m/s, about 0.3 m/s, about 0.2 m/s, about 0.1 m/s, about 0.05 m/s, about 0.01 m/s or less.

The present disclosure provides for tubular reactor systems. A tubular reactor can comprise a single stage. A tubular reactor can employ a heat removal medium, such as molten salt. A heat removal medium can be used for heat removal from a reactor bed. A heat removal medium can be used for preheating feed streams. Tubular reactor systems can be used for reactions including but not limited to oxidative coupling of methane (OCM) and oxidative dehydrogenation of ethane (ODH). Temperature control in a tubular reactor bed can be controlled by designing different bed properties in segments. Such bed segmentation to the temperature profile can be achieved by controlling the linear velocity of the reaction gas, for example by varying the tube diameter or by including non-reactive sleeves or inserts. Bed segmentation to control the temperature profile can be achieved by controlling the thermal conductivity of the bed, for example by controlling the catalyst form (e.g., shape, size, extrudates, rings, monoliths, foams) or by choice of catalyst support (e.g., alumina, SiC, silica, magnesia). Bed segmentation to control the temperature profile can be achieved by changing the thermal conductivity of the tube wall liner. Bed segmentation to control the temperature profile can be achieved by using multiple heat removal medium sections with varying levels of turbulence or temperatures.

In some cases, incomplete mixing of the methane source and the oxygen source can result in reduced performance of the OCM catalyst (e.g., due to the formation of hot spots where oxygen concentration is relatively higher). In some cases, additional degrees of freedom with regard to methane and oxygen mixing (e.g., temperature differences, spatial differences or frequency differences) can be manipulated to improve the performance of the OCM reaction.

For example, the temperature of the methane source and the oxygen source can be altered or adjusted independently to compensate for hot spot formation due to incomplete mixing. Having the inlet oxygen source (e.g., air) cooler than the methane source (e.g., natural gas), can create a self-correcting system where the mixture temperature is relatively lower for portions of the mixture that are relatively higher in oxygen concentration. The somewhat lower inlet temperature can at least partially compensate for the increased change in temperature (e.g., due to the relatively higher oxygen concentration resulting in additional heat released in the OCM reaction).

Another effect of the relatively lower inlet mixture temperature for portions of the mixture that are relatively higher in oxygen concentration is that the ignition of OCM is somewhat delayed, resulting in more radial mixing prior to initiation of the OCM reaction. Both effects can have the desired outcome of reducing the occurrence of, and temperature of hot spots. Hot spots can create increased flow resistance through porous media, shifting the flow profile within a catalyst bed.

In an aspect, the present disclosure provides a method for performing an oxidative coupling of methane (OCM) reaction. The method can comprise heating a first stream comprising methane ($CH_4$) to a first temperature, heating a second stream comprising oxygen ($O_2$) to a second temperature, and mixing the first stream and the second stream to produce a third stream. The second temperature may be lower than the first temperature. The third stream can be contacted with an OCM catalyst to perform an OCM reaction. In some cases, the first stream is natural gas and the second stream is air.

In some instances, the first stream and second stream are mixed prior to performing the OCM reaction. In some cases, the first stream and second stream are imperfectly. Portions of the third stream that have a relatively higher concentration of $O_2$ can have a lower initial temperature due to e.g., the second temperature is lower than the third temperature, and/or a maximum temperature created in the OCM reaction is reduced relative to perfect mixing and/or the second temperature being approximately equal to the third temperature. In some cases, the light-off temperature is reduced relative to perfect mixing and/or the second temperature being approximately equal to the third temperature.

In some cases, a difference between the first temperature and the second temperature is greater than or equal to about 20° C., 40° C., 60° C., 80° C., 100° C., 120° C., 140° C., 160° C., 180° C., 200° C., 240° C., 260° C., 280° C., 300° C., 350° C., 400° C., or more. In some cases, the difference is between any of the two values described herein, for example, from about 25° C. to about 200° C.

The desire to keep the methane source below a certain temperature to limit coking can limit the practical temperature difference between the input streams. Coking can be substantially reduced when the temperature of natural gas is kept below about 550° C. for wet gas (e.g., comprising at least about 1% $C_{2+}$ compounds) and below about 600° C. for dry gas (e.g., comprising at most about 1% $C_{2+}$ compounds).

While avoiding coking can provide a practical upper limit for the methane source temperature, the desired temperature of the mixture can provide a practical lower limit for the temperature of the oxygen source. Also, the relative heat capacities of the methane source and the oxygen source can put constraints on the temperature difference that can be achieved. Methane has about a 10-fold greater molecular heat capacity than oxygen. The heat capacity of nitrogen is higher than oxygen, so in some cases, the use of air as the oxygen source can allow for a higher relative temperature difference between the oxygen source and the methane source, as compared to the situations where pure or enriched $O_2$ is used. In some cases, the heat capacity of the second stream is greater than or equal to about 30%, 40%, 50%, 60%, 70%, or more of the heat capacity of the third stream.

Table 2 shows three example scenarios for differential temperature mixing. The feed temperatures are shown in the upper portion of the table. The temperatures of the mixtures (i.e., inlet temperatures absent the heat of reaction) are shown in the middle portion of the table for perfect mixing and scenarios where a portion of the mixture is imperfectly mixed and contains relatively more or less air. The bottom third of the table shows the inlet temperature difference that is achieved in the various scenarios (e.g., that can off-set any hot spot formation in the subsequent OCM reaction).

TABLE 2

Examples of Temperature Differences

|  | Scenario #1 | Scenario #2 | Scenario #3 |
|---|---|---|---|
| Feed Stream Temperatures (° C.) | | | |
| $CH_4$ (50 kmol) | 520 | 550 | 550 |
| $N_2$ (17 kmol, i.e., component of Air) | 520 | 380 | 260 |
| $O_2$ (4.5 kmol, component of Air) | 520 | 380 | 260 |
| Final Mixture Temperatures (° C.) | | | |
| Perfect Mixing | 520 | 520.6 | 500.0 |
| +10% Air | 520 | 518.0 | 496.0 |
| −10% Air | 520 | 523.1 | 504.0 |
| +20% Air | 520 | 515.6 | 492.0 |
| −20% Air | 520 | 525.7 | 508.8 |
| Temperature Range (° C.) | | | |
| @ +/−10% Air | 0 | 5.1 | 8.0 |
| @ +/−20% Air | 0 | 10.1 | 16.8 |

In some cases, the methods described herein shift the position of the hot spot in the OCM reactor (e.g., shift it axially further from the inlet). In some cases, the methods described herein create "virtual bypass channels" where oxygen remains unreacted when initially contacted with the OCM catalyst, to be available for reaction at a later portion of the OCM catalyst bed. Benefits of bypass channels are further explained in U.S. Patent Publication No. 2015/0152025, which is incorporated herein by reference in its entirety. The virtual bypass channel can achieve the same or a similar function to the physical bypass, allowing some parts of the catalyst bed to be used as catalytic heating elements to condition a portion of the feed gas. This can result in the ability to operate the reactor at a lower overall inlet temperature, enabling greater per pass conversion through the catalyst bed and increasing yields of desirable products. This can also stabilize the performance of the reactor and enable greater process fluctuation and turn down.

Figure 13A:
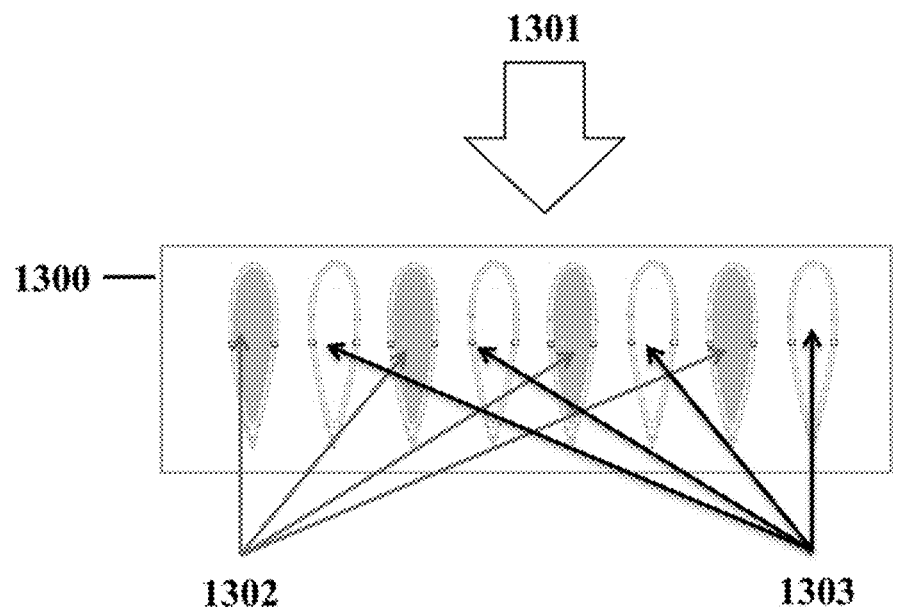
FIG. 13A shows a schematic of an example reactor with multiple oxygen feeds injected at different points along a direction perpendicular to flow.
Figure 13B:
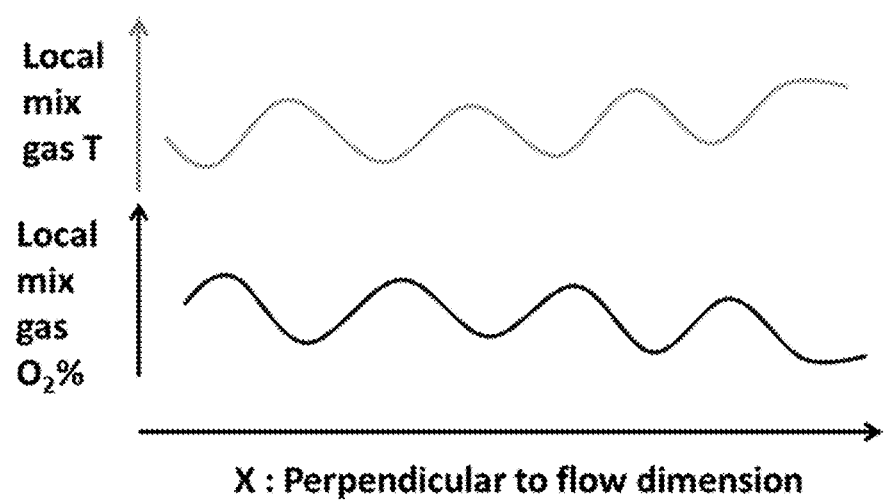
FIG. 13B shows graphs of local mix gas temperature and local mix gas percent oxygen in a reactor with multiple oxygen feeds injected at different points along a direction perpendicular to flow.
Figure 14A:
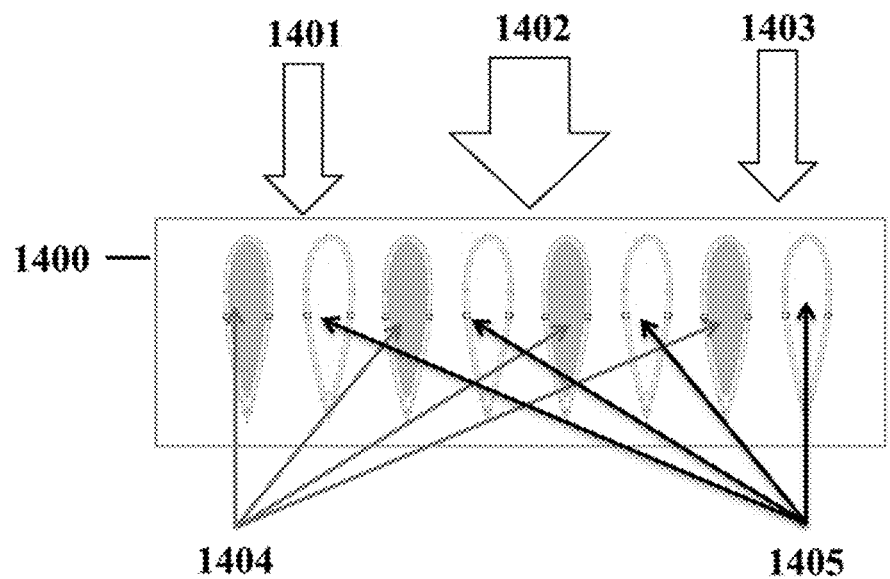
FIG. 14A shows a schematic of an example reactor with multiple methane feeds and multiple oxygen feeds injected at different points along a direction perpendicular to flow.
Figure 14B:
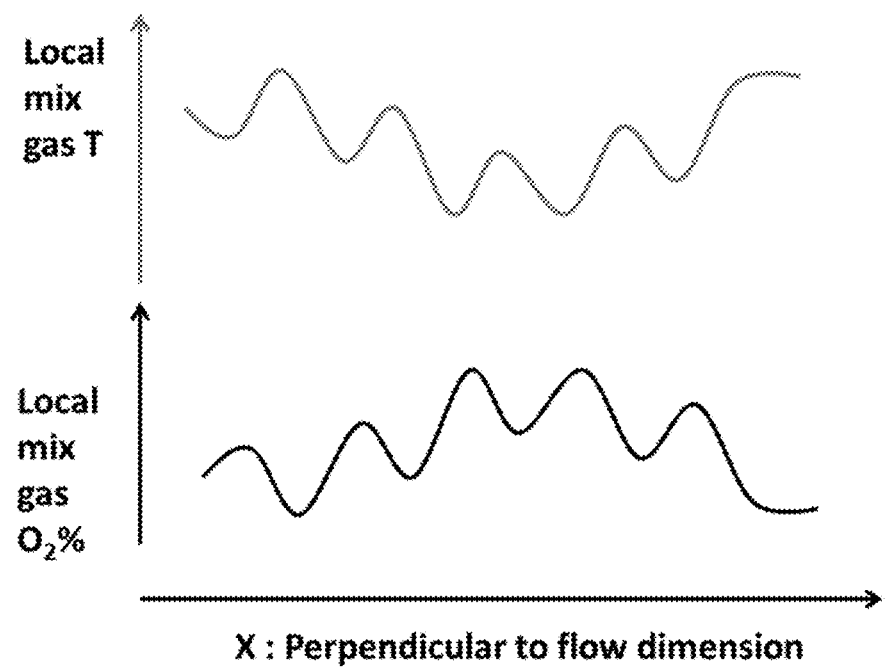
FIG. 14B shows graphs of local mix gas temperature and local mix gas percent oxygen in a reactor with multiple methane feeds and multiple oxygen feeds injected at different points along a direction perpendicular to flow.

The present disclosure also provides systems and methods for injecting methane and/or oxygen, or various concentrations or temperatures thereof into different portions of the cross-section of an OCM reactor. For example, the mixing manifold for the $O_2$ source gas can be split in two or more manifolds fed by different $O_2$ feed source gas streams at different temperatures with different flows. This can result in different local $CH_4$ to $O_2$ ratios at the mixer exits, as well as different local temperatures depending on the spatial distribution of the feed injectors and separately pre-heated $O_2$ feed stream. If the $O_2$ source itself contains $CH_4$, the ratio of $CH_4$ and $O_2$ in each $O_2$ feed manifold can be adjusted to provide additional control of the $CH_4/O_2$ ratio spatial distribution exiting the mixer. For example, FIG. 13A shows a reactor 1300, with a $CH_4$ feed 1301, and with $O_2$ feeds 1302 and 1303 injected at different points along a direction perpendicular to flow. FIG. 13B shows graphs of the resulting variance in the local mix gas temperature (upper, gray) and the local mix gas percent oxygen (lower, black) in the x-dimension perpendicular to the flow dimension. The methane feed can also be split more coarsely and feed at different temperatures in different areas of the inlet of the $O_2$ feed distributor assembly. For example, FIG. 14A shows a reactor 1400 methane feeds 1401, 1402, and 1403 in addition to oxygen feeds 1404 and 1405. FIG. 14B shows graphs of the resulting variance in the local mix gas temperature (upper, gray) and the local mix gas percent oxygen (lower, black) in the x-dimension perpendicular to the flow dimension. As the methane feed carries most of the heat capacity of the gas entering the reactor, heating a portion of the methane to a much higher temperature than the remainder of the methane feed can enable even larger swings in inlet temperature distribution. Some of the gas may enter the catalyst bed far below the light off temperature of the catalyst, provided that radial heat propagation is sufficient to progressively warm up the gas stream to a temperature above catalyst light off temperature.

Also provided herein is a method for performing an oxidative coupling of methane (OCM) reaction. The method can comprise heating a first stream comprising oxygen ($O_2$) to a first temperature; dividing a second stream comprising methane ($CH_4$) into at least two portions and heating each of the portions to a different temperature; injecting each of the portions of the second stream into a different area of a mixer, which mixer mixes the portions of $CH_4$ with the first stream; and contacting the mixtures produced in (c) with an OCM catalyst to perform an OCM reaction. In some cases, the first stream is air and the second stream is natural gas.

In another aspect, provided herein is a method for performing an oxidative coupling of methane (OCM) reaction. The method can comprise heating a first stream comprising methane ($CH_4$) to a first temperature; dividing a second stream comprising oxygen ($O_2$) into at least two portions and heating each of the portions to a different temperature; injecting each of the portions of the second stream into a different area of a mixer, which mixer mixes the portions of $O_2$ with the first stream; and contacting the mixtures produced in (c) with an OCM catalyst to perform an OCM reaction. In some cases, the first stream is natural gas and the second stream is air.

In some cases, the areas of the mixer into which each of the portions of the second stream comprising $CH_4$ and/or $O_2$ are injected are chosen to reduce a maximum temperature created in the OCM reaction (i.e., hot spot). In some cases, the areas of the mixer into which each of the portions of the second stream comprising $CH_4$ and/or $O_2$ are injected are chosen to bypass a portion of the $O_2$ further into the OCM catalyst. In an example, some of the gas enters a section of the catalyst bed far below the light off temperature of the catalyst. The radial heat propagation in the bed, as well as propagation of the catalyst activation within the catalyst bed, progressively warm up and reduce the volume of this gas stream as it travels through the catalyst bed, until the last fraction of this gas reaches a temperature above the catalyst light off temperature. At this point, the $O_2$ contained in this stream will be completely consumed by the OCM reaction. If cold gas in injected along a line in a plane with the catalyst entry face at the inlet of the reactor, the ignition front can be characterized by a wedge shape.

Figure 15:
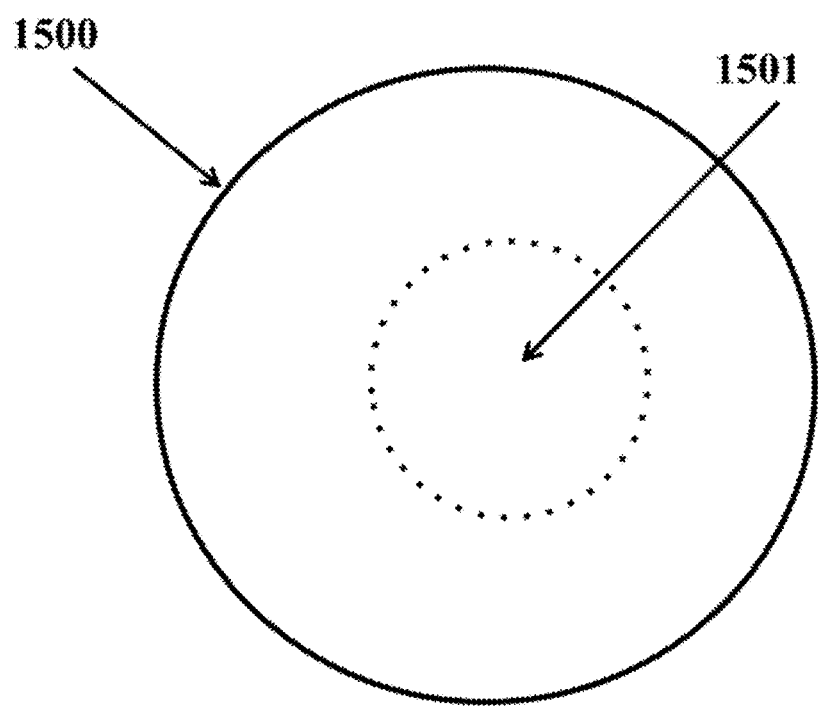
FIG. 15 shows an cross section of an example mixer inlet employing spatially differentiated mixing.

FIG. 15 shows an example of spatially differentiated mixing as described herein. A top-view of the circumference 1500 into which methane is injected in the mixer of FIG. 11A is shown (e.g., equivalent of 1104). Within the circumference 1500, there can be one or more areas 1501 that are differentiated with respect to composition and/or inlet temperature.

The present disclosure also provides methods for mixing the oxygen source and the methane source at different frequencies (i.e., alternately and repeatedly injecting the methane and oxygen into the OCM reactor or mixer). The alternative mixing can also be varied spatially over the area of the OCM reactor and have variation of temperature of the input streams, as described herein. In some cases, for a given average condition set (e.g., composition, pressure and temperature) of the inlet oxygen and methane, local or time variations in conditions can be used to manipulate the formation of hot spots and/or their maximum temperature in order to improve OCM performance. In the case of temporal oscillation of feed composition and/or feed temperature, the heat capacity of the catalyst particles can enable the transfer of energy between the different streams. Such a transfer can potentially be more effective than long range heat propagation. This is similar in concept to using fluid bed or flow reversal techniques with a decoupling of solid temperature where the gas temperature is never at a local thermal steady state.

In another aspect, the present disclosure provides a method for performing an oxidative coupling of methane (OCM) reaction. The method can comprise (a) providing a first stream comprising methane ($CH_4$) at a first temperature; (b) providing a second stream comprising oxygen ($O_2$) at a second temperature; and (c) alternately (and in some cases sequentially) injecting the first stream and the second stream into an OCM reactor which comprises an OCM catalyst to perform an OCM reaction. In some cases, the second temperature is less than the first temperature.

The first stream and the second stream can be alternated at a frequency. The frequency can be greater than or equal to about 0.01 Hertz (Hz), about 0.05 Hz, about 0.1 Hz, about 0.5 Hz, about 1 Hz, about 5 Hz, about 10 Hz, about 50 Hz, about 100 Hz, about 500 Hz, or more. In some cases, the frequency is between about 0.1 and about 10 Hz. The frequency can also be selected based on the relative heat capacity of the gas and the solids to set a lower limit on the modulation frequency. An upper limit on the modulation can be set based on a multiple of mixer residence time; for example, for a mixer residence time of 100 milliseconds (ms), pulses at a frequency of 10 Hz may not be very sharp by the time they reach the catalyst face.

In some cases, the frequency is varied in response to a temperature measured in the OCM reactor (e.g., where relatively less $O_2$ is injected into the OCM reactor when the temperature in the OCM reactor approaches a maximum temperature).

The alternating injection can be performed with piezo-electric injectors (e.g., using an array of piezo-electric injectors distributed over a cross section of the reactor), such as those used to inject liquid fuels in gasoline or diesel engines. Piezo-electric injectors can enable very precise control of the time profile of the injection as well as of the amount of the injection. For example, using pulse trains of a few milliseconds, gas injections can be controlled to control oscillations in the composition of the mixed gas stream over a wide frequency range. Piezo-electric injectors may be engineered with increased flow capacities for low density streams to enable gas injection.

Methods for Improving Olefin Yield

An aspect of the present disclosure provides OCM systems and methods for increase the concentration of alkenes (or olefins) in $C_{2+}$ compounds outputted from an OCM reactor. This can advantageously provide $C_{2+}$ product stream that may be better suited for downstream uses, such as the commercial production of polymeric materials, as well as greater carbon efficiency of the overall process. In some embodiments, an OCM system provides improved alkene yield by alkane cracking in a catalyst unit or cracking unit. Such in situ cracking of alkanes can provide a product stream with hydrocarbon distributions tailored for various end uses.

Figure 16:
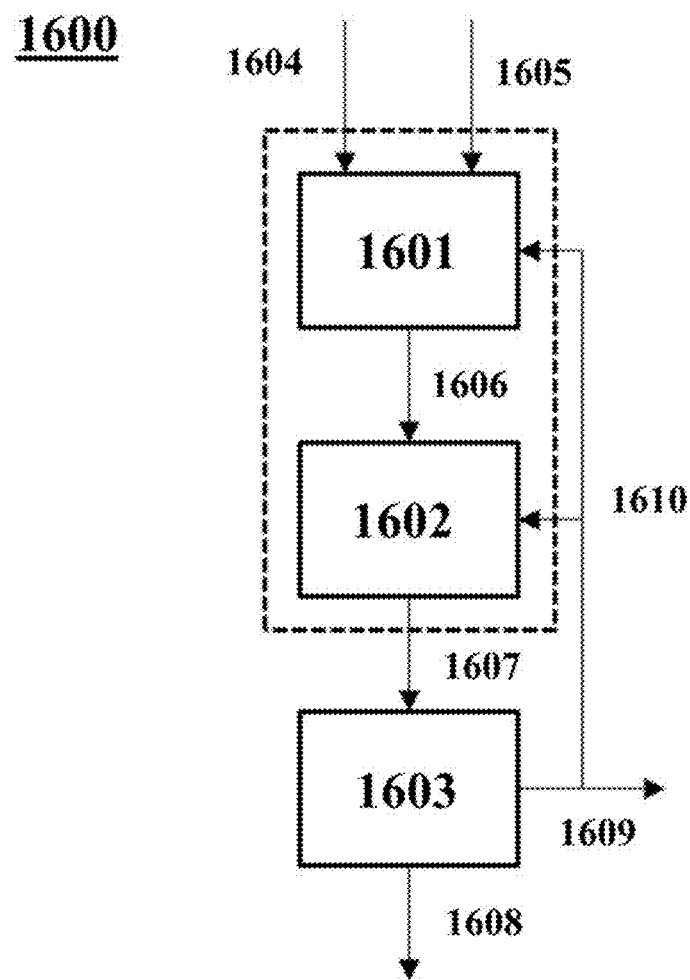
FIG. 16 schematically illustrates an example system for the oxidative coupling of methane (OCM)

FIG. 16 shows an example OCM system 1600 comprising an OCM reactor 1601, a cracking unit 1602 downstream of the OCM reactor 1601, and at least one separation unit 1603 downstream of the cracking unit 1602. The OCM reactor 1601 and cracking unit 1602 can be separate units or integrated as a single unit, as illustrated by the dashed box. The arrows indicate the direction of fluid flow from one unit to another. During use, a first fluid stream ("stream") 1604 comprising methane ($CH_4$) and a second fluid stream 1605 comprising an oxidizing agent (e.g., $O_2$) can be directed into the OCM reactor 1601, where they may react in the presence of a catalyst provided within reactor 1602 to form $C_{2+}$ compounds, which are included in a third stream 1606. The third stream 1606 can include other species, such as non-$C_{2+}$ impurities like Ar, $H_2$, CO, $CO_2$, $H_2O$, $N_2$, $NO_2$ and $CH_4$. The third stream 1606 may comprise OCM products, which can include $C_{2+}$ compounds and non-$C_{2+}$ impurities.

Next, the third stream 1606 may be directed to the cracking unit 1602. In the cracking unit 1602, alkanes in the $C_{2+}$ compounds can react to form $C_{2+}$ compounds with unsaturated moieties, which are outputted from the cracking unit 1602 in a forth stream 1607, such as carbon-carbon double bonds (e.g., ethylene and propylene). The fourth stream 1607 can then be directed to other unit operations for processing gases in the fourth stream 1607, such as the separation unit 1603 used for separation of at least some, all, or substantially all of the $C_{2+}$ compounds from other components in the fourth stream 1607 to yield a fifth stream 1608 and a sixth stream 1609. The streams 1608 and 1609 can each be directed to one or more storage units. The fifth stream 1608 can be directed to $C_{2+}$ storage or a non-OCM process.

Methane in the first fluid stream 1604 can be provided from any of a variety of methane sources, including, e.g., a natural gas source (e.g., natural gas reservoir) or other petrochemical source, or in some cases recycled from product streams. Methane in the first fluid stream may be provided from an upstream non-OCM process.

The fifth stream 1608 can include $C_{2+}$ (e.g., olefins) compounds at a concentration (e.g., mole % or volume %) that is at least about 10%, 20%, 30%, 40%, 50%, 60%, 70%, 80%, 90%, 95%, 99%, or more. The sixth stream 1609 can include $C_{2+}$ compounds at a concentration that is less than or equal to about 99%, 95%, 90%, 80%, 70%, 60%, 50%, 40%, 30%, 20%, 10%, or less. The sixth stream 1609 can include methane at a concentration of greater than or equal to about 10%, 20%, 30%, 40%, 50%, 60%, 70%, 80%, 90%, 95%, 99%, or more. The concentration of $C_{2+}$ compounds in the fifth stream 1608 can be higher than the concentration of $C_{2+}$ compounds in the sixth stream 1609. The sixth stream 1609 can include other species, such as Ar, $H_2$, CO, $CO_2$, $H_2O$, $N_2$, $NO_2$ and $CH_4$. At least some, all or substantially all of $CH_4$ in the sixth stream 1609 may optionally be recycled to the OCM reactor 1601 and/or the cracking unit 1602 in a seventh stream 1610. $C_2$ splitting can also be employed for ethane recycle to the OCM reactor and/or the cracking unit.

The at least one separation unit 1603 can include a plurality of separation units, such as at least about 2, 3, 4, 5, 6, 7, 8, 9, 10, 20, 30, 40, or 50 separation units, at least some of which can be in series and/or parallel. In some examples, the at least one separation unit 1603 is a full separation train, in some cases including one or more distillation columns, scrubbers, etc. The at least one separation unit 1603 can include an olefin/alkane splitter and/or $CO_2$ separation unit. The seventh stream 1610 can include C1 (methane) recycle to the OCM reactor 1601 and/or the cracking unit 1602.

In some examples, at least about 1%, 2%, 3%, 4%, 5%, 10%, 20%, 30%, 40%, 50%, 60%, 70%, 80%, 90%, or more of the non-$C_{2+}$ components (e.g., $CH_4$ and/or $N_2$) of the fourth stream 1607 can be separated by the separation unit 1603 and directed along the sixth stream 1609. This can provide a fifth stream 1608 that has a higher concentration of $C_{2+}$ compounds, including olefins and higher molecular weight alkanes.

The system 1600 can include any number of OCM reactors 1601 and cracking units 1602. The system 1600 can include at least about 1, 2, 3, 4, 5, 6, 7, 8, 9, 10, or more OCM reactors 1601. The OCM reactors 1601 can be the same, similar or dissimilar reactors or reactor types arranged in series or parallel processing trains. The OCM reactors 1601 can be in series and/or in parallel. The system 1600 can include at least about 1, 2, 3, 4, 5, 6, 7, 8, 9, 10, or more cracking units 1602. The cracking units 1602 can be the same, similar or dissimilar reactors or reactor types arranged in series or parallel processing trains. The cracking units 1602 can be in series and/or in parallel. Alternatively, the reactor 1601 can be used as a cracking unit by periodically changing the feed of the reactor between OCM feed to a $C_{2+}$ alkane rich feed. In such a case, the heat capacity of a catalyst bed in the reactor 1601 can be used for alkane cracking.

The system 1600 can include at least about 1, 2, 3, 4, 5, 6, 7, 8, 9, 10, or more separation units. In the illustrated example, the system 1600 includes one separation unit 1603. The separation unit 1603 can be, for example, a distillation column, scrubber, or absorber. If the system 1600 includes multiple separation units 1603, the separation units 1603 can be in series and/or in parallel.

Although described for illustration of certain aspects as gas streams passing into, through and out of the reactor systems in FIG. 16, it will be appreciated that the streams 1604, 1605, 1606, 1607, 1608, 1609 and 1610 can be gaseous streams, liquid streams, or a combination of gaseous and liquid streams. In some examples, the streams 1604 and 1605 are gaseous streams, and the stream 1608 and 1609 are liquid streams.

In some examples, the separation unit 1603 can include more than two product streams. For example, olefins can be directed out of the separation unit 1603 along an olefin stream and ethane and propane can be directed out of the separation unit 1603 along another stream. The sixth stream 1609 may be dedicated to methane.

The OCM reactor 1601 can include any vessel, device, system or structure capable of converting at least a portion of the third stream 1606 into one or more $C_{2+}$ compounds using an OCM process. The OCM reactor 1601 can include an adiabatic fixed bed reactor where the combined methane/oxygen gas mixture is passed through a structured bed that can include an active temperature control component (e.g., molten salt cooling system or the like), an isothermal tubular fixed bed reactor where the combined methane/oxygen gas mixture is passed through a structured bed, an adiabatic radial fixed bed reactor where the combined methane/oxygen gas mixture is passed through a structured bed, a fluidized bed reactor where the combined methane/oxygen mixture is used to fluidize a solid catalyst bed, a honeycomb, and/or a membrane type reactor where the combined methane/oxygen mixture passes through an inorganic catalytic membrane. In some cases, a radial fixed bed reactor may be used as the heat loss in the collection volume is minimized when inward flow is used. The cracker section outer wall may be the diffuser of the OCM reactor.

The cracking unit 1602 can be a chamber or a plurality of chambers, such as a plurality of vessels or pipes. The cracking unit 1602 can include inlets for accepting compounds at various locations along the cracking unit 1602. The cracking unit 1602 can have a temperature profile across the cracking unit 1602 and along a direction of fluid flow leading from an inlet of the cracking unit 1602 to an outlet of the cracking unit 1602. In some examples, an upstream portion of the cracking unit 1602 is hotter than a downstream portion of the cracking unit 1602.

The system 1600 can include a mixer upstream of the OCM reactor 1601. The mixer can be employed for use in pre-conditioning OCM reactants, which can prevent the auto-ignition of the reactant gases prior to the OCM process in the OCM reactor 1601.

The cracking unit 1602 may be integrated into one or more unit operations of an overall OCM process system. For instance, although the OCM reactor 1601 and cracking unit 1602 are illustrated in FIG. 16 as separate unit operations, the cracking unit 1602 can be part of the OCM reactor 1601. In some cases, the cracking unit 1602 is positioned immediately adjacent to the catalyst bed within the reactor 1601, so that that the $C_{2+}$ compounds may be more rapidly introduced to the cracking unit 1602. When integrating the OCM reactor 1601 with the cracking unit 1602, improved heat integration can be obtained by using a radial fixed bed reactor.

Figure 17:
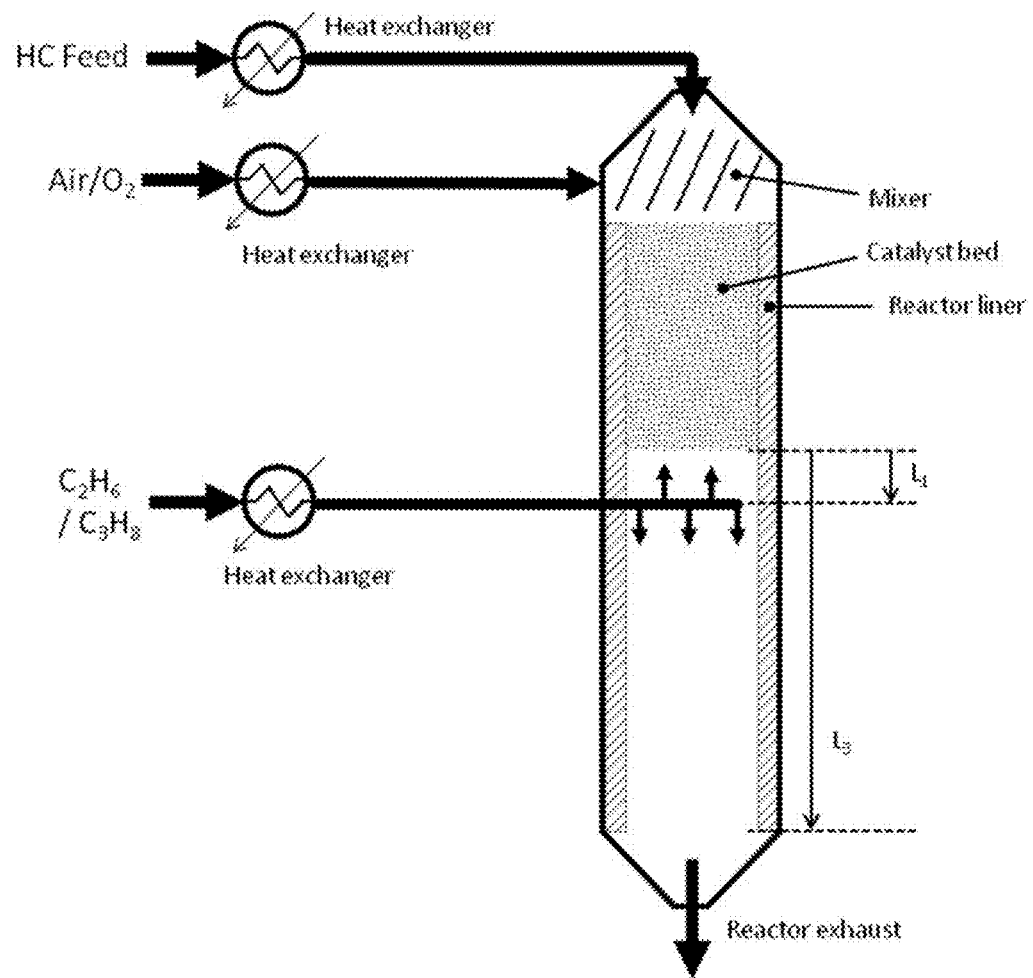
FIG. 17 shows a schematic illustration of an example OCM reactor with alkane injections lines for introducing alkanes to the OCM reactors.

Various approaches can be employed to introduce alkanes to an OCM reactor integrated with a cracking unit. FIG. 17 shows an approach that may be employed. The figure shows an example OCM reactor comprising an OCM catalyst unit with a downstream cracking unit, and ethane and propane injection locations. The catalyst unit can include a catalyst bed. A hydrocarbon feed ("HC feed") may direct a hydrocarbon (e.g., methane) to the OCM reactor, and an air/$O_2$ stream may direct air/$O_2$ to the OCM reactor. The hydrocarbon and air/$O_2$ streams can be directed to a pre-conditioning unit of the OCM reactor, such as a mixer. Ethane and propane can be provided from an external source, such as an NGL processing facility and/or as recycle from an OCM product stream. The hydrocarbon, air/$O_2$, ethane and propane streams can be directed to heat exchangers to preheat the streams prior to introduction to the OCM reactor. In the figures, lengths $L_1$, $L_2$ and $L_3$ can be selected to optimize ethane and propane cracking to desired or otherwise predetermined products, which can be a function of gas temperature and residence time. The ethane injection location is upstream of the propane injection location. In FIG. 17, ethane and propane are injected at the same location (or co-injected).

During use, the hydrocarbon and air/$O_2$ directed into the OCM reactor may react to form OCM products that may be directed along a hydrocarbon-containing stream to the cracking unit and out of the OCM reactor. In the cracking unit, any alkanes in the hydrocarbon-containing stream, including alkanes introduced to the catalyst unit and/or cracking unit from an external source and any alkanes formed in the catalyst unit, can be cracked to alkenes and directed out of the OCM reactor along the hydrocarbon-containing stream.

An aspect of the present disclosure provides mixers and methods of mixing compounds (e.g., ethane and propane) into the cracking unit. Operation of the OCM process with ethane added to the cracking unit can benefit from conditions whereby; (a) ethane is injected into and uniformly mixed with the OCM exhaust gas, and (b) the mixed gases are provided sufficient residence time for conversion prior to thermal quenching. Thermal quenching can halt reactions that yield undesirable hydrocarbon constituents at the expense of ethylene. The mixing of ethane and OCM exhaust gas can be accomplished in a process that is rapid and results in a uniformly blended mixture.

In some cases, high ethylene yields are obtained by providing for residence times between ethane injection and thermal quenching of greater than or equal to about 5 milliseconds (ms), 10 ms, 20 ms, 30 ms, 40 ms, at least about 50 ms, 60 ms, 70 ms, 80 ms, 90 ms, 100 ms, 120 ms, 140 ms, 160 ms, 180 ms, 200 ms, 300 ms, or 400 ms. In some cases, the residence time is less than or equal to about 400 ms, 300 ms, 200 ms, 180 ms, 160 ms, 140 ms, 120 ms, 100 ms, 90 ms, 80 ms, 70 ms, 60 ms, 50 ms, 40 ms, 30 ms, 20 ms, 10 ms, 5 ms, or less. In some cases, the residence time is between any of the two values described above, for example, between about 10 ms and 100 ms, between about 30 ms and about 80 ms, or between about 50 ms and about 60 ms.

In some cases, the alkane (e.g., ethane or propane) is mixed with the OCM exhaust gas uniformly before exiting the mixer, upon exiting the mixer, or prior to initiation of a cracking reaction. The alkane and OCM exhaust gas can be mixed such that the mixed gas has variations in temperature, alkane concentration, or flow rate that do not deviate more than about 1%, 3%, 5%, 10%, 15%, 20%, 25%, 30%, 50%, 60%, or 80% from the average temperature, alkane concentration, or flow rate.

The mixers and mixing processes described herein can result in broad spectrums of mixture ratios. In some cases, the OCM exhaust gas enters the system at a large end of a converging section in an axial direction. Ethane is injected into the converging section through a plurality of ports that can be directed to produce ethane jets having axial, radial and tangential velocity components. The ports can be substantially directed in tangential and radial directions. The converging section can be connected to a duct of smaller diameter (e.g., the reactor). The geometry of the converging and reactor sections (diameters and lengths) can be selected to provide the desired residence times for reactions to occur. In some cases, a heat exchanger is located downstream of and connected to the reactor, which can be utilized to thermally quench the gas stream. The mixer can be made out of materials that can withstand high temperatures (e.g., about 800° C. to 1000° C., which can be the temperature of the OCM exhaust gas). Examples of suitable materials are ceramics such as alumina.

An aspect of the present disclosure provides OCM systems and methods for increasing the concentration of alkenes (or olefins) in $C_{2+}$ compounds outputted from an OCM reactor. An OCM system can provide improved alkene yield by in situ alkane cracking in a post-bed section of a reactor (post-bed cracking). Such in situ cracking of alkanes can provide a product stream with hydrocarbon distributions tailored for various end uses. This can advantageously provide $C_{2+}$ product stream that may be better suited for downstream uses, such as the commercial production of polymeric materials, as well as greater carbon efficiency of the overall process.

Post-bed cracking techniques can comprise control of temperature and residence time. Temperature and residence time can be chosen to favor higher ethylene concentration in the effluent from an OCM reactor. Post-bed cracking can be achieved using energy within the OCM effluent. Post-bed cracking can comprise cracking in the presence of OCM effluent steam. Cracking in the presence of steam, such as OCM effluent steam, can provide a higher $C_2$ ratio. Systems and methods of the present disclosure can be modified by post-bed cracking (PBC) embodiments found in U.S. patent application Ser. No. 14/553,795, which is incorporated herein by reference in its entirety.

The OCM reaction can be performed in an adiabatic reactor, an isothermal reactor, a fluidized bed reactor, or any combination thereof. Adiabatic reactor systems can have many advantages including that they are simple in operation and design and generate useful heat (e.g., steam) for other process steps. Also, the heat generated in the adiabatic system can be used to non-catalytically crack ethane (either created in the OCM reactor added to the reactor) to ethylene. As a result, the ethylene to ethane ratio can be very high exiting the adiabatic reactor system (e.g., about 5%).

In adiabatic reactor systems, the OCM reaction may be limited by the temperature difference between the light-off temperature at the lower end (e.g., temperature at which the OCM reaction initiates for the OCM catalyst) and a maximum temperature at the higher end (e.g., any practical limit imposed by the OCM catalyst, feedstock or product stability). Since the heat of reaction may be retained in the product stream, this temperature difference limits the percentage methane conversion and lower methane conversion can increase the number and size of equipment needed for separation and other processing steps following the OCM reactor.

There are alternative reactor design systems which can allow for higher conversion such as multi-stage adiabatic, fluidized bed and isothermal reactor systems. Isothermal reactor designs (e.g., tubular reactors) continuously remove the heat from the catalyst as it is generated, allowing for high $C_{2+}$ selectivity and very high conversion. One potential downside of isothermal OCM reaction is that the reactor effluent is typically much cooler than for adiabatic reaction and post-bed cracking may not viable (for isothermal) without adding a significant amount of heat.

The present inventors recognized a surprising synergy in combining an isothermal reactor with an adiabatic reactor for exothermic reactions such as OCM. The adiabatic and isothermal reactors may operate in parallel, with a portion of the excess heat and energy from the adiabatic reactor (before or after post bed cracking) being used to convert ethane in the isothermal reactor effluent into ethylene.

Described herein is a reactor system with at least one adiabatic reactor and at least one isothermal reactor. The system can have at least about 1, 2, 3, 4, 5, 6, 7, 8, 9, 10, or more isothermal and/or adiabatic reactors. The reactors may be configured such that heat can be exchanged between them. The excess power generated from the adiabatic reactor can be fed as heat to the vapor space of the reactor outlet of a tubular reactor (without air or oxygen). This can result in cracking of the ethane, increasing the ethylene to ethane ratio, and increasing the ethylene concentration in the isothermal outlet. In some cases, the effluent of the isothermal reactor is injected into the post-bed cracking region of the adiabatic reactor. In some cases, the effluent of the isothermal reactor is combined with the effluent of the isothermal reactor following post-bed cracking in the adiabatic reactor. In some instances, excess ethane is injected into the system (e.g., into the PBC region of the adiabatic reactor or into the combined reactor effluent).

Figure 18:
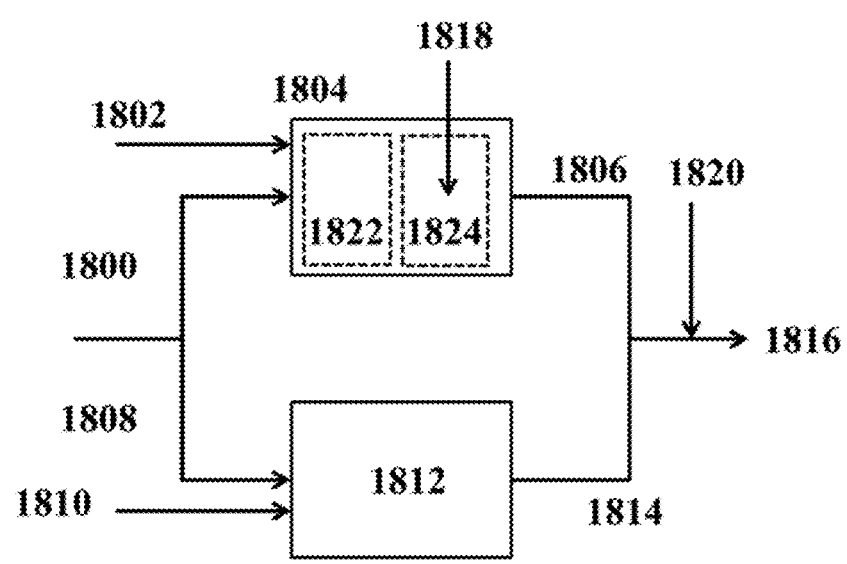
FIG. 18 shows an example OCM system combining an adiabatic reactor and an isothermal reactor.

With reference to FIG. 18, described herein is an example method for performing an oxidative coupling of methane (OCM) reaction. The method can comprise inputting a first portion of methane ($CH_4$) 1800 and a first portion of oxygen ($O_2$) 1802 into a first OCM reactor 1804, where the first OCM reactor is an adiabatic reactor. The method can include, in the first OCM reactor, producing a first product stream 1806 comprising $C_{2+}$ products and liberating a first portion of heat, which first portion of heat increases the temperature of the first product stream. The method can include inputting a second portion of $CH_4$ 1808 and a second portion of oxygen $O_2$ 1810 into a second OCM reactor 1812, where the second OCM reactor is an isothermal reactor. The method can include, in the second OCM reactor, producing a second product stream 1814 comprising $C_{2+}$ products and liberating a second portion of heat, which second portion of heat is removed from the second OCM reactor. In some cases, the method includes combining 1816 the second product stream with the first product stream, whereby the first portion of heat converts ethane ($C_2H_6$) in the first and/or second product stream(s) into ethylene ($C_2H_4$).

In some cases, the method further comprises adding $C_2H_6$ to the first product stream to convert the added $C_2H_6$ into $C_2H_4$. The $C_2H_6$ can be added before 1818 or after 1820 combining the first product stream with the second product stream. The first OCM reactor can have a reaction zone comprising an OCM catalyst 1822 and a post-bed cracking zone 1824. In some cases, the second reactor is a tubular reactor. In some instances, the second reactor is a fluidized bed reactor.

A fluidized bed reactor can be used to pre-heat a methane feed (e.g., natural gas) by running the methane feed in coils within the fluid bed. This can be advantageous relative to the use of a fired heater, as it can be clean, can result in no additional emission heat, and can help the fluidized bed $C_2$ yield by removing heat. In this case, the ratio of the fluidized bed reactor capacity and the adiabatic reactor capacity can be matched to properly pre-heat the methane feed.

The first portion of heat can increase the temperature of the first product stream to at least about 650° C., at least about 700° C., at least about 750° C., at least about 800° C., at least about 850° C., at least about 900° C., or more.

Heat can be removed from the isothermal reactor such that the temperature of the second product stream is less than or equal to about 800° C., 750° C., 700° C., 650° C., 600° C., 550° C., 500° C., 450° C., 400° C., or less. In some cases, the temperature of the isothermal reactor is less than or equal to about 800° C., 750° C., 700° C., 650° C., 600° C., 550° C., 500° C., 450° C., 400° C., or less.

In some cases, the first reactor converts at least about 4%, about 5%, about 6%, about 7%, about 8%, about 9%, about 10%, about 11%, about 12%, about 13%, about 14%, about 15%, about 16%, about 17%, about 18%, about 19%, about 20%, or more of the first portion of $CH_4$ into $C_{2+}$ products. In some cases, the first reactor converts between about 10% and about 13% of the first portion of $CH_4$ into $C_{2+}$ products. The first reactor can convert the first portion of $CH_4$ into $C_{2+}$ products with any $C_{2+}$ selectivity, including between about 55% and about 65% in some instances.

In some cases, the first reactor has a $C_{2+}$ yield that is at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, or more. In some cases, the first reactor has a $C_{2+}$ yield of between about 6% and about 9%.

In some cases, the second reactor converts at least about 15%, about 16%, about 17%, about 18%, about 19%, about 20%, about 21%, about 22%, about 23%, about 24%, about 25%, about 26%, about 27%, about 28%, about 29%, about 30%, or more of the second portion of $CH_4$ into $C_{2+}$ products. In some cases, the second reactor converts between about 20% and about 22% of the second portion of $CH_4$ into $C_{2+}$ products. The second reactor can convert the second portion of $CH_4$ into $C_{2+}$ products with any $C_{2+}$ selectivity, including between about 60% and about 70% in some instances.

In some cases, the second reactor has a $C_{2+}$ yield of at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, or more. In some cases, the second reactor has a $C_{2+}$ yield of between about 12% and about 15%.

In some cases, a ratio of the amount of second product stream to the amount of first product stream is such that the temperature of the combined stream is reduced below about 500° C., below about 450° C., below about 400° C., below about 350° C., below about 300° C., or below about 250° C. following conversion of $C_2H_6$ into $C_2H_4$.

Systems and Methods for Heat Exchange

Several process industries, including petrochemicals and refining, make extensive use of heat exchangers to cool and/or heat process streams (i.e., fluids) to a target temperature and/or to manage the heat generated and/or consumed by the process. Current heat exchangers suffer from many limitations, including but not limited to a change in duty and steam production as well as a shift in exit temperature of the fluid as the heat exchanger becomes fouled during its operation.

The present disclosure provides heat exchange devices (or apparatuses), and methods for heat exchange and systems incorporating heat exchange (e.g., for performing oxidative coupling of methane). The present heat exchangers and methods can (a) achieve high heat exchange rates until a target temperature is reached (e.g., to quench a reaction), (b) keep the overall duty and steam production relatively constant as the heat exchanger fouls, (c) maintain a relatively constant and high exit temperature of steam generated in cooling a process stream so as to be able to benefit from the quality of the heat (exergy) for downstream processes, and (d) achieve a long service time before cleaning the heat exchanger.

Figure 19A:
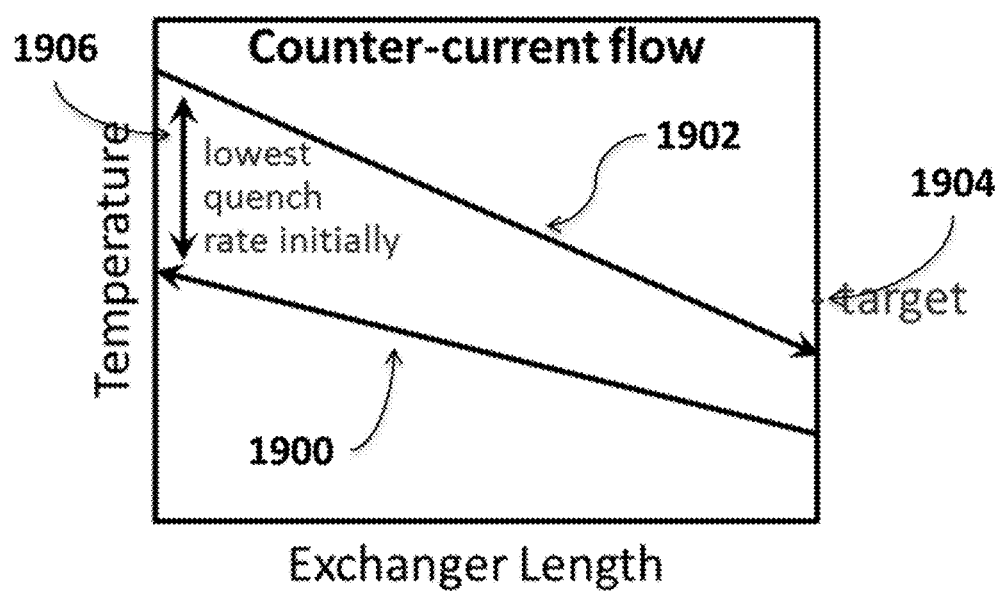
FIGS. 19A-19D are graphs of temperature versus exchanger length for different example heat recovery methods.
Figure 19B:
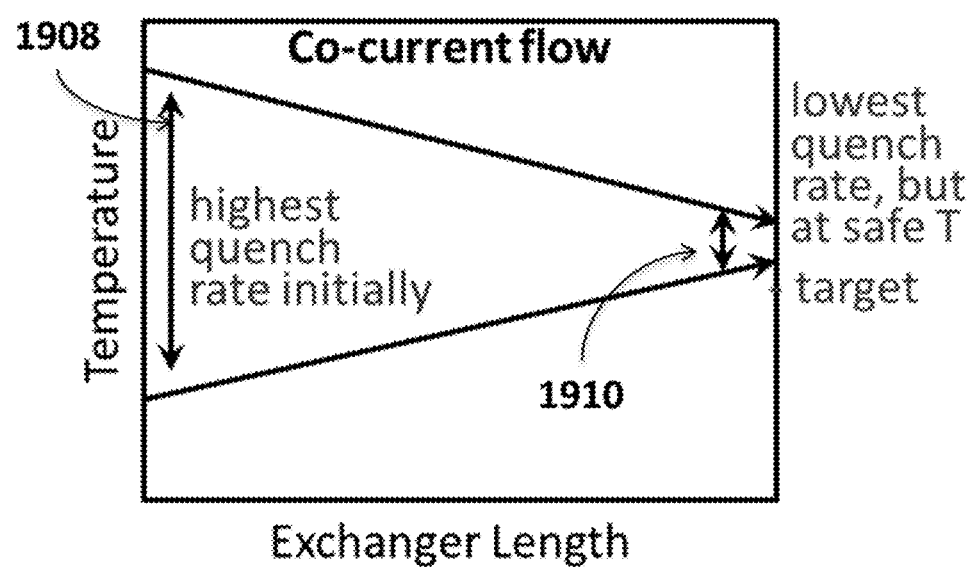
Figure 19C:
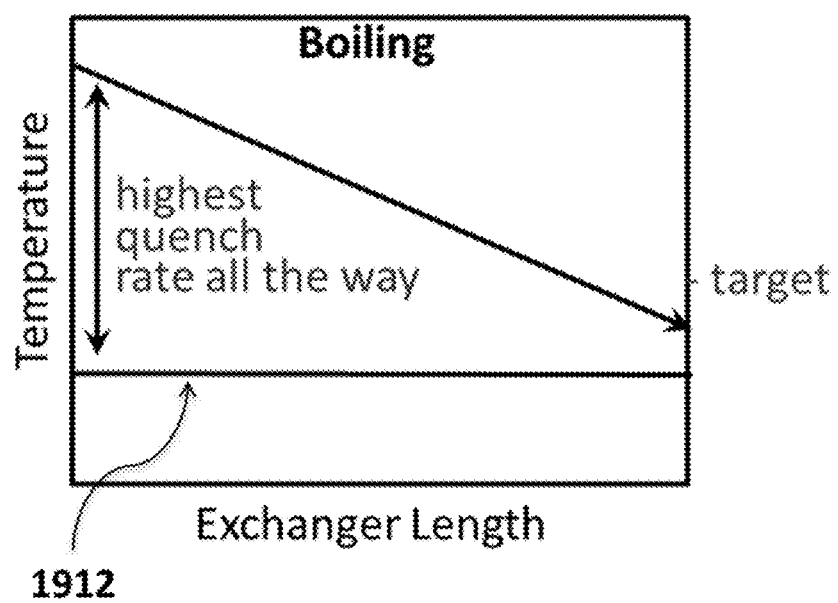

Heat exchange can be performed in a variety of ways including but not limited to counter-current flow, co-current flow and boiling, each of which can have various advantages and disadvantages. FIG. 19A shows a graph of temperature versus exchanger length for counter-current flow. The process fluids may move through the heat exchanger in opposite directions where one fluid may be heated 1900 using energy derived from a second fluid 1902. The second fluid can be cooled to a target temperature 1904, e.g., such that a chemical reaction is quenched. The quench rate can be proportional to the temperature difference between the two fluids and is initially 1906 relatively lower for counter-current flow compared with co-current flow and boiling, which can be disadvantageous when a rapid quench rate is desired. Furthermore, the exit temperature may be lower than the target temperature. In contrast, as shown in FIG. 19B, co-current flow may have a higher initial quench rate 1908, but a low quench rate near the exit from the exchanger 1910. Co-current exchangers can have a larger size (i.e., are more expensive) than counter-current exchangers. Furthermore, the exit temperature may be lower than the target temperature. With reference to FIG. 19C, boiling can have a high quench rate throughout and be performed in smaller equipment than for co-current flow. In this case, the temperature of the first fluid doesn't increase 1912 because the energy goes to boiling the fluid. Furthermore, the exit temperature may be lower than the target temperature.

Figure 19D:
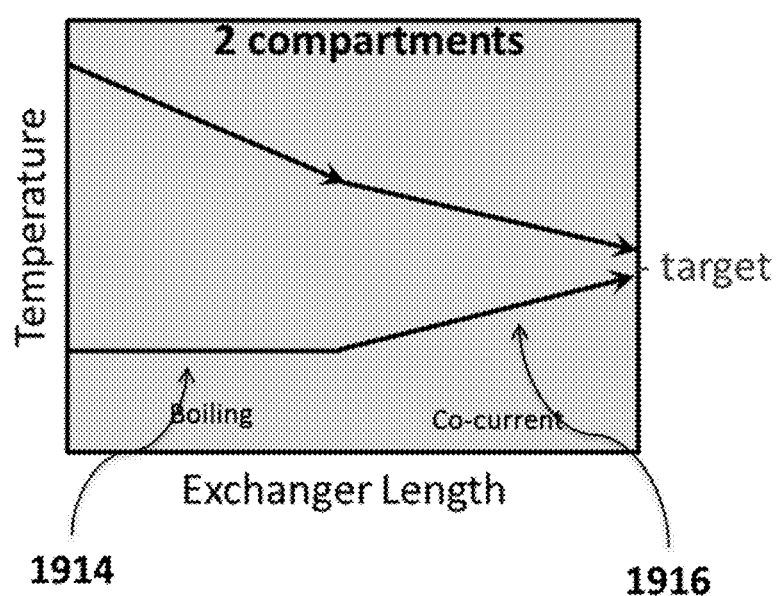

In some cases, the apparatus and methods may use a combination of boiling and co-current heat exchange. When the heat exchange medium is water, the process may produce steam then super-heats the steam. As shown in FIG. 19D, boiling 1914 and co-current heat exchange 1916 can be performed sequentially, e.g., in two adjoining chambers of the heat exchangers described herein. This design can simultaneously achieve several design objectives including rapid quenching and reliably meeting a target temperature, especially as the apparatus becomes fouled over time due to operation (e.g., deposition of material providing a heat resistance on heat exchange surfaces).

Figure 20:
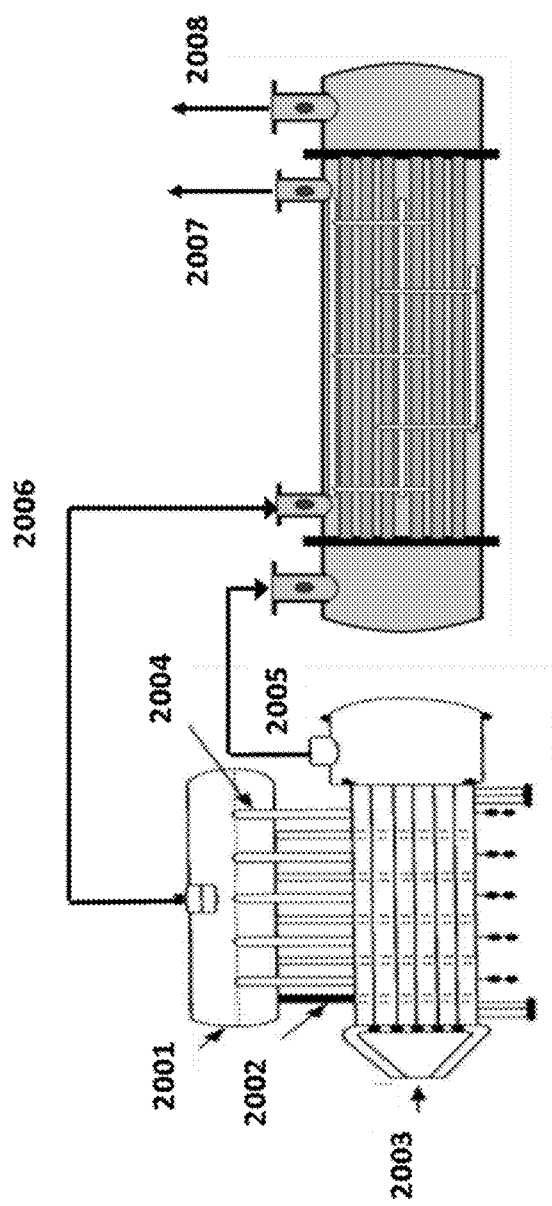
FIG. 20 is diagram of two separate example heat exchangers.

FIG. 20 is a diagram of two separate heat exchangers representing the process of FIG. 19D. A hot fluid, such as a process gas or process stream, may enter a first heat exchanger at an inlet 2003 and may exit the first heat exchanger at an outlet 2005. The process gas exiting the first heat exchanger may subsequently enter a second heat exchanger at an inlet and exit the second heat exchanger at an outlet 2008. Heat may be transmitted from the process gas to water contained inside a boiler, 2001, to turn it into saturated steam and be conveyed to the steam drum via riser pipes 2004. The saturated steam may exit the steam drum 2001 at an outlet 2006. The saturated steam exiting the steam drum may then enter an inlet to the second heat exchanger at an inlet. Superheated steam may exit the second heat exchanger at an outlet 2007. Down-comer pipe 2002 may fluidically connect the steam drum to the heat exchanger and allow saturated water that collects at the bottom of the steam drum to flow through a plurality of down-comer pipes, such as down-comer pipe 2002.

Figure 21:
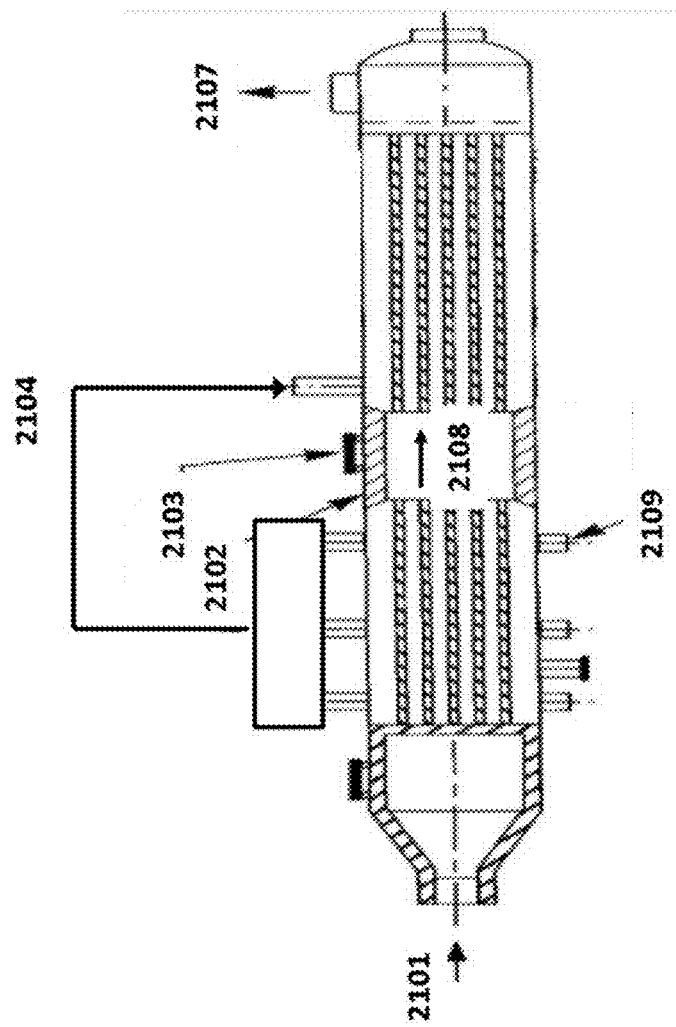
FIG. 21 is diagram of an example dual compartment heat exchanger with process gas cross-over duct.

FIG. 21 is a diagram of a single dual compartment heat exchanger for implementing the process shown in FIG. 19D comprising a first compartment and a second compartment connected by a cross-over duct 2108. A hot fluid, such as a process gas or process stream, may enter the single heat exchanger at an inlet 2101 on a first compartment and exit the single heat exchanger at an outlet 2107 on a second compartment. Heat may be transmitted from the process to water contained inside a boiler to turn it into saturated steam to be conveyed to the stream drum via riser pipes. The saturated steam may exit the steam drum at an outlet 2104 on the steam drum and enter the second compartment. Superheated steam may exit the second compartment of the dual heat exchanger at an outlet 2107. A plurality of down-comer pipes, such as down-comer pipe 2109, may fluidically connect the steam drum to the heat exchanger and allow saturated water that collects at the bottom of the steam drum to flow through the plurality of down-comer pipes. The apparatus can have a man-way 2103 that passes through the intermediate channel 2102.

Figure 22:
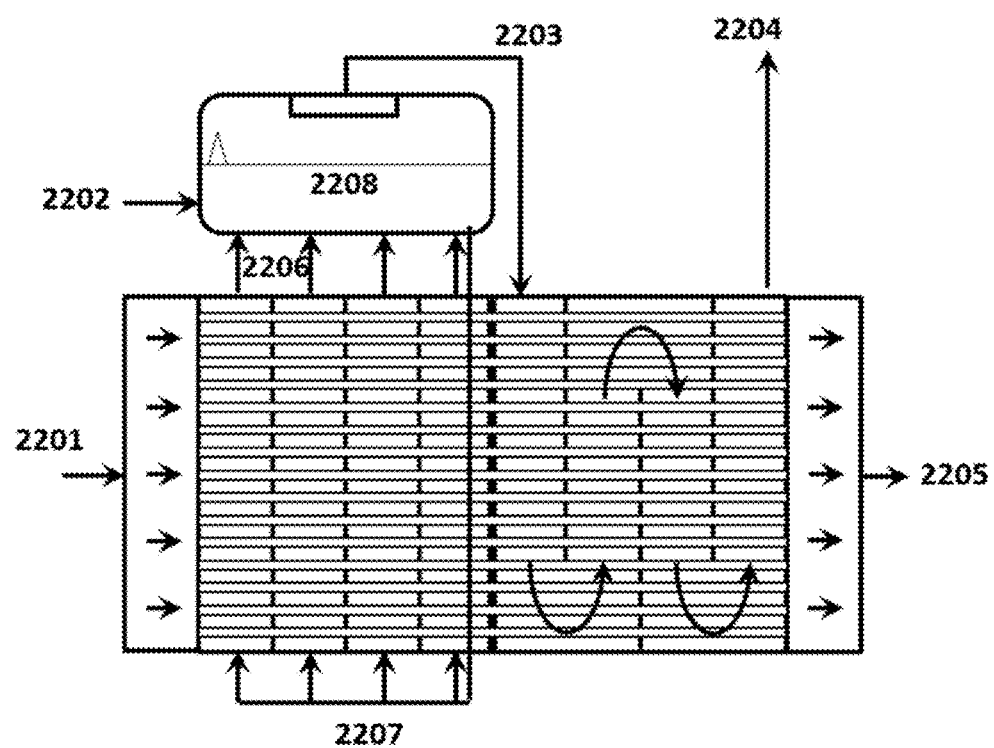
FIG. 22 is a diagram of an example dual compartment heat exchanger without process gas cross-over duct.

FIG. 22 is a diagram of an alternative to the apparatus of FIG. 20 and FIG. 21 for performing boiling followed by co-current heat exchange. The apparatus of FIG. 22 is a dual compartment heat exchanger which that may reduce the undesirable properties of the heat exchangers. A hot fluid, such as a process gas or process stream, may enter a single heat exchanger at an inlet 2201 on a first compartment (such as a steam generator) and exit the heat exchanger at an outlet 2205 on a second compartment (such as a super heater). Parallel or co-current flow of the process gas and saturated steam may occur in the second compartment of the heat exchanger. Heat may be transmitted from the process fluid to water contained inside a boiler to turn it into saturated steam that can be conveyed to the steam drum via riser pipes 2206. The saturated steam may exit the steam drum 2208 at an outlet 2203 on the steam drum and enter the second compartment at an inlet. Superheated steam may exit the second compartment of the dual heat exchanger at an outlet 2204. A plurality of down-comer pipes, such as down-comer pipe 2207, may connect the steam drum to the heat exchanger and allow saturated water that may collect at the bottom of the steam drum to flow through the down-comer pipe. A two-phase flow may enter the steam drum from the riser pipe 2206.

Figure 23:
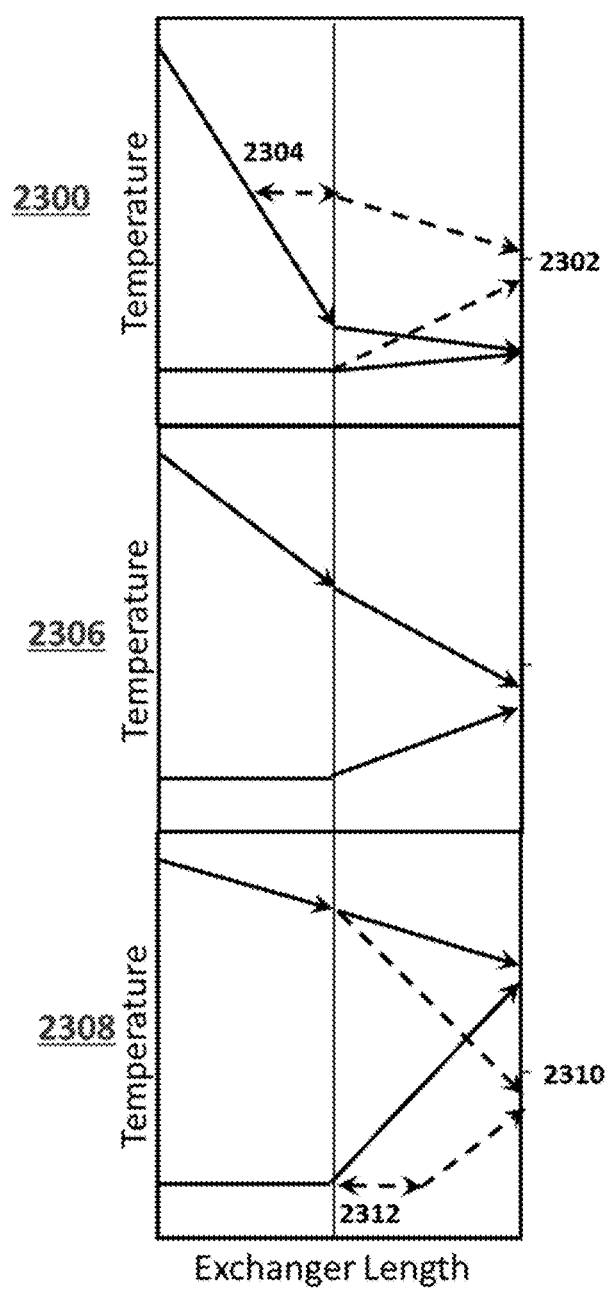
FIG. 23 shows the effect of fouling on steam generation and superheat.

FIG. 23 is a three panel graph plotting temperature (vertical axis with higher temperatures at the top) of the process gas against heat exchanger length (horizontal axis with beginning of the reactor on the left) for the combined boiling and heat exchange system shown in FIG. 19D (where the two chambers are separated by a vertical line). The top panel 2300 represents the beginning of a process run in which the system may be clean and have little or no fouling. In this case, (following the solid lines) as the process gas travels along the length of the heat exchanger from an inlet to an outlet, the process gas temperature may become too low, such as lower than the target temperature 2302 at the outlet of the second compartment, and there may be insufficient steam superheat. In some cases, more than desirable heat from the process fluid can go into boiling and less into steam super-heating. Following the dashed lines, the exit temperature can be corrected to match the target temperature by performing less boiling 2304 in the first chamber.

The middle panel 2306 represents a midpoint of a process run in which the system may have an intermediate amount of fouling that is the design condition. In this case, as the process gas travels along the length of the heat exchanger from an inlet to an outlet, the change in process gas temperature and steam superheat temperature may be desirable. A system with a given amount of fouling, not heavily fouled, and not without fouling, may produce a desirable or optimal change in temperature across a length of a heat exchanger and generation of steam super-heat.

The bottom panel 2308 represents the end of a process run in which the system may be heavily fouled. In this case, (following the solid lines) as the process gas travels along the length of the heat exchanger from an inlet to an outlet, the process gas temperature, the tube skin temperature, and the temperature of the steam superheat may become too high, such as higher than the target temperature 2310 at the outlet of the second compartment. In some cases, less than a desirable amount of heat from the process can go into boiling and more into steam super-heating. Following the dashed lines, the exit temperature can be corrected to match the target temperature by performing more boiling 2312 in the heat exchanger.

Figure 24A:
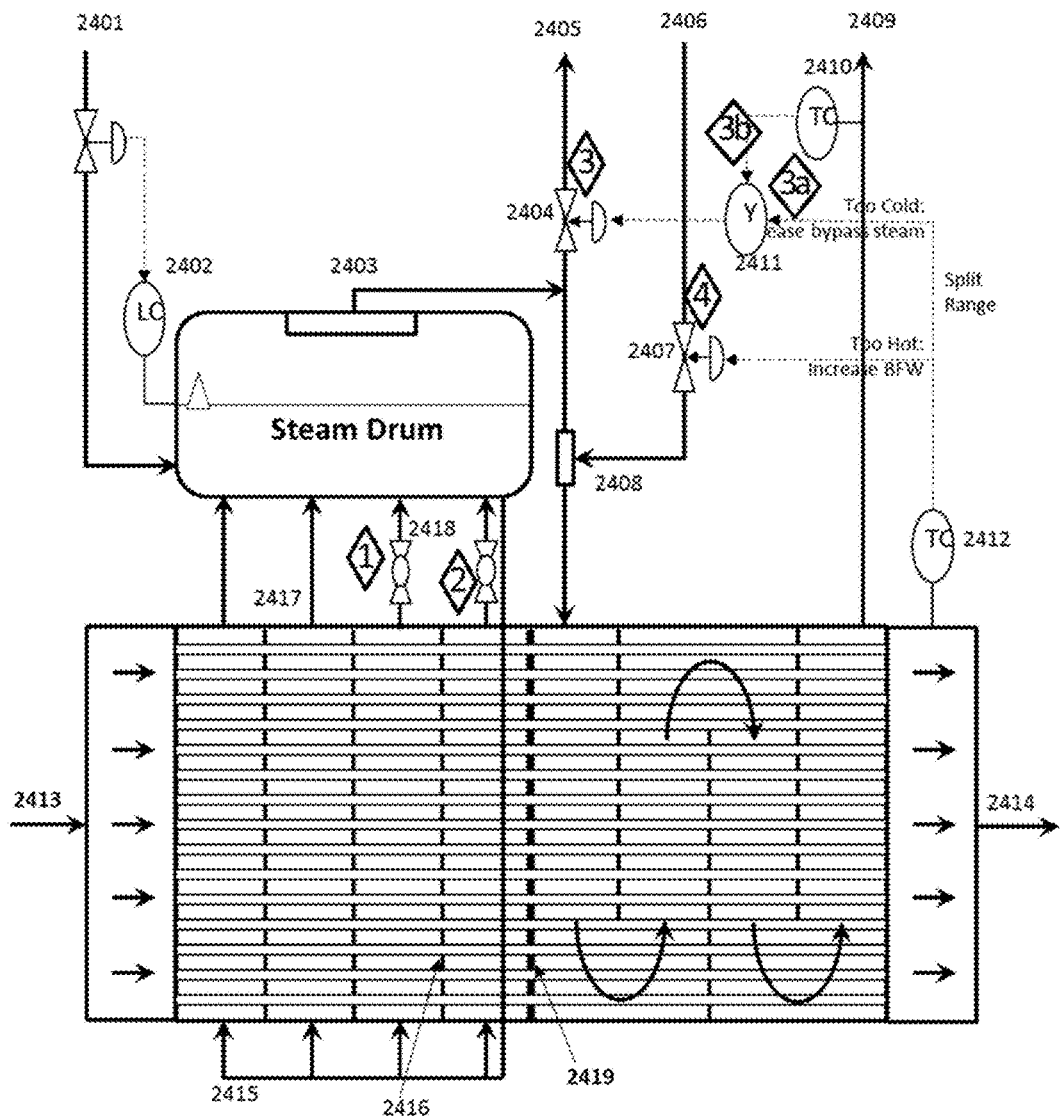
FIG. 24A is a process flow diagram of an example steam generator and superheater combination.
Figure 24B:
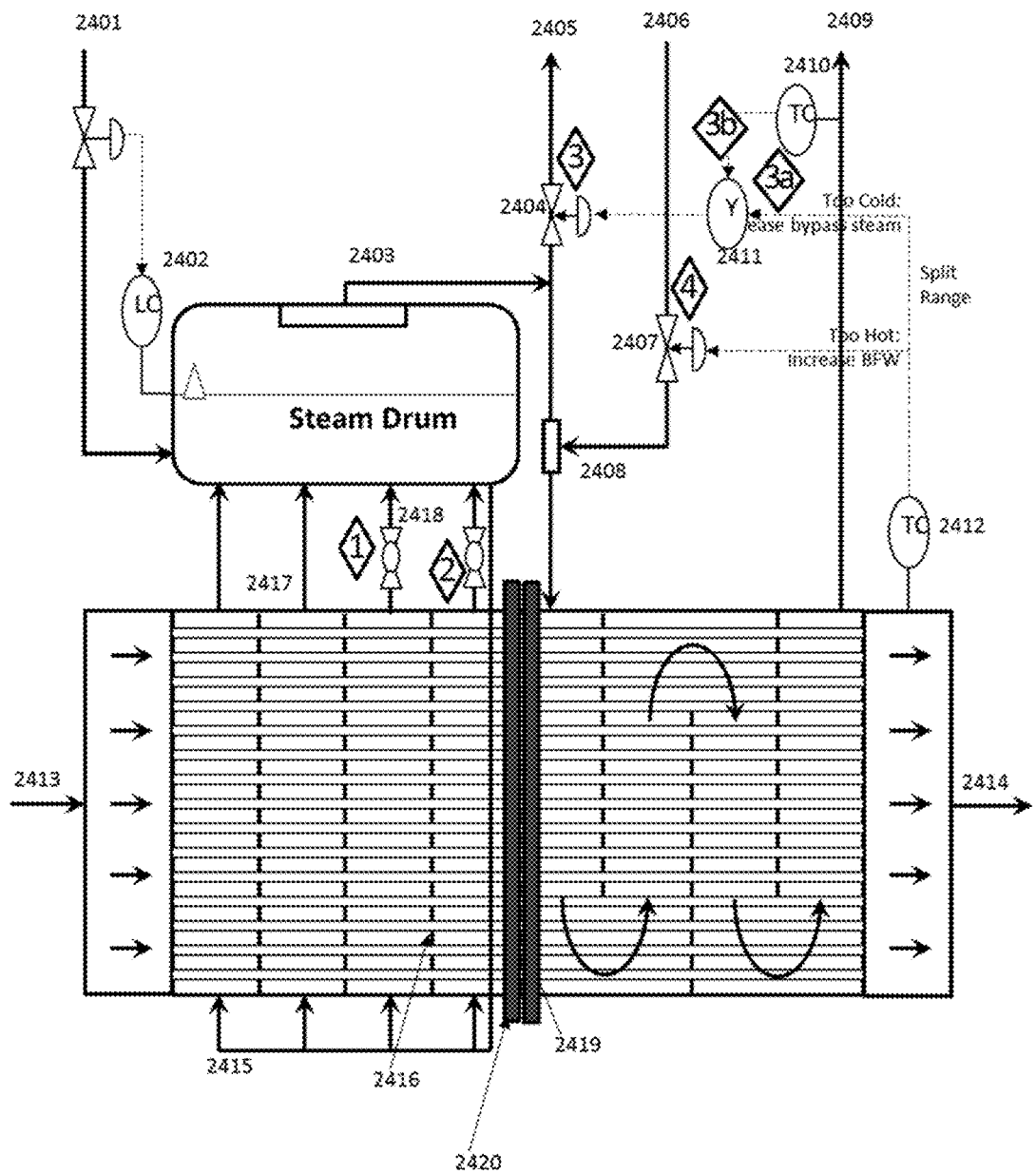
FIG. 24B is a process flow diagram of an example steam generator and superheater combination with a double flange and gasket.
Figure 24C:
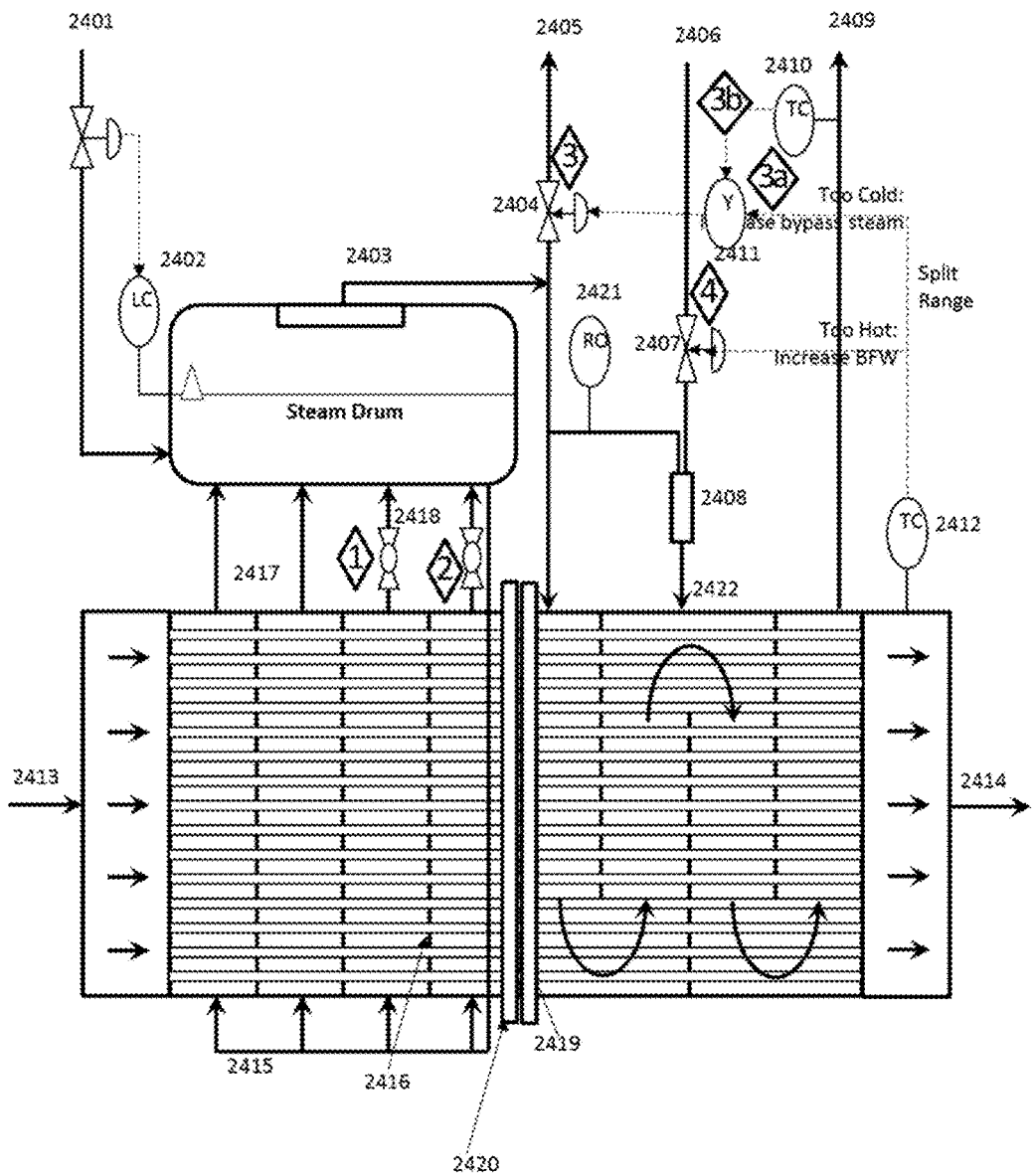
FIG. 24C is a process flow diagram of an example steam generator and superheater combination with a double flange and gasket.

FIGS. 24A-C provide examples of dual compartment heat exchangers without a cross-over duct. These dual compartment examples combine a first compartment (such as a steam generator) and a second compartment (such as a superheater with co-current flow). Positioned between the first compartment and the second compartment may be a thick baffle or tube-sheet 2419. This thick baffle can be different than the plurality of baffles, such as baffle 2416, positioned within the first and second compartments. The plurality of baffles may be used to support the tubes or may be used as a flow guiding element, e.g., to optimize heat transmission. The thick baffle may be used to separate the boiling water from the superheat steam side of the chambers and can be enhanced by a seal, by welding, by roll welding, or by explosion welding. The thick baffle may be positioned angled (e.g., perpendicular) with respect to the plurality of baffles within the first or second compartments. The angle may be at least about 5°, 10°, 20°, 30°, 40°, 45°, 50°, 60°, 70°, 80° or 90°. A dual compartment heat exchanger, as shown in FIGS. 24A-C, comprising a thick baffle positioned substantially perpendicularly between a first and second compartments can yield changes in process gas temperature than may be suitable across a wide range of process fouling amounts. The thick baffle may be angled with respect to the first and second compartments. The angle may be at least about 5°, 10°, 20°, 30°, 40°, 45°, 50°, 60°, 70°, 80° or 90°. For example, the system configuration of FIGS. 24A-C may quench the process gas across the length of the heat exchanger to arrive at the desired target temperature at the outlet for a system that is clean, for a system that is heavily fouled, and for a system that is moderately fouled.

FIG. 24A shows that a process gas may enter the dual compartment heat exchanger at an inlet 2413 on the first compartment. The process gas may enter the heat exchanger at an initial temperature. The process gas that enters the heat exchanger may be process gas that has recently exited an OCM unit and/or a post-bed cracking (PBC) unit. For example, the process gas that enters the heat exchange may be an OCM effluent stream. The process gas may exit the dual compartment heat exchanger at an outlet 2414 on the second compartment. The process gas may exit the heat exchanger at an exit temperature (e.g., of about 500° C. for OCM). The process gas that exits the heat exchanger may be directed to a heater, such as a natural gas heater. The first and second compartments of the heat exchanger may comprise a plurality of baffles, such as baffle 2416. The first and/or second compartment may be over-sized to allow flexibility in operation. The first compartment of the heat exchanger may be connected to a steam drum by a plurality of down-comer pipes, such as down-comer pipe 2415 in which condensed water 2417 may enter the bottom of the boiler. Boiler feed water may enter the steam drum at an inlet 2401. A level sensor 2402 may measure the level of fluid in the steam drum and adjust the valve at inlet 2401 to prevent the steam drum from overfilling or becoming empty of fluid. Saturated steam may exit the steam drum at an outlet 2403. The saturated steam exiting the steam drum may be split into a first and second line. The first line may direct the saturated steam through a blast or shear atomizer 2408 and subsequently onto to the second compartment of the heat exchanger. The second line may pass the saturated steam through a valve 2404 and exit the system at outlet 2405. Superheated steam may exit the system at an outlet 2409 on the second compartment of the heat exchanger. A temperature sensor 2410 may be positioned adjacent to the outlet 2409. The temperature sensor 2410 may measure the temperature of the superheated steam at outlet 2409 in comparison to a set temperature. An additional inlet flow line of boiler feed water 2406 may be added to the system via a valve 2407 directing the boiler feed water into the blast or shear atomizer 2408. A temperature sensor 2412 may be positioned adjacent the outlet 2414 of the second compartment. The temperature sensor 2412 may measure the temperature of the process gas at inlet 2413 in comparison to a set temperature. At high fouling rates, if the process gas exiting the second compartment of the heat exchanger is above the set temperature, then more cooling duty is required via additional boiling. Valve 2407 may be adjusted to permit additional boiler feed water to enter the system at inlet 2406.

At high fouling rates, the superheated steam exiting the second chamber can be above the target temperature, then the valve 2407 may be adjusted to permit additional boiler feed water to enter the system at the inlet 2406. The selector 2411 can prioritize the action from the signals provided by the temperature sensor for the process gas 2412 and by the temperature sensor for the superheated steam 2410.

If the process gas exiting the second compartment of the heat exchange is below the set temperature, then less cooling duty is required. This can be achieved by (a) reducing the cooling duty in the second compartment by arranging for a smaller steam flow to be superheated, e.g., bypassing via 2405 or (b) reducing the cooling duty in the first chamber.

FIG. 24B shows an alternative to FIG. 24A with a dual compartment heat exchanger. FIG. 24B shows a dual compartment heat exchanger with a double flange and gasket 2420 positioned between the first and second compartments.

FIG. 24C shows an alternative to FIG. 24A and FIG. 24B. Similar to FIG. 24B, FIG. 24C also includes the double flange and gasket 2420 positioned between the first and second compartment. In addition, the system shown in FIG. 24C also splits the line of saturated steam entering the second compartment into a first and second line. The first line of saturated steam may enter the second compartment directly. The second line may pass through a restriction orifice 2421 and then into the blast or shear atomizer 2408 before entering the second compartment at inlet 2422 to be desuperheated to some extent, with the main steam flow to be superheated.

Figure 25:
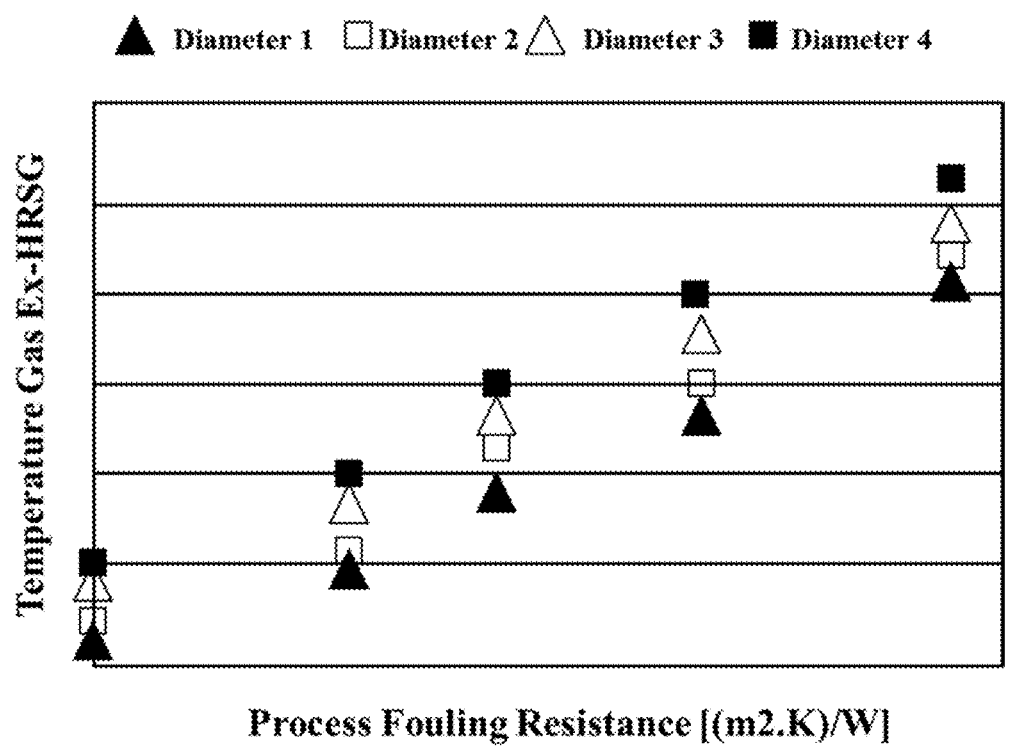
FIG. 25 is a graph of temperature gas exiting an example heat recovery steam generator (HRSG) versus process fouling resistance.

FIG. 25 shows the effect of fouling on the temperature of a process gas exiting a dual compartment heat exchanger with steam generation. FIG. 25 plots the amount of process fouling, measured as process fouling resistance (meters squared Kelvins per Watts or m2·K/W), against temperature of the process gas exiting the heat recovery steam generator (HRSG). A target temperature of the process gas exiting the heat exchanger may be lower than the temperature of the process gas at the inlet to the heat exchanger. The temperature of the process gas exiting the heat exchanger may vary with a diameter of a tube sheet, such as an outer diameter. For example, the temperature of the process gas may vary +/−50° C. over a diameter range of about 1.0 meters to about 1.5 meters. When there is no process fouling or the system is clean or the system is at a beginning of a run, the exit temperature of the process gas may be below a target temperature. When there is fouling present in a system, such as in the middle of a run, or the amount of process fouling is between about 0.005 and 0.001 m2·K/W fouling resistance, the exit temperature of the process gas may be near the design case. When there is heavy fouling in a system, such as at the end of a run, or the amount of process fouling is between about 0.002 and 0.003 m2·K/W fouling resistance, the exit temperature of the process gas may be too high. Temperature of the process gas exiting the heat exchanger may increase with increased process fouling.

FIG. 26 shows an example of how to operate a heat exchanger of the present disclosure as the heat exchanger becomes fouled. FIG. 26 designates numeric indicators for differing amounts of process fouling. In this case, "level 1" indicates little or no fouling "level 4" indicates heavy fouling, and "level 2" and "level 3" are intermediate values. For example "level 1" can be a process fouling resistance from between about 0.0000 and about 0.00025 meters squared Kelvin per Watts (m2·K/W); "level 2" can be a process fouling resistance from between about 0.000025 to about 0.0006 m2·K/W; "level 3" can be a process fouling resistance from between about 0.0006 to about 0.0018 m2·K/W; and "level 4" can be a process fouling resistance from between about 0.0018 to about 0.003 m2·K/W.

FIG. 26 shows a table of control functions, such as valves and controllers that are also shown in the process diagrams of FIG. 24A-C. For example, control function <1>, as shown in the table of FIG. 26 and also in FIG. 24A-C, may be a valve positioned between the first compartment and the steam drum at a middle section along the length of the first compartment. Control function <2>, as shown in the table of FIG. 26 and also in FIG. 24A-C, may be a valve positioned between the first compartment and the steam drum at a distal end of the first compartment. Control functions <3a>, and <3b> may be temperature controllers that act on a steam bypass valve <3>. Control function <4> may be a temperature controller that acts on boiler feed water (BFW) injection. As shown in FIG. 26, at low fouling resistance of "level 1", valves <1> and <2> can be left in the closed position, temperature controllers <3a> and <3b> can be active, and temperature controller <4> can be off. At an intermediate fouling resistance of "level 2", valve <1> can be in the open position, valve <2> can be in the closed position, temperature controllers <3a> and <3b> can be active, and temperature controller <4> can be off. At an intermediate fouling resistance of "level 3", valves <1> and <2> can be in the open position, temperature controllers <3a> and <3b> can be active, and temperature controller <4> can be active. At an high fouling resistance of "level 4", valves <1> and <2> can be in the open position, temperature controllers <3a> and <3b> can be off, and temperature controller <4> can be active.

Figure 27:
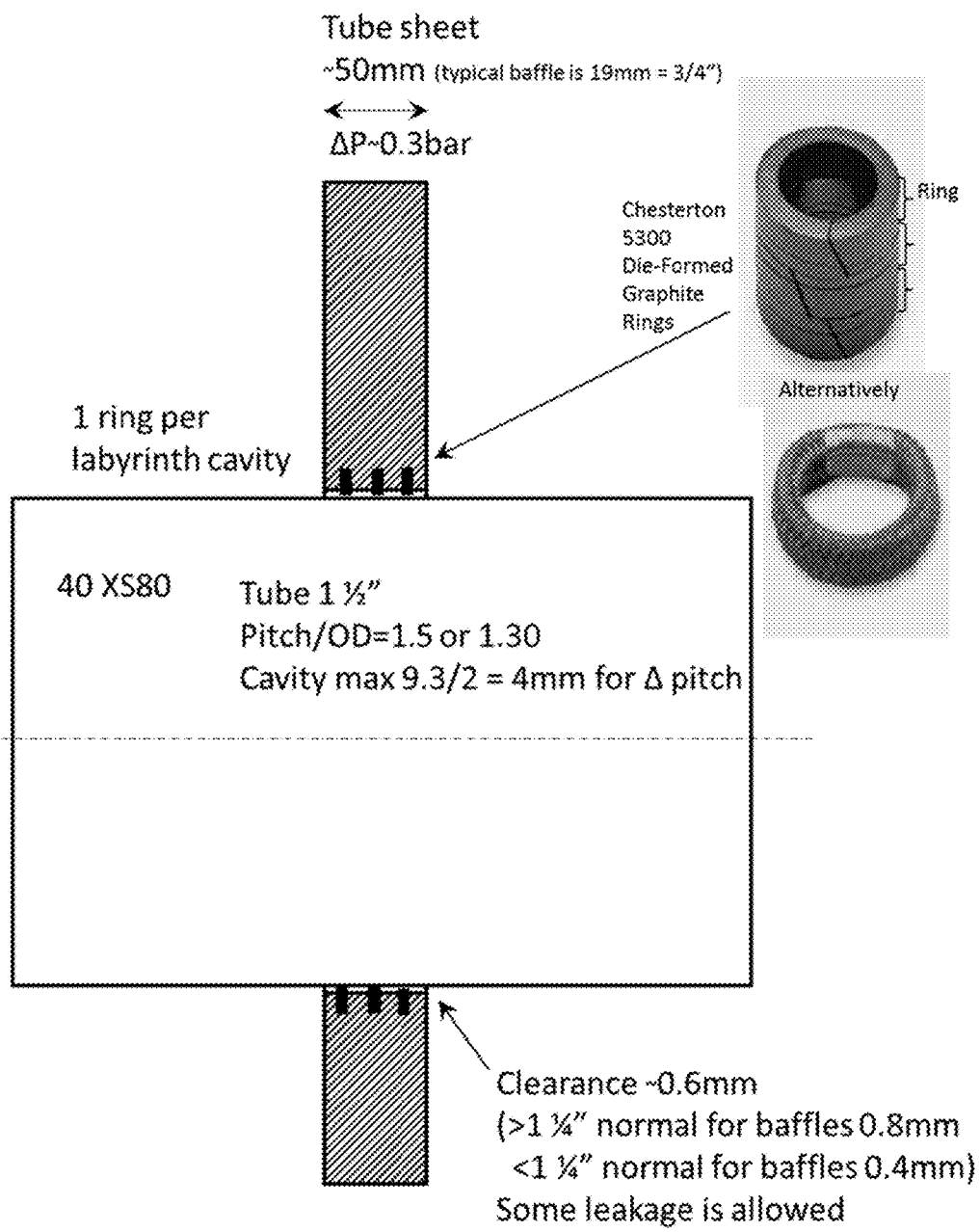
FIG. 27 is a diagram of an example tick baffle or tube sheet.

FIG. 27 shows an example of a tick baffle or tube sheet. The tube sheet may have a labyrinth seal. The tube sheet may have a plurality of cavities. The tube sheet may have two cavities. The tube sheet may have three cavities. The tube sheet may have four cavities. The tube sheet may have five or more cavities. The tube sheet may comprise a single ring per cavity. The tube sheet may comprise a plurality of rings per cavity, such as two rings, three rings, four rings, or more.

System components, such as heat exchangers may be subject to fouling during the course of a system run. The amount of fouling may change the amount of steam production. The amount of fouling may shift an exit temperature of one or both of the heat exchanging fluids, such as the process gas and saturated steam. Several advantages of the present invention may include a) achieving high quench rates of the process gas until reactions are frozen; b) maintaining the overall duty or steam production at a constant value; c) maintaining a high exit temperature of the heat exchanging media to benefit from the quality of the heat for downstream processes; and d) achieving a long service time between cleaning cycles; and any combination thereof.

The dual compartment heat exchanger may be a fire-tube heat exchanger. The dual compartment heat exchanger may comprise a first compartment comprising a fixed boiler and a second compartment comprising a fixed super-heater. The fixed super-heater may comprise co-current flow of the process gas and saturated steam. The fixed super-heater may comprise counter-current flow of the process gas and saturated steam.

In some cases, when the surfaces of the first compartment are clean or non-fouled, then the steam production may be higher than a desired amount, the process gas outlet temperature may be lower than a desired temperature, or a combination thereof. To reduce the amount of steam production, the waterside heat transfer may be reduced via steam-pocketing one or more sections in the fixed boiler compartment comprising a plurality of baffles. Closing one or more valves in one or more risers to a steam drum may prevent steam-water buoyancy to the steam drum.

Heat exchange may be matched for all fouling conditions (clean, slightly fouled, moderately fouled, heavily fouled), by using a co-current or a parallel heat exchanger that has a larger surface area (i.e., overdesigned). Exit temperature of the process gas exiting the second compartment may be tuned by a variety of ways. For example, if the temperature of the process gas is too high at the outlet to the second compartment (such as, e.g., higher than the target temperature specified at the outlet to the second compartment), then water may be injected with the feed of saturated steam at the inlet of the second compartment. The mass of injected water may be subject to boiling and superheat at the expense of the process gas outlet temperature. If the temperature of the process gas at the outlet to the second compartment is low (such as lower than the target temperature specified at the outlet to the second compartment), then the feed of saturated steam can be reduced. With less feed of steam, the balance of heat exchange may shift to increase the process gas temperature at the outlet of the second compartment. Alternatively, if the temperature is superheated steam at the outlet is too low (such as lower than the target temperature specified at the outlet to the second compartment), then the feed of saturated steam may be reduced. Reducing the feed of steam, the balance of heat exchange may shift to increase the temperature of the superheated steam at the outlet.

Employing systems as disclosed herein, saturated steam may be superheated to a desired temperature, for example, at about 500° C. The quantity and temperature of the produced superheated steam may be fairly indifferent to the state of fouling. The process gas at the outlet may have a target temperature, for example, at about 500° C. for further process integration. The temperature of the process gas at the outlet may be fairly indifferent to the state of fouling.

The length of a first compartment and a second compartment of a dual compartment heat exchanger may be same or different. The length of a first compartment, a second compartment, or a combination thereof may be configured to influence a pressure drop across a dual compartment heat exchanger. The length of a first compartment, a second compartment, or a combination thereof may be configured to accommodate a wide variety of process fouling and still reduce a process gas to a target temperature at the outlet to the second compartment. The first compartment length may be shorter than the second compartment length. The first compartment length may be about 0.4%, 0.5%, 0.6%, 0.7%, 0.8%, 0.9% or less shorter in length compared to the second compartment. The first compartment may be greater than or equal to about 2 meters (m), 3 m, 4 m, 5 m, 6 m, 7 m, 8 m, 9 m, 10 m, 11 m, 12 m, 13 m, 14 m, 15 m or more in length. The second compartment may be greater than or equal to about 3 meters (m), 4 m, 5 m, 6 m, 7 m, 8 m, 9 m, 10 m, 11 m, 12 m, 13 m, 14 m, 15 m, 16 m, 17 m, 18 m, 19 m, 20 m or more in length. In some examples, the first compartment may be about 4 meters in length and the second compartment may be about 6 meters in length.

The temperature of the process gas entering the dual compartment heat exchanger may change along the length of the exchanger. The temperature of the process gas entering the dual compartment heat exchanger may be different than the exit temperature. The temperature of the fluid entering the heat exchanger may be higher than the temperature of the fluid exiting the heat exchanger. The temperature of the fluid exiting the heat exchanger may be about 250° C. lower than the temperature of the fluid entering the heat exchanger. The temperature of the fluid exiting the heat exchanger may be about 275° C. lower than the temperature of the fluid entering the heat exchanger. The temperature of the fluid exiting the heat exchanger may be about 300° C. lower than the temperature of the fluid entering the heat exchanger. The temperature of the fluid exiting the heat exchanger may be about 325° C. lower than the temperature of the fluid entering the heat exchanger. The temperature of the fluid exiting the heat exchanger may be about 350° C. lower than the temperature of the fluid entering the heat exchanger. The temperature of the fluid exiting the heat exchanger may be about 375° C. lower than the temperature of the fluid entering the heat exchanger. The temperature of the fluid exiting the heat exchanger may be at least about 100° C., 125° C., 150° C., 175° C., 200° C., 205° C., 210° C., 215° C., 220° C., 225° C., 230° C., 235° C., 240° C., 245° C., 250° C., 255° C., 260° C., 265° C., 270° C., 275° C., 280° C., 285° C., 290° C., 295° C., 300° C., 305° C., 310° C., 315° C., 320° C., 325° C., 330° C., 335° C., 340° C., 345° C., 350° C., 355° C., 360° C., 365° C., 370° C., 375° C., 380° C., 385° C., 390° C., 395° C., 400° C., 425° C., 450° C., 475° C., 500° C. lower than the temperature of the fluid entering the heat exchanger.

The temperature of the fluid exiting the heat exchanger may be about 1% less than the temperature of the fluid entering the heat exchanger. The temperature of the fluid exiting the heat exchanger may be about 1.25% less than the temperature of the fluid entering the heat exchanger. The temperature of the fluid exiting the heat exchanger may be about 1.5% less than the temperature of the fluid entering the heat exchanger. The temperature of the fluid exiting the heat exchanger may be about 1.75% less than the temperature of the fluid entering the heat exchanger. The temperature of the fluid exiting the heat exchanger may be about 2% less than the temperature of the fluid entering the heat exchanger. The temperature of the fluid exiting the heat exchanger may be about 2.25% less than the temperature of the fluid entering the heat exchanger. The temperature of the fluid exiting the heat exchanger may be at least about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5% less than the temperature of the fluid entering the heat exchanger.

Control Systems

The present disclosure provides computer control systems that can be employed to regulate or otherwise control the heat exchanger apparatus, methods and systems provided herein. A control system of the present disclosure can be programmed to control process parameters to, for example, effect a given product, such as a higher concentration of alkenes as compared to alkanes in a product stream out of an oxidative coupling of methane (OCM) process.

Figure 28:
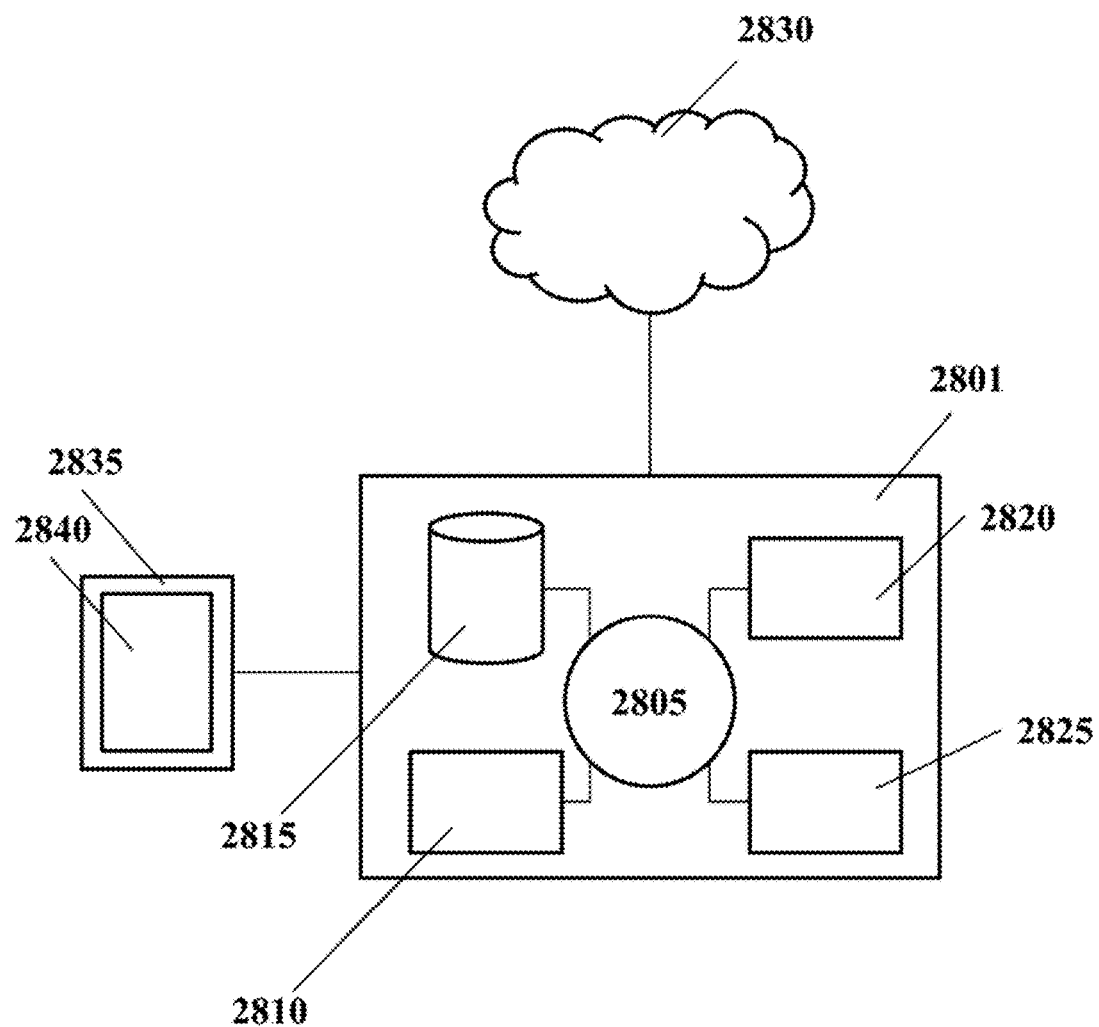
FIG. 28 shows an example computer system that is programmed or otherwise configured to regulate OCM reactions.

FIG. 28 shows a computer system 2801 that is programmed or otherwise configured to regulate heat exchange (e.g., for OCM reactions). The computer system 2801 can regulate, for example, fluid stream ("stream") flow rates, stream temperatures, stream pressures, and valve positions.

The computer system 2801 includes a central processing unit (CPU, also "processor" and "computer processor" herein) 2805, which can be a single core or multi core processor, or a plurality of processors for parallel processing. The computer system 2801 also includes memory or memory location 2810 (e.g., random-access memory, read-only memory, flash memory), electronic storage unit 2815 (e.g., hard disk), communication interface 2820 (e.g., network adapter) for communicating with one or more other systems, and peripheral devices 2825, such as cache, other memory, data storage and/or electronic display adapters. The memory 2810, storage unit 2815, interface 2820 and peripheral devices 2825 are in communication with the CPU 2805 through a communication bus (solid lines), such as a motherboard. The storage unit 2815 can be a data storage unit (or data repository) for storing data.

The CPU 2805 can execute a sequence of machine-readable instructions, which can be embodied in a program or software. The instructions may be stored in a memory location, such as the memory 2810. Examples of operations performed by the CPU 2805 can include fetch, decode, execute, and writeback.

The storage unit 2815 can store files, such as drivers, libraries and saved programs. The storage unit 2815 can store programs generated by users and recorded sessions, as well as output(s) associated with the programs. The storage unit 2815 can store user data, e.g., user preferences and user programs. The computer system 2801 in some cases can include one or more additional data storage units that are external to the computer system 2801, such as located on a remote server that is in communication with the computer system 2801 through an intranet or the Internet.

The computer system 2801 can be in communication with an OCM system 2830, including an OCM reactor and various process elements. Such process elements can include sensors, flow regulators (e.g., valves), and pumping systems that are configured to direct a fluid.

Methods as described herein can be implemented by way of machine (e.g., computer processor) executable code stored on an electronic storage location of the computer system 2801, such as, for example, on the memory 2810 or electronic storage unit 2815. The machine executable or machine readable code can be provided in the form of software. During use, the code can be executed by the processor 2805. In some cases, the code can be retrieved from the storage unit 2815 and stored on the memory 2810 for ready access by the processor 2805. In some situations, the electronic storage unit 2815 can be precluded, and machine-executable instructions are stored on memory 2810.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Although systems and methods of the present disclosure have been described in the context of methane and air (or oxygen), such systems and methods may be employed for use with other hydrocarbons and oxidizing agents (e.g., $NO_3$, $NO_2$, or $O_3$). Non-limiting examples of hydrocarbons include alkanes, alkenes, alkynes, aldehydes, ketones, and combinations thereof. For instance, mixers and integrated heat exchanges of the disclosure may be employed for use with ethane, propane, pentane, or hexane. Non-limiting examples of oxidizing agents include $O_2$, $H_2O_2$, $NO_3$, $NO_2$, $O_3$, and combinations thereof. Moreover, although certain examples of the present disclosure have made reference to air, other fluids containing oxygen or an oxidizing agent (e.g., $NO_2$) may be used.

EXAMPLES

Below are various non-limiting examples of uses and implementations of OCM catalysts and systems of the present disclosure.

Example 1: OCM System

Figure 29:
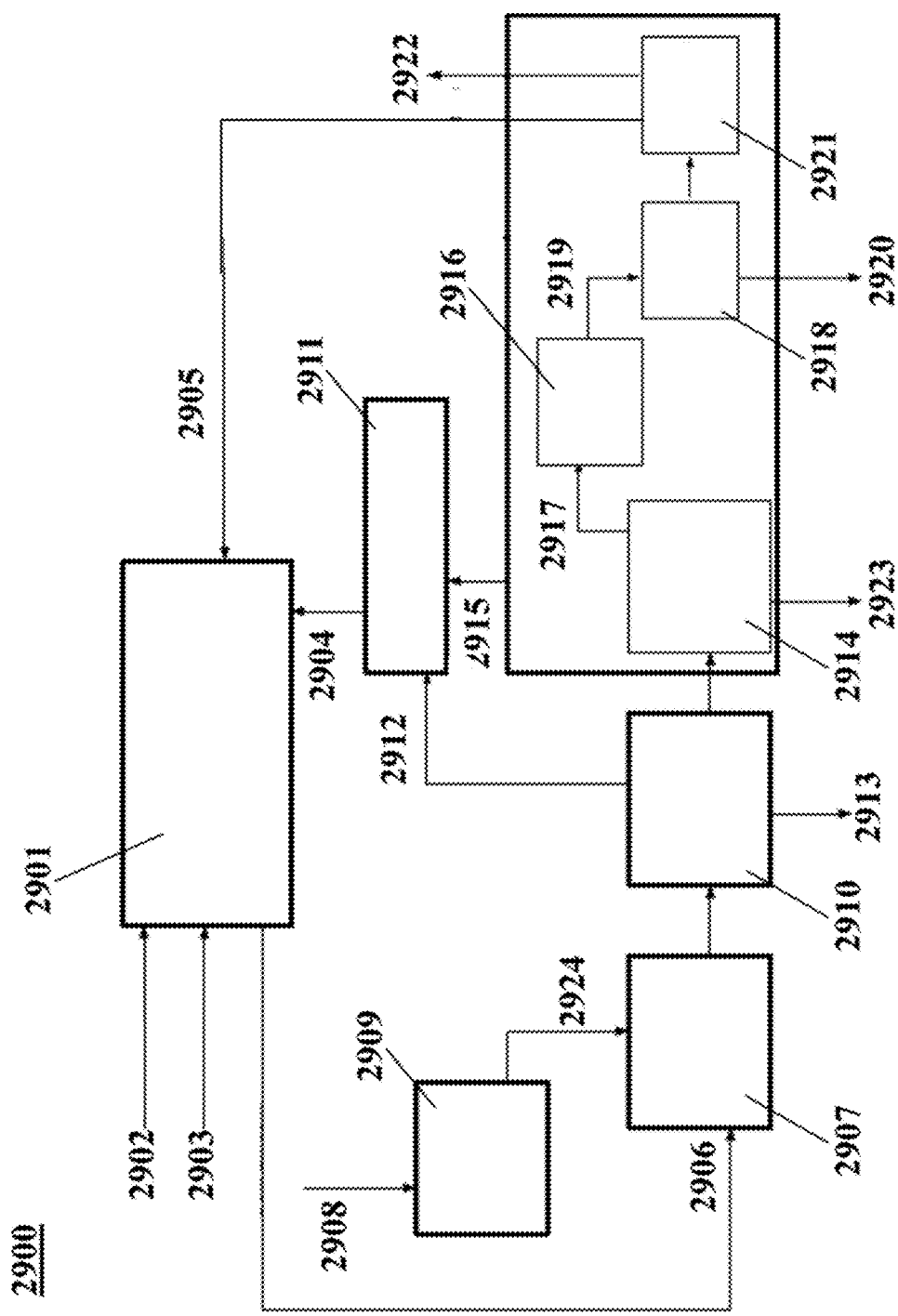
FIG. 29 is a block flow diagram of an example system that is configured to generate olefins, such as ethylene.

FIG. 29 is a block flow diagram of a system 2900 that is configured to generate olefins, such as ethylene. The system 2900 can be a small scale or world scale system. The system 2900 comprises an OCM sub-system 2901 that can include one or more OCM units in series and/or parallel. The OCM sub-system 2901 can include one or more post-bed cracking (PBC) units for generating olefins (e.g., ethylene) from alkanes (e.g., ethane and/or propane). A PBC unit can be disposed downstream of an OCM unit. The OCM unit and PBC unit can be situated in separate reactor, or included in the same reactor (e.g., a packed bed for OCM disposed upstream of a PBC unit in the same reactor). In some cases, an integrated OCM unit and PBC unit may be collectively referred to as an OCM reactor.

The OCM sub-system 2901 can accept ethane and an oxidizing agent (e.g., $O_2$). In the illustrated example, the OCM sub-system 2901 accepts ethane from ethane stream 2902 and oxygen ($O_2$) from oxygen stream 2903. Ethane can be injected into the OCM sub-system 2901 at a PBC unit of the OCM sub-system 2901. Oxygen can be provided by way of air or provided from an oxygen generation unit, such as a cryogenic unit that accepts air and generates individual $O_2$ and $N_2$ streams, or by $O_2$ pipeline. The OCM sub-system 2901 also accepts methane from $C_1$ recycle stream 2904 and ethane from $C_2$ recycle stream 2905.

In an OCM unit of the OCM sub-system 2901, methane can be catalytically reacted with oxygen in an OCM process to generate an OCM effluent stream 2906 comprising $C_{2+}$ compounds and non-$C_{2+}$ impurities. The OCM effluent stream 2906 can be directed to a PBC unit of the OCM sub-system 2901 to convert one or more alkanes in the OCM effluent stream 2906 to alkenes. Next, the OCM effluent stream 2906 can be directed to a process gas compressor (PGC) unit 2907. Natural gas (NG) is directed along an NG feed 2908 to a sulfur removal unit 2909, which can remove sulfur-containing chemicals from the NG feed 2908 to yield a sulfur-free methane feed 2924 to the PGC unit 2907. As an alternative, the sulfur removal unit 2909 can be excluded if the concentration of Sulfur in the incoming natural gas feed stream is very low and acceptable for the OCM process. As another alternative, the methane feed 2924 can be provided from other sources that may not be natural gas. In some cases, for example if the natural gas feed has a considerable quantity of hydrogen, it can be routed to the methanation unit. From the PGC unit 2907, the OCM effluent can be directed to $CO_2$ removal unit 2910, which can remove $CO_2$ from the OCM effluent. At least a portion of the removed $CO_2$ can be directed to a methanation unit 2911 along a $CO_2$ stream 2912. At least a portion of the removed $CO_2$ can be directed along $CO_2$ stream 2913 for other users, such as, for example, storage or purged from the $CO_2$ removal unit 2910. In some cases, the $CO_2$ removal system can comprise a pressure swing adsorption (PSA) unit; in other cases, the $CO_2$ removal system can be based on any other membrane separation process. The effluent from the $CO_2$ removal unit can be treated to remove water. The water removal system can be a molecular sieve dryer, or a series of dryers (not shown in the figure).

Next, the OCM effluent can be directed from the $CO_2$ removal unit 2910 to a demethanizer (also "de-methanizer" herein) unit 2914, which can separate methane from higher molecular weight hydrocarbons (e.g., acetylene, ethane and ethylene). The separated (or recovered) methane can be directed to the methanation unit 2911 along a $C_1$ recycle stream 2915. Alternatively, or in addition to, the separated methane can be directed to the OCM sub-system 2901. A purge stream 2923 can be directed out of the demethanizer unit 2914, which is a portion of stream 2915. The purge stream can contain methane and inert gas, such as, e.g., $N_2$, He or Ar. The purge flow rate may be sufficient such that the inert gas will not accumulate in the system. The purge stream may be required to remove inert gas(es) that are built-up in the recycle loop.

The methanation unit 2911 can generate methane from CO, $CO_2$ and $H_2$. Methane generated in the methanation unit 2911 can be directed to the OCM sub-system 2901 along C₁ recycle stream 104. The methanation unit 2911 can be as described elsewhere herein.

In some examples, the demethanizer unit 2914 includes one or more distillations columns in series and/or parallel. A serial configuration can enable the separation of different components. A parallel configuration can enable separation of a fluid stream of greater volumetric flow rate. In an example, the demethanizer unit 2914 comprises a distillation column and is configured to separate methane from $C_{2+}$ compounds in the OCM effluent stream. The demethanizer unit 2914 can be as described elsewhere herein.

Higher molecular weight hydrocarbons separated from methane in the demethanizer unit 2914 can be directed to an acetylene conversion unit 2916 along stream 2917. The acetylene conversion unit 2916 can react acetylene ($C_2H_2$) in the OCM effluent with $H_2$ to generate ethylene. The acetylene conversion unit 2916 in some cases can react other alkenes with $H_2$ to generate alkanes, such as ethane. The acetylene conversion unit 2916 can be a hydrogenation reactor. The OCM effluent stream can then be directed from the acetylene conversion unit 2916 to a deethanizer (also "de-ethanizer" herein) unit 2918 along stream 2919. The deethanizer unit 2918 can separate $C_2$ compounds (e.g., ethane and ethylene) from $C_{3+}$ compounds (e.g., propane and propylene). Separated $C_{3+}$ compounds can leave the deethanizer unit 2918 along stream 2920. $C_2$ compounds from the deethanizer unit 2918 can be directed to a $C_2$ splitter 2921, which can separate ethane from ethylene. The $C_2$ splitter 2921 can be a distillation column. Recovered ethylene can be directed along stream 2922 and employed for downstream use.

OCM effluent can be characterized by a particular ethane-to-ethylene ratio or range of ratios. For example, OCM effluent can have an ethane-to ethylene-ratio from about 3:1 to about 1:20. OCM effluent can have an ethane-to-ethylene ratio of at most about 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20.

OCM effluent can be characterized by a particular ratio or range of ratios of hydrocarbon compounds with three or more carbon atoms ("$C_{3+}$ compounds") to $C_2$ compounds. For example, OCM effluent can have a $C_{3+}$ compounds-to-$C_2$ compounds ratio from about 0 to about 1:3. OCM effluent can have a $C_{3+}$ compounds-to-$C_2$ compounds ratio (e.g., a molar ratio) of at least about 0, 1:1000, 1:100, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7, 1:6, 1:5, 1:4, or 1:3.

OCM effluent can be characterized by a particular acetylene-to-ethylene ratio or range of ratios. For example, OCM effluent can have an acetylene-to-ethylene ratio from about 0 to about 1:1. OCM effluent can have an acetylene-to-ethylene ratio (e.g., a molar ratio) of at least about 0, 1:1000, 1:100, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, or 1:1.

OCM effluent can be characterized by a particular CO-to-$CO_2$ ratio or range of ratios. For example, OCM effluent can have a CO-to-$CO_2$ ratio from about 0 to about 2:1. OCM effluent can have a CO-to $CO_2$ ratio (e.g., a molar ratio) of at least about 0, 1:1000, 1:100, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, or 2:1.

Systems, methods, and processes of the present disclosure, such as those for OCM-ETL, operate on feedstocks with particular ethane-to-methane ratios. For example, a system feedstock can have an ethane-to-methane ratio from about 0 to about 1:3. A system feedstock can have an ethane-to-methane ratio (e.g., a molar ratio) of at least about 0, 1:1000, 1:100, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7, 1:6, 1:5, 1:4, or 1:3.

The systems of the present disclosure, such as the system of FIG. 29, can be suited for the production of any olefin, such as, for example, ethylene. Thus, the systems above and elsewhere herein are not limited to ethylene but may be configured to generate other olefins, such as propylene, butenes, pentene, or other alkenes.

Post-bed cracking (PBC) units that may be suitable for use with systems of the present disclosure, such as the system of FIG. 29, are described in, for example, U.S. Patent Publication No. 2015/0152025, which is entirely incorporated herein by reference.

The system of FIG. 29 may employ different unit operations for small scale and world scale olefin production (e.g., ethylene production). The present disclosure provides non-limiting example unit operations and process flows for various units that may be employed for use with the system of FIG. 29.

Example 2: Implementation of OCM

About 1,000,000 metric tons/year of polymer grade ethylene is produced via the oxidative coupling of methane (OCM). The OCM reactor comprises a 2-stage adiabatic axial fixed bed that utilizes an OCM catalyst (e.g., nanowire catalyst) to convert methane and high purity oxygen to ethylene. The methane feed to the OCM reactor is the recycle stream from a downstream demethanizer over-head supplemented by CO and $CO_2$ conversion to methane in a two-stage methanation reactor. The hot OCM effluent from a second stage of the reactor effluent is mixed with heated recycle ethane from a downstream $C_2$ splitter and cracked to convert ethane primarily into ethylene. Hot reactor effluent is used to heat OCM reactor feed, generate high-pressure steam and heat process condensate. Cold reactor effluent is compressed and mixed with sulfur-free pipeline natural gas and treated to remove $CO_2$ and $H_2O$ prior to cryogenic separations. The treated process gas is fed to a demethanizer column to recover about 99% of ethylene as column bottoms stream. Demethanizer bottoms steam is separated in deethanizer column to separate $C_2$'s from $C_{3+}$ components. Deethanizer column overhead is first treated in selective hydrogenation unit to convert acetylene into ethylene and ethane using $H_2$ from a Pressure Swing Adsorption (PSA) Unit. The resulting stream is separated in a $C_2$ splitter unit to separate ethylene from ethane. Deethanizer bottoms stream is sent to a De-propanizer to obtain Refinery Grade Propylene (RGP) and mixed $C_{4+}$ stream, both which can be sold for credit. Ethane product stream from $C_2$ splitter bottoms is recycled to second stage of the OCM reactor to complete extinction. Polymer grade ethylene product (99.96 wt % ethylene) obtained from the $C_2$ splitter overhead is compressed to 1,000 psig and exported as vapor product. A stream factor of 0.95 is used (equal to an installed capacity of 1,059,000 metric tons/yr).

The OCM process generates superheated high pressure (~1500 psia) steam that is used to run process gas compressors, refrigeration compressors, ethylene heat pump/product compressors, and major pumps. The remainder of the steam and small portion of recycle methane (purge gas) can be exported to combined cycle/gas turbine system to generate power. The OCM process has an energy intensity of about −0.89 MMBTU/MT ethylene, while the energy intensity of a comparably sized steam cracking of ethane process is about 31.89 MMBTU/MT.

The reactor consists of a 2-stage adiabatic axial fixed bed with intermediate heat recovery via high-pressure steam generation. The methane stream recycled from the demethanizer overhead becomes the main OCM reactor feed. In both stages high purity oxygen is mixed with the hydrocarbon stream in a proportion of approximately 1:10 on a molar basis to achieve the optimal $O_2$-limited composition for the OCM reaction.

In the OCM reactor, the catalyst enables the partial and highly selective conversion of methane to, primarily, ethylene and ethane, with minor amounts of propylene and propane. Non-selective pathways include high temperature hydrocarbon reactions, such as combustion, reforming and shift. The second stage of the reactor may be configured to accommodate an ethane conversion zone immediately downstream of the catalytic bed. Ethane recycled from the deethanizer and, optionally, additional fresh ethane feed are injected into this reactor section where ethane undergoes highly selective adiabatic thermal de-hydrogenation to ethylene.

The OCM reactor effluent flows through a series of heat exchangers to achieve optimal heat recovery and final condensation at ambient temperature, prior to being sent to the Process Gas Compressor (PGC). The natural gas feed stream is mixed with the OCM reactor effluent at the PGC delivery. Gas treating, including $CO_2$ removal and drying, follows the compression step. The product recovery train consists of a demethanizer, deethanizer, acetylene converter and $C_2$ splitter configuration where the refrigeration and heat integration scheme may be configured to optimize heat recovery and minimize power consumption. The product streams comprise of polymer grade ethylene and a $C_{3+}$ mixed stream, similar in composition to Refinery Grade Propylene (RGP), which can be optionally further separated and purified. The $C_1$ recycle stream leaving the demethanizer head is sent to a conventional methanation unit where all CO and a portion of the $CO_2$ product react with hydrogen to form methane. The integration of the methanation unit into the overall process may be instrumental to maximizing the carbon efficiency of the OCM technology.

The OCM process may be energy neutral. The OCM reaction heat is utilized to provide mechanical power to the rotating units required for compression and pumping. The OCM process gets pure oxygen from an adjacent Air Separation Unit (ASU) which also houses a Gas Turbine Combined Cycle (GTCC). The GTCC unit is fed with the purge gas extracted from the demethanizer overhead and provides all the mechanical power and steam required by the ASU.

The final products are 1,000,000 metric tons per annum of polymer grade ethylene and 88,530 metric tons per annum of $C_{3+}$ hydrocarbons. The $C_{3+}$ hydrocarbons are sent to a depropanizer to obtain refinery grade propylene (65% propylene) as distillate.

Example 3: Dual Compartment Heat Exchanger

A dual compartment heat exchanger reduces a process gas temperature from 830° C. to 500° C. Specifically, a process gas exiting a post-bed cracking unit enters a first compartment of a dual compartment heat exchanger. The process gas may travel along the length of the first compartment, across a tube-sheet positioned substantially perpendicularly between the first and second compartments, into the second compartment, and exits the second compartment at an outlet. The tube sheet has a thickness of 50 millimeters. The process gas that enters the first compartment has a temperature of 830° C. The process gas that exits the second compartment has a temperature equal to a target temperature of 500° C. A steam drum is positioned adjacent to the first compartment for generating saturated steam. The saturated steam generated by the steam drum enters the second compartment and travels in co-current flow to the process gas and facilitates further cooling of the process gas. The first compartment is 4 meters in length. The second compartment is 6 meters in length. At the beginning of the run, the process fouling resistance is 0 meters squared Kelvin/Watts (m2·K/W). At the end of the process run, the process fouling resistance is 0.003 m2·K/W. The thermal conductivity of the tube sheet is 0.5 Watts per meter Kelvin (W/mK).

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. An apparatus for exchanging heat, the apparatus comprising:
   a first chamber and a second chamber;
   a plurality of tubes configured to contain a process fluid that flows from an inlet in the first chamber to an exit of the second chamber, passing through the first chamber and the second chamber; and
   a steam drum configured to contain a liquid phase and a gas phase of a cooling fluid, wherein (i) the steam drum is in fluidic communication with the first chamber such that the liquid phase of the cooling fluid is contacted with an exterior of the plurality of tubes in the first chamber to boil the cooling fluid using heat derived from the process fluid, and (ii) the steam drum is in fluidic communication with the second chamber such that the gas phase of the cooling fluid is contacted with an exterior of the plurality of tubes in the second chamber to super-heat the cooling fluid using heat derived from the process fluid.

2. The apparatus of claim 1, wherein the first chamber shares a wall with the second chamber.

3. The apparatus of claim 1, wherein each of the plurality of tubes comprises a first tube adjoined to a second tube to provide a continuous conduit for the process fluid.

4. The apparatus of claim 3, wherein the first tube passes through the first chamber and the second tube passes through the second chamber, and wherein the first chamber is adjoined to the second chamber.

5. The apparatus of claim 1, wherein the apparatus does not comprise a cross-over duct between the first chamber and the second chamber.

6. The apparatus of claim 1, wherein the first chamber comprises at least one of (a) a down-comer connected to the steam drum to distribute the cooling fluid over the exterior of the plurality of tubes, (b) a riser connected to the steam drum to collect the cooling fluid, and (c) a baffle that supports the plurality of tubes and/or guides the cooling fluid from the down-comer to the riser.

7. The apparatus of claim 6, wherein the apparatus comprises (a), (b) and (c).

8. The apparatus of claim 1, wherein the second chamber comprises a plurality of baffles that supports the plurality of tubes or directs the cooling fluid over the exterior of the plurality of tubes.

9. The apparatus of claim 1, further comprising an atomizer for adding an aerosol of the cooling fluid to the gas phase of the cooling fluid prior to flowing into the second chamber, which atomizer is controlled by a valve that is capable of modulating an amount of the cooling fluid that is super-heated in the second chamber.

10. The apparatus of claim 1, further comprising a valve that is capable of modulating an amount of the gas phase of the cooling fluid that is withdrawn from the steam drum, which valve is capable of modulating an amount of the super-heated cooling fluid that is produced.

11. The apparatus of claim 1, wherein the cooling fluid flows substantially perpendicularly with respect to the process fluid in the first chamber.

12. The apparatus of claim 1, wherein the cooling fluid flows substantially co-currently with the process fluid in the second chamber.

13. The apparatus of claim 1, wherein the first chamber is a fire-tube boiler or the second chamber is a fire-tube steam superheater.

14. A method for exchanging heat, the method comprising:
(a) providing a heat exchanger comprising a first chamber and a second chamber;
(b) flowing a process fluid into the first chamber at an initial temperature;
(c) in the first chamber, decreasing the initial temperature of the process fluid to an intermediate temperature by boiling a first quantity of a cooling fluid using a first quantity of heat derived from the process fluid;
(d) flowing the process fluid into the second chamber at the intermediate temperature; and
(e) in the second chamber, further decreasing the intermediate temperature of the process fluid to an exit temperature to a target temperature by super-heating the boiled cooling fluid from (b) using a second quantity of heat derived from the process fluid,
wherein no more than about 100 milliseconds (ms) of time passes between the process fluid reaching the intermediate temperature and initiation of super-heating the boiled cooling fluid.

15. The method of claim 14, wherein no more than about 10 milliseconds (ms) of time passes between the process fluid reaching the intermediate temperature and initiation of super-heating the boiled cooling fluid.

16. The method of claim 14, wherein a second quantity of the cooling fluid in thermal communication with the process fluid in (c) is not boiled.

17. The method of claim 14, further comprising, when the exit temperature is lower than the target temperature, decreasing the first quantity of the cooling fluid that is boiled, thereby increasing the exit temperature to the target temperature.

18. The method of claim 14, further comprising, when the exit temperature is greater than the target temperature, increasing the first quantity of the cooling fluid that is boiled, thereby decreasing the exit temperature to the target temperature.

19. The method of claim 14, wherein the cooling fluid is super-heated to at least about 500° C.

20. The method of claim 14, wherein a temperature of the process fluid is decreased from the initial temperature to the target temperature within about 250 milliseconds (ms).

* * * * *